(12) United States Patent
Ahn et al.

(10) Patent No.: US 11,976,219 B2
(45) Date of Patent: *May 7, 2024

(54) PHOTO-CLEAVABLE PRIMER COMPOSITIONS AND METHODS OF USE

(71) Applicant: Ormco Corporation, Orange, CA (US)

(72) Inventors: Byung Jun Ahn, Goleta, CA (US); Bruce H. Lipshutz, Santa Barbara, CA (US); Sam L. Nguyen, Saratoga, CA (US); Roscoe Linstadt, Palo Alto, CA (US)

(73) Assignee: Ormco Corporation, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/865,683

(22) Filed: Jul. 15, 2022

(65) Prior Publication Data

US 2023/0112086 A1 Apr. 13, 2023

Related U.S. Application Data

(60) Continuation of application No. 16/877,097, filed on May 18, 2020, now Pat. No. 11,453,790, which is a division of application No. 15/417,924, filed on Jan. 27, 2017, now Pat. No. 10,689,407.

(60) Provisional application No. 62/288,281, filed on Jan. 28, 2016, provisional application No. 62/309,162, filed on Mar. 16, 2016.

(51) Int. Cl.
| | | |
|---|---|---|
| C09D 7/63 | (2018.01) |
| A61K 6/20 | (2020.01) |
| A61K 6/62 | (2020.01) |
| A61K 6/65 | (2020.01) |
| A61K 6/78 | (2020.01) |
| B05D 3/00 | (2006.01) |
| B05D 3/10 | (2006.01) |
| C07C 69/01 | (2006.01) |
| C07C 205/42 | (2006.01) |
| C07C 205/43 | (2006.01) |
| C07C 235/06 | (2006.01) |
| C07C 235/20 | (2006.01) |
| C07C 271/16 | (2006.01) |
| C07D 217/16 | (2006.01) |
| C07F 7/08 | (2006.01) |
| C07F 9/12 | (2006.01) |
| C07F 9/62 | (2006.01) |
| C09D 5/00 | (2006.01) |
| C08K 5/107 | (2006.01) |
| C08K 5/13 | (2006.01) |

(52) U.S. Cl.
CPC .................. *C09D 7/63* (2018.01); *A61K 6/20* (2020.01); *A61K 6/62* (2020.01); *A61K 6/65* (2020.01); *A61K 6/78* (2020.01); *B05D 3/002* (2013.01); *B05D 3/10* (2013.01); *B05D 3/107* (2013.01); *C07C 69/01* (2013.01); *C07C 205/42* (2013.01); *C07C 205/43* (2013.01); *C07C 235/06* (2013.01); *C07C 235/20* (2013.01); *C07C 271/16* (2013.01); *C07D 217/16* (2013.01); *C07F 7/0896* (2013.01); *C07F 9/12* (2013.01); *C07F 9/62* (2013.01); *C09D 5/002* (2013.01); *C08K 5/107* (2013.01); *C08K 5/13* (2013.01)

(58) Field of Classification Search
CPC .......... B05D 3/002; B05D 3/10; C08K 5/107
See application file for complete search history.

(56) References Cited

U.S. PATENT DOCUMENTS

| | | | |
|---|---|---|---|
| 6,043,065 A | 3/2000 | Kao et al. | |
| 2005/0182148 A1* | 8/2005 | Gaud ................ A61K 6/20 | |
| | | | 522/1 |
| 2009/0209556 A1 | 8/2009 | Bittner et al. | |

FOREIGN PATENT DOCUMENTS

| | | |
|---|---|---|
| WO | WO2002/06246 | 1/2002 |
| WO | WO2008/033455 | 3/2008 |
| WO | WO2015/057511 | 4/2015 |

OTHER PUBLICATIONS

D.R.Griffin, ACS Macro Letters, Photoselective Delivery of Model Therapeutics from Hydrogels, 2012, 1, 1330-1334, American Chemical Society.

G. Hanson, Journal of Organic Chemistry, 1981, 46, 5441-5443; American Chemical Society.

* cited by examiner

*Primary Examiner* — Nathan T Leong
(74) *Attorney, Agent, or Firm* — HDC IP Law, LLP; Sam L. Nguyen

(57) ABSTRACT

In one embodiment, the present application discloses a photo-cleavable surface binding compound of the Formula I and Formula II:

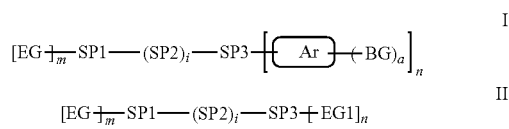

wherein the variables EG, EG1, SP1, SP2, SP3, Ar and BG are as defined herein. In another embodiment, the application discloses a method for forming a coating on a surface of a substrate using the surface binding compound.

15 Claims, No Drawings

PHOTO-CLEAVABLE PRIMER COMPOSITIONS AND METHODS OF USE

RELATED APPLICATIONS

The present application is a Continuation of U.S. application Ser. No. 16/877,097, filed on May 18, 2020 and issued as U.S. Pat. No. 11,453,790 B2 on Sep. 27, 2022, which is a Divisional of U.S. application Ser. No. 15/417,924 filed on Jan. 27, 2017 and issued as U.S. Pat. No. 10,689,407 on Jun. 2, 2020, which claims the benefit of U.S. Provisional Application No. 62/309,162 filed Mar. 16, 2016 and U.S. Provisional Application No. 62/288,281 filed Jan. 28, 2016, the disclosures of which are incorporated herein in its entirety.

BACKGROUND

Strong bidentate bonding, such as hydrogen bonding with catecholic groups, chelation to metals, and metal-oxygen coordination of the catechols and their applications as primers containing a catechol functional group are known in the art. These catecholic compounds form strong hydrogen bonds and chelating bonds with different minerals and metal oxide surfaces.

Photo-cleavage of a building block at specific sites has been reported in patents [e.g., photo-cleavable linkers for oligonucleotides (EP0233053A2), nucleotide (U.S. Pat. No. 5,241,060) for nucleic acid sequence determination (U.S. Pat. No. 5,366,860)] and non-patent reports [e.g., photo-cleavable degradation (depolymerization) of hydrogels (see Z., Shafiq et al., Bioinspired Underwater Bonding and Debonding on Demand. *Angew. Chem., Int. Ed.* 51, 4332-4335 (2012)), photocleavable dissociation of block copolymer micelles (see B. Yan et al., Near-Infrared Light-Triggered Dissociation of Block Copolymer Micelles Using Upconverting Nanoparticles, *J. Am. Chem. Soc.* 133, 19714-19717 (2011)) and DNA labels (see B. Nie et al., Surface invasive cleavage assay on a maskless light-directed diamond DNA microarray for genome-wide human SNP mapping, *Analyst* 140, 4549-4557 (2015)]. To date, there appears to be no reports on the use of a photo-cleavable primer for debonding or cleaving of adhesives; although ultraviolet (UV)-initiated photo-cleavable co-monomer has been claimed as one of the ingredients in a dental composite (PCT/US2007/014158) and copolyester network (see S. M. June et al., Photoactive Polyesters Containing o-Nitro Benzyl Ester Functionality for Photodeactivatable Adhesion, *The Journal of Adhesion* 89, 548-558 (2013). When cross-linked/cured adhesives are used, the debonding of adhesives is very difficult or seemingly impossible without breakage or fracture of the glued/bonded/adhered objects or the surface of the objects.

SUMMARY OF THE INVENTION

In constrast to prior publications using UV irradiation to depolymerize dental composites (PCT/US2007/014158) or copolymer, the present application discloses a cleavage or debonding process between a mineral/metal/oxide-containing surface and a (co)polymer/adhesive/resin surface by specifically cleaving the primer compound using infrared (IR), ultraviolet (UV) and/or a combination of IR and UV irradiation. In one embodiment, the application discloses photocleavable primers for debonding of adhesives by cleaving a covalent bond of the primer compound. In one aspect, the debonding is controlled and selective on a particular position on the primer compound, and does not result in a breakage or an uncontrolled depolymerization of the primer or adhesive and/or substrate surface. In one particular aspect, the present technology is applicable to dental adhesives.

In one embodiment, the present application discloses a photo-cleavable surface binding compound of the Formula I and Formula II:

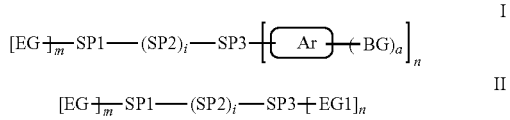

wherein the variables EG, EG1, SP1, SP2, SP3, Ar and BG are as defined herein. In another embodiment, the application discloses a method for forming a coating on a surface of a substrate using the surface binding compound of the Formula I or II.

DETAILED DESCRIPTION OF THE INVENTION

In one embodiment, the present application discloses novel, structurally defined, small molecule compounds as primers and adhesives for medical, dental and electronic applications. In one embodiment, the present application discloses primers, including polyhydroxy aromatic compounds, such as tri-, tetra- and penta-hydroxy benzene, indole and imidazole moieties and their derivatives, that may form bonds, such as hydrogen bonds and/or attach via chelation or a coordination on to a material surface, such as a mineral, metal or oxide-containing surface of a material. In one aspect, these head moities adhere/adsorb on to mineral and metal oxide surfaces and generate secondary surfaces to interact (or crosslink) with bulk adhesive, resins or co-polymer surfaces to enhance performance of bonding between minerals, metals and metal oxide containing surfaces. Non-exclusive material surfaces include adhesives, cements, resins, paints, inks, proteins etc . . . .

Some embodiments of the present invention are discussed in detail below. In describing embodiments, specific terminology is employed for the sake of clarity. However, the present application is not intended to be limited to the specific terminology so selected. A person skilled in the relevant art will recognize that other equivalent components can be employed and other methods developed without departing from the broad concepts of the current invention. All references cited anywhere in this specification are incorporated by reference into this disclosure.

In one embodiment, the application discloses compounds comprising an aromatic group-containing surface primer. In one aspect, the surface primer contains an aromatic group. In another aspect, the compound comprises an aromatic group attached to a functional end group through a spacer group. In another embodiment, the compounds undergo self-assembly onto a substrate, such as a mineral substrate or a metal oxide substrate. When applied to an oxide containing surface, the aromatic group of the compound may self-assemble and form a bond, such as a hydrogen bond, onto the oxide containing surface.

In another aspect, the compound forms a chelate or a coordination complex on to the metal surface of a substrate. The functional end group of the compound can form a secondary surface layer to interact/crosslink with bulk materials chemically, physico-chemically or physically via cross-linking, hydrogen bonding, oxide-metal coordination, electrostatic or hydrophobic interaction. A secondary surface can optionally be applied onto the primer. According to the present process, the secondary layer may be tunable by modifying the compound, including the functional end group of the aromatic group.

In one embodiment, the present application discloses a surface binding compound of the Formula I:

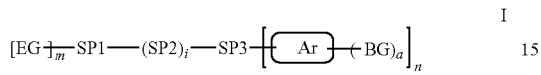

I wherein:

each a is independently 1, 2, 3, 4 or 5;

m is 1, 2 or 3; n is 1, 2 or 3; i is 1, 2 or 3 each EG is an end group independently selected from the group consisting of a $C_{1-2}$alkyl, $CH_2$=CH—, $CH_2$=C($C_{1-3}$alkyl)—, $CH_2$=CHC(O)—, $CH_2$=C($C_{1-3}$alkyl)C(O)—, $CH_2$=CHC(O)O—, $CH_2$=C($C_{1-3}$alkyl)C(O)O—, $CH_2$=C(phenyl)C(O)O—, $CH_2$=C($C_{1-3}$alkyl)S(O)$_n$O—, isocyanate, epoxy, oxetanyl, styrenyl, vinyl ether, (OH)SiR$_2$—, (OH)SiR$_2$(O)—, —Ar—(BG)$_a$, aryl, heteroaryl, —N$^+$R$_1$R$_2$R$_3$, —PO$_4^-$, —N$^+$R$_1$R$_2$R$_3$X$^-$, —PO$_4^-$Y$^+$, —SO$_4^-$Y$^+$, wherein each R, R$_1$, R$_2$ and R$_3$ is independently H and $C_{1-3}$alkyl, X$^-$ is Cl$^-$, Br$^-$ and I$^-$ and Y$^+$ is H$^+$ or N$^+$R$_1$R$_2$R$_3$;

each of SP1, SP2 and SP3 is a spacer independently selected from the group consisting of —O—, —C(O)—, —S—, —S(O)—, —S(O)$_2$—, —N—, —NH—, —NCH$_3$—, —C—, —CH—, —(CH$_2$)$_q$—, —(CH(OH))$_q$—, —(CH$_2$CH(OH)CH$_2$)$_q$—, —(C(CH$_3$)$_2$)$_q$—, —(CH(CH$_3$))$_q$—, —NH(CH$_2$)$_2$NH—, —OC(O)—, —CO$_2$—, —NHCH$_2$CH$_2$C(O)—, —OCH$_2$CH$_2$C(O)—, —C(O)CH$_2$CH$_2$C(O)—, —C(O)NHCH$_2$CH$_2$NH—, —NHCH$_2$C(O)—, —NHC(O)—, —C(O)N—, —NC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, —OCH(CH$_2$O—)$_2$—, —(CH$_2$)$_q$—N$^+$R$_1$R$_2$—, —(CH$_2$)$_q$—PO$_4^-$—, —N$^+$R$_1$R$_2$—, —PO$_4^-$—, —(CH$_2$)$_q$—N$^+$R$_1$R$_2$—X$^-$—, —(CH$_2$)$_q$—PO$_4^-$Y$^+$—, —N$^+$R$_1$R$_2$—X$^-$—, —PO$_4^-$Y$^+$—, —SO$_4^-$Y$^+$—, —O—PO$^-$(O)O—(CH$_2$)$_{2-4}$—N$^+$(R$_1$R$_2$)—, —(AA)$_r$-, aryl, cyclopentanyl, cyclohexanyl, unsubstituted phenylenyl and phenylenyl substituted by 1 or 2 substituents selected from the group consisting of halo, CF$_3$—, CF$_3$O—, CH$_3$O—, —C(O)OH, —C(O)OC$_{1-3}$alkyl, —C(O)CH$_3$, —CN, —NH$_2$, —OH, —NHCH$_3$, —N(CH$_3$)$_2$ and $C_{1-3}$alkyl, wherein each AA is independently an amino acid, p is 1-6, q is 1-6 and r is 1-6;

Ar is an aryl or heteroaryl group;

each BG is a bonding group independently selected from the group consisting of —OH, —SiR$_2$OH, —COOH, —SO$_3$H, —P(O)$_3$OH, —CONH$_2$, —CSNH$_2$, —CF$_3$, —CF$_2$CF$_3$, —OCF$_3$ and —OCF$_2$CF$_3$;

provided that:

a) at least one of SP1, SP2 and SP3 is a spacer selected from the group consisting of A, A1, A2, B, C, D, E, F, G, H, H-1, I, I-1, J, J-1, K, K-1, L, L-1, M, M-1, N, O, P, Q and R:

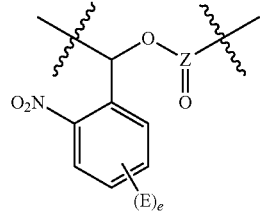

A

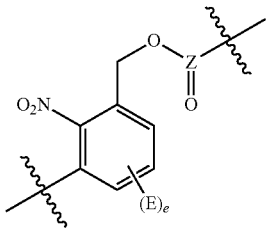

B

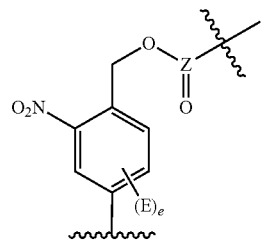

C

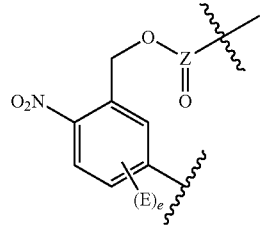

D

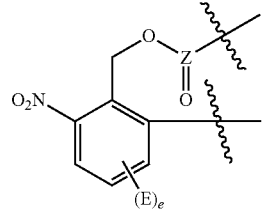

E

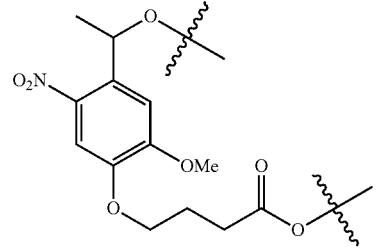

A1

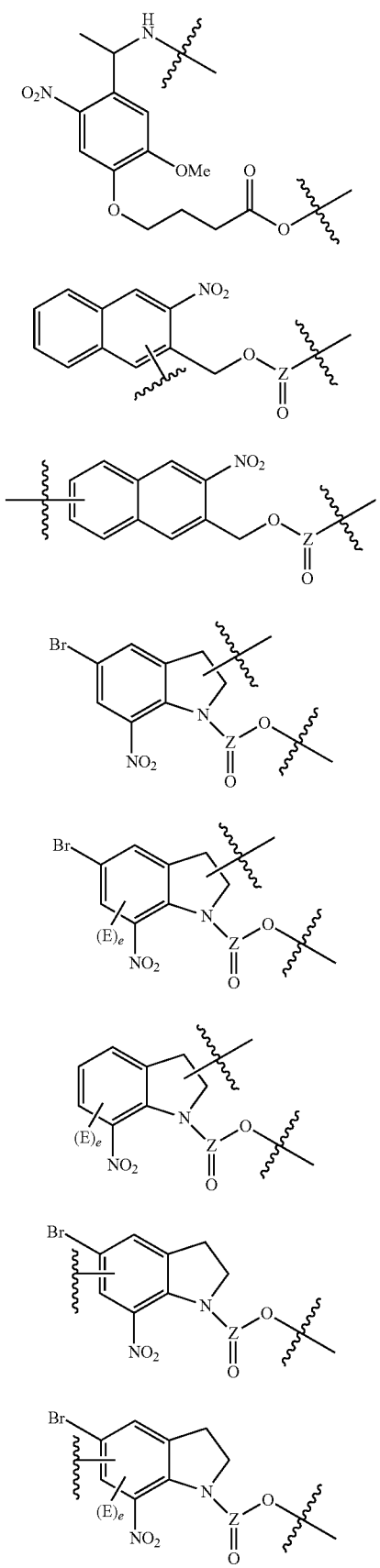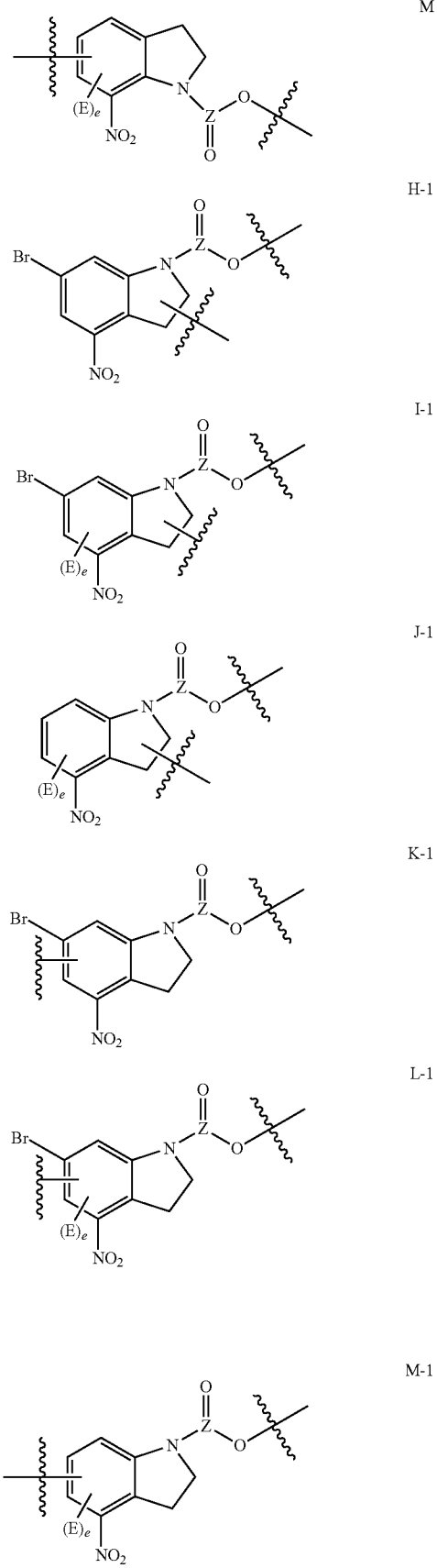

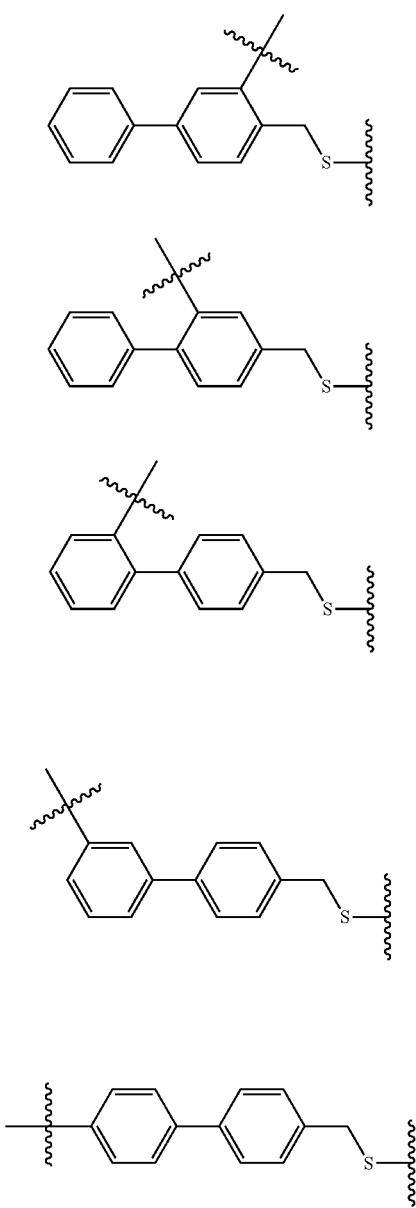
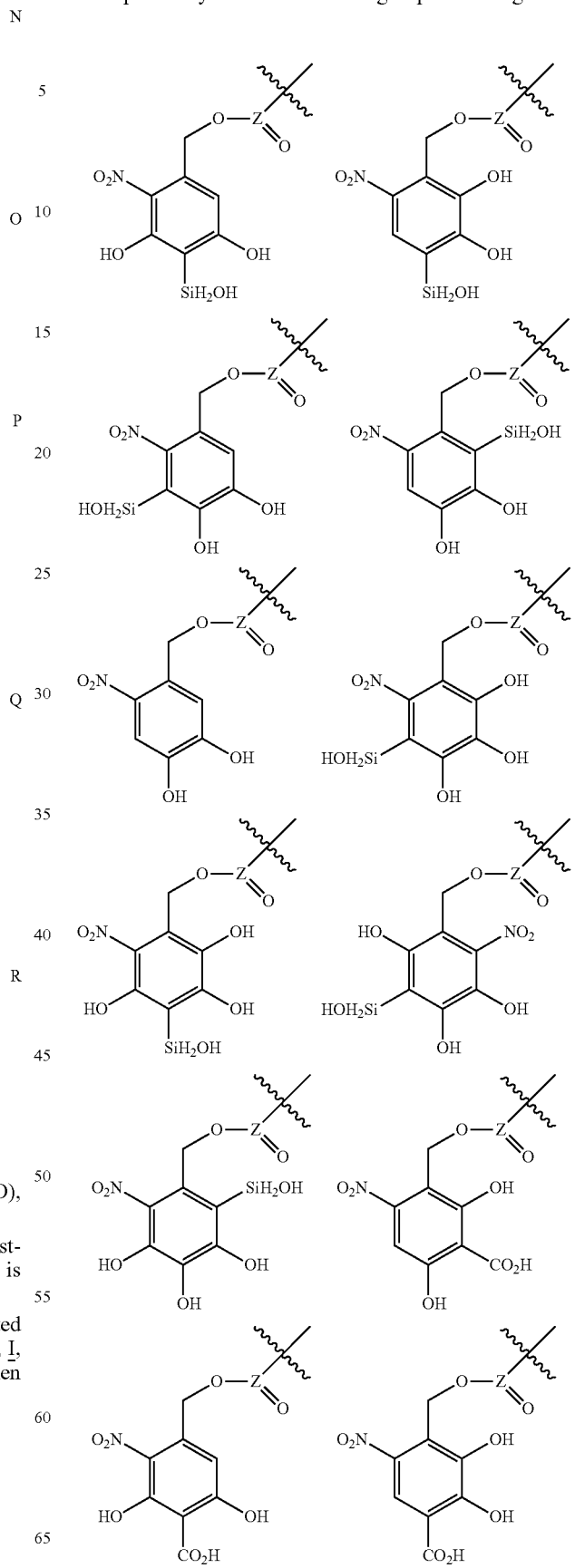
wherein:
Z is selected from the group consisting of C, S, S(O), P(OH) and P(OR);
each E is independently selected from the group consisting of halo, $CF_3-$, $CF_3O-$, $HO-$ and $CH_3O-$; and e is 0, 1, 2 or 3; and
b) when one of SP1, SP2 and SP3 is not a spacer selected from the group consisting of A, B, C, D, E, F, G, H, H-1, I, I-1, J, J-1, K, K-1, L, L-1, M, M-1, N, O, P, Q and R, then each of the groups
is independently selected from the group consisting of:

-continued
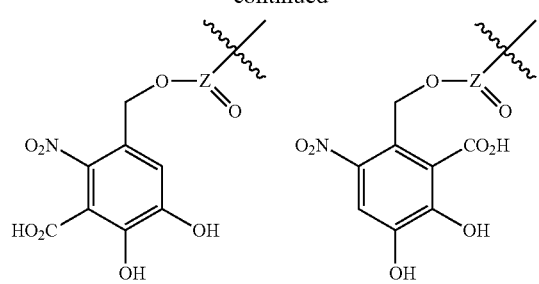
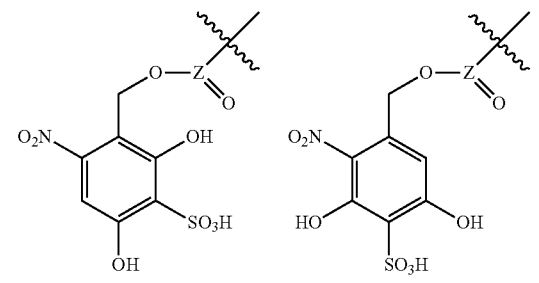
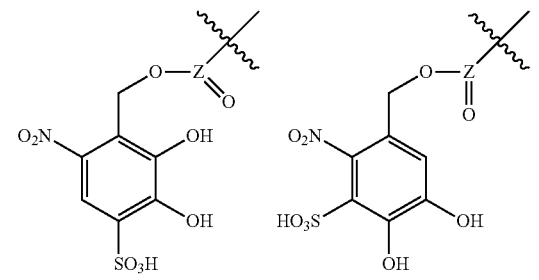
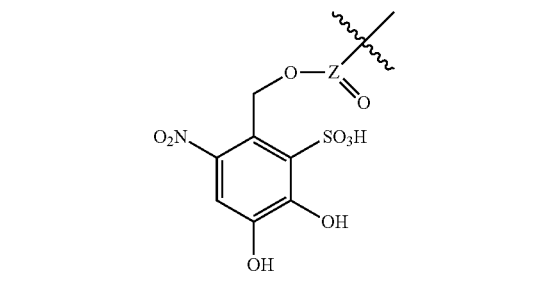
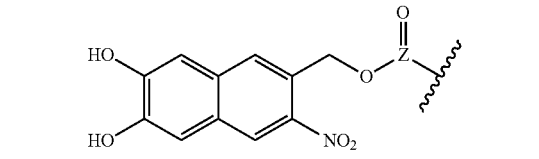
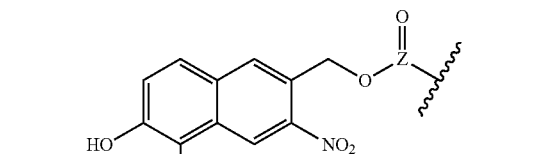
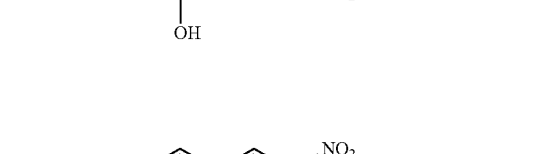
-continued
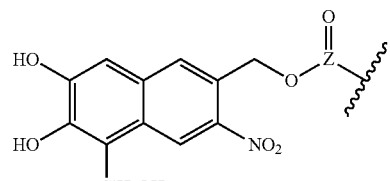
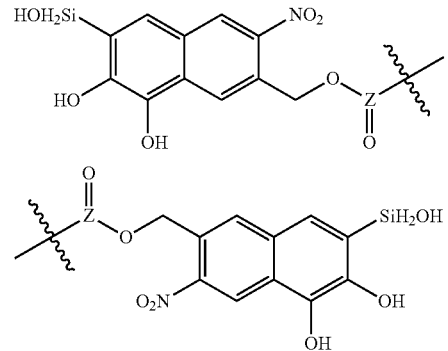
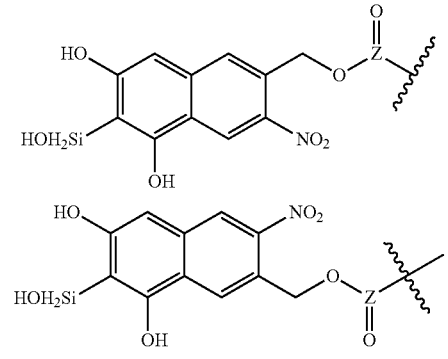
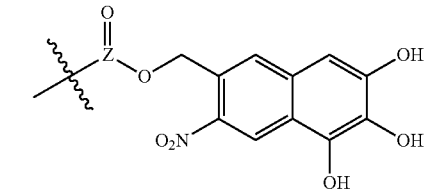
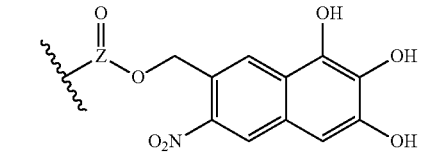
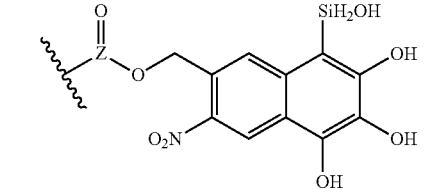
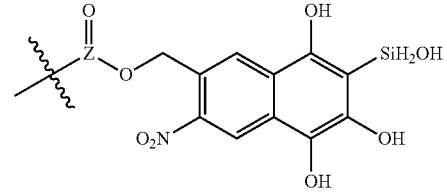

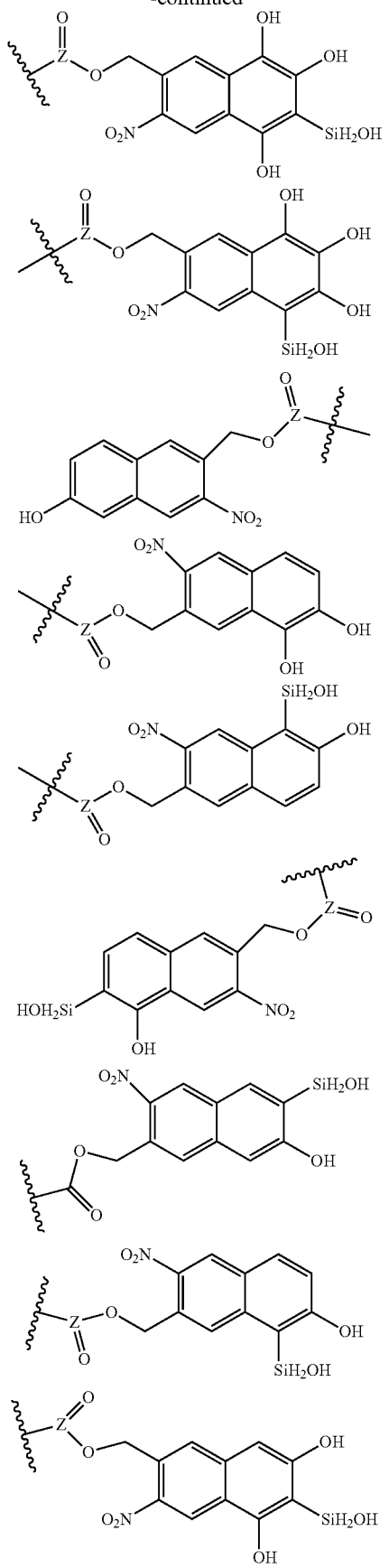
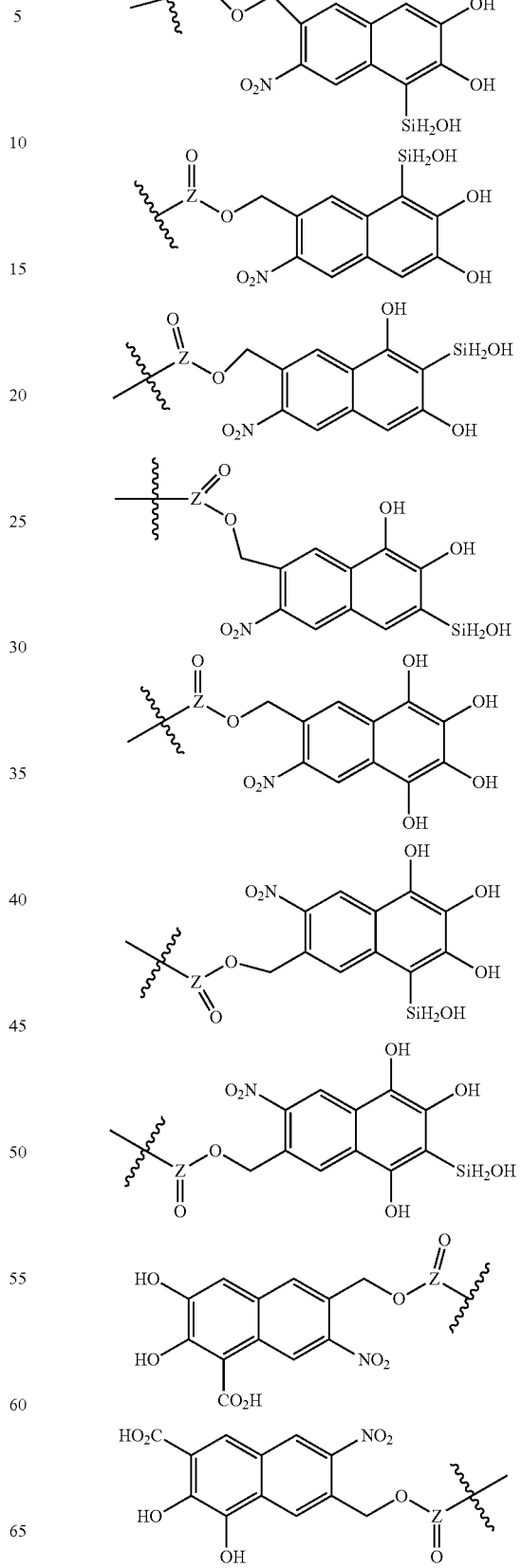

-continued

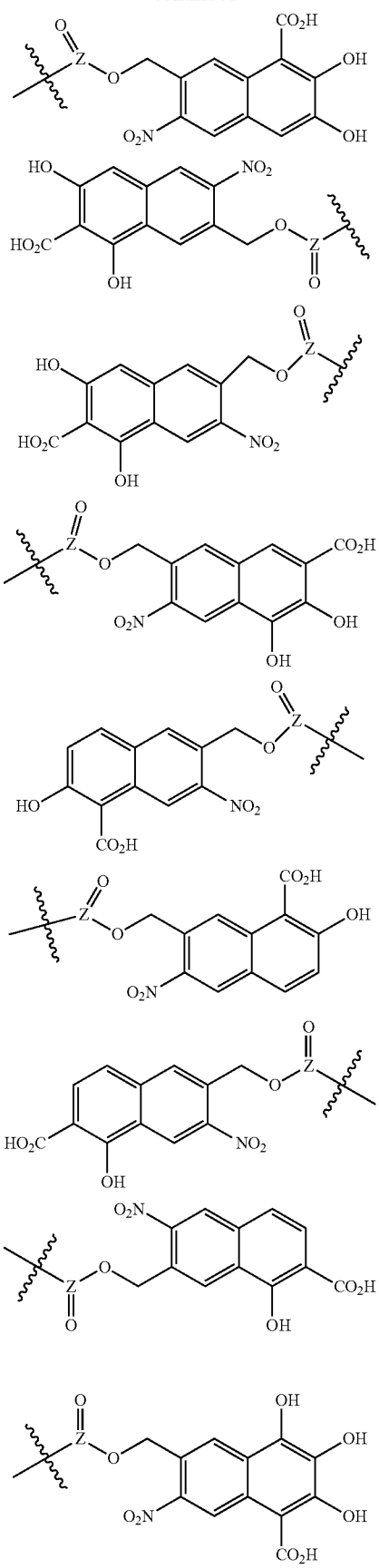

-continued

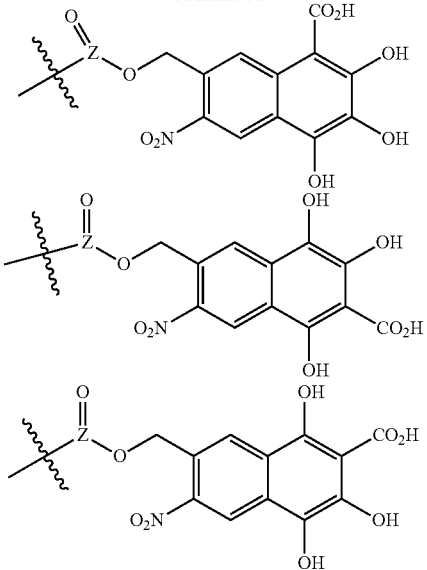

wherein: each Z is independently selected from the group consisting of C, S, S(O), P(OH) and P(OR). In one variation of the compounds, Z is C or S.

In another embodiment, there is provided a surface binding compound of the Formula II:

$$[EG\!\!-\!\!]_m\text{SP1}\!\!-\!\!(\text{SP2})_i\!\!-\!\!\text{SP3}\!\!-\!\![EG1]_n$$    II wherein: m is 1, 2 or 3; n is 1, 2 or 3; i is 1, 2 or 3;

each EG and EG1 is an end group independently selected from the group consisting of a $C_{1-2}$alkyl, $CH_2$=CH—, $CH_2$=C($C_{1-3}$alkyl)—, $CH_2$=CHC(O)—, $CH_2$=C($C_{1-3}$alkyl)C(O)—, $CH_2$=CHC(O)O—, $CH_2$=C($C_{1-3}$alkyl)C(O)O—, $CH_2$=C(phenyl)C(O)O—, $CH_2$=C($C_{1-3}$alkyl)S(O)$_n$O—, isocyanate, epoxy, oxetanyl, styrenyl, vinyl ether, $(OH)SiR_2$—, $(OH)SiR_2(O)$—, —Ar—$(BG)_a$, aryl, heteroaryl, —$N^+R_1R_2R_3$, —$PO_4$—, —$N^+R_1R_2R_3X^-$, —$PO_4^-Y^+$, —$SO_4^-Y^+$, wherein each R, $R_1$, $R_2$ and $R_3$ is independently H and $C_{1-3}$alkyl, $X^-$ is $C^-$, BP and $I^-$ and $Y^+$ is $H^+$ or $N^+R_1R_2R_3$;

each of SP1, SP2 and SP3 is a spacer independently selected from the group consisting of —O—, —C(O)—, —S—, —S(O)—, —S(O)$_2$—, —N—, —NH—, —NCH$_3$—, —C—, —CH—, —(CH$_2$)$_q$—, —(CH(OH))$_q$—, —(CH$_2$CH(OH)CH$_2$)$_q$—, —(C(CH$_3$)$_2$)$_q$—, —(CH(CH$_3$))$_q$—, —NH(CH$_2$)$_2$NH—, —OC(O)—, —CO$_2$—, —NHCH$_2$CH$_2$C(O)—, —OCH$_2$CH$_2$C(O)—, —C(O)CH$_2$CH$_2$C(O)—, —C(O)NHCH$_2$CH$_2$NH—, —NHCH$_2$C(O)—, —NHC(O)—, —C(O)N—, —NC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, —OCH(CH$_2$O—)$_2$—, —(CH$_2$)$_q$—$N^+R_1R_2$—, —(CH$_2$)$_q$—$PO_4^-$—, —$N^+R_1R_2$—, —$PO_4^-$—, —(CH$_2$)$_q$—$N^+R_1R_2$—$X^-$—, —(CH$_2$)$_q$—$PO_4^-Y^+$—, —$N^+R_1R_2X^-$—, —$PO_4^-Y^+$—, —$SO_4^-Y^+$—, —O—PO$^-$(O)O—(CH$_2$)$_{2-4}$—$N^+(R_1R_2)$—, —(AA)$_r$-, aryl, cyclopentanyl, cyclohexanyl, unsubstituted phenylenyl and phenylenyl substituted by 1 or 2 substituents selected from the group consisting of halo, CF$_3$—, CF$_3$O—, CH$_3$O—, —C(O)OH, —C(O)OC$_{1-3}$alkyl, —C(O)CH$_3$, —CN, —NH$_2$, —OH, —NHCH$_3$, —N(CH$_3$)$_2$ and C$_{1-3}$alkyl, wherein each AA is independently an amino acid, p is 1-6, q is 1-6 and r is 1-6;
provided that at least one of SP1, SP2 and SP3 is a spacer selected from the group consisting of A, B, C, D, E, F, G, H, H-1, I, I-1, J, J-1, K, K-1, L, L-1, M, M-1, N, O, P, Q and R:
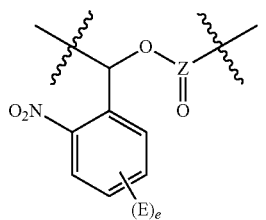
A
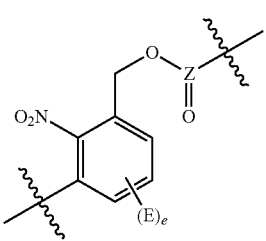
B
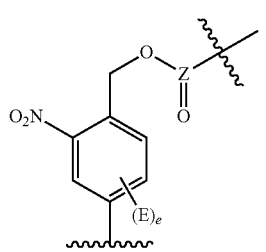
C
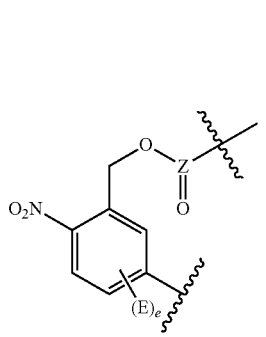
D
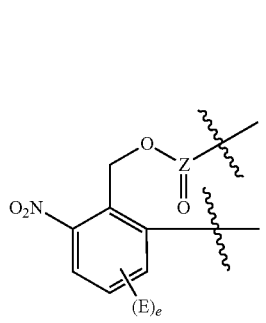
E
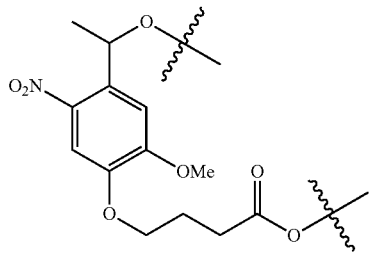
A1
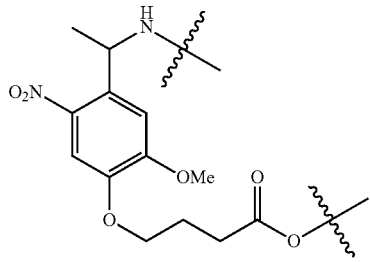
A2
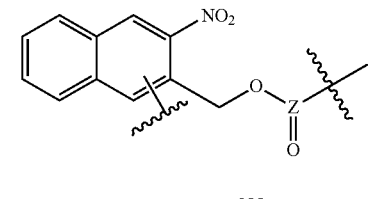
F
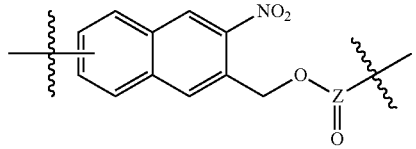
G
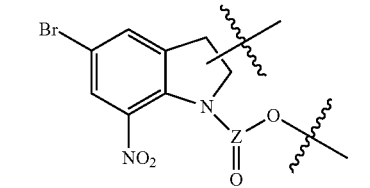
H
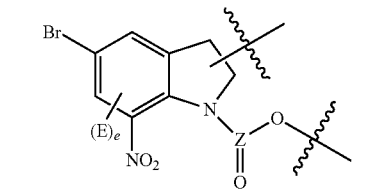
I
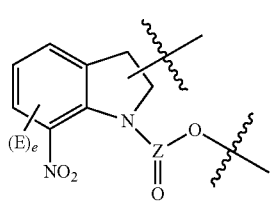
J

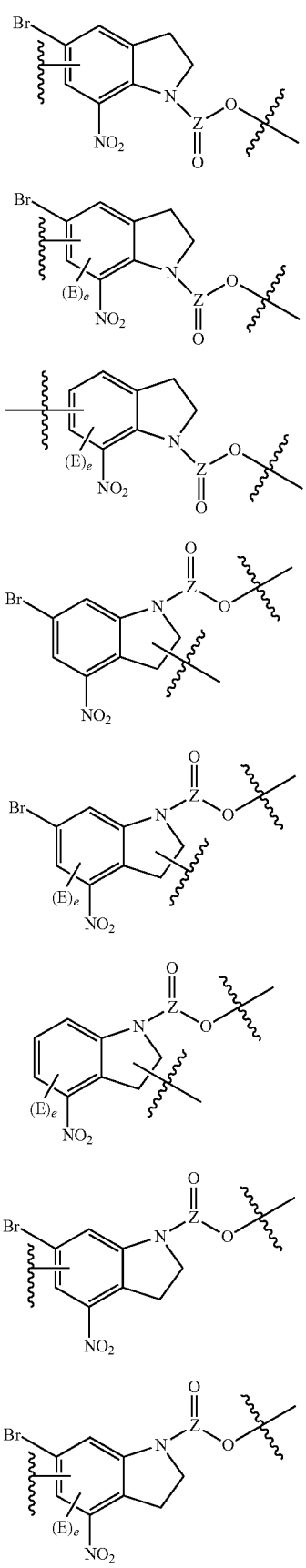
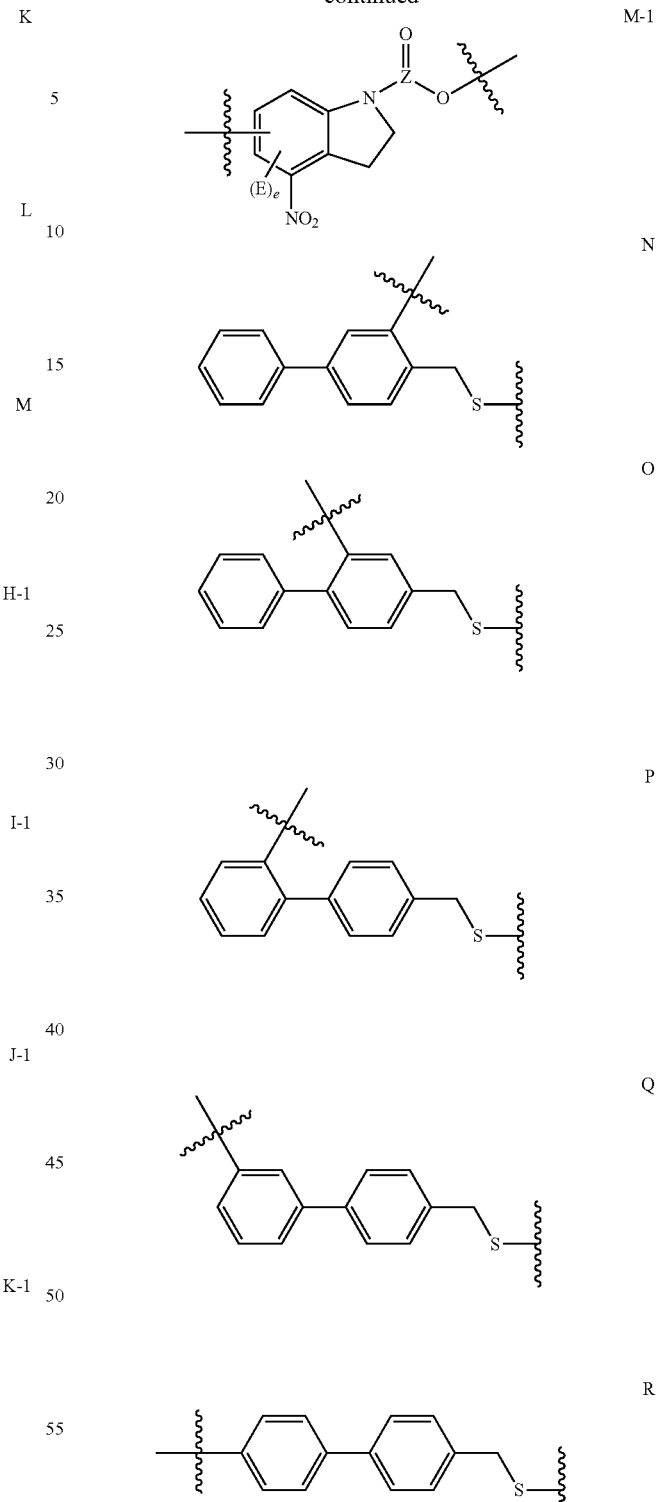
wherein: Z is selected from the group consisting of C, S, S(O), P(OH) and P(OR); each E is independently selected from the group consisting of halo, $CF_3$—, $CF_3O$—, HO— and $CH_3O$—; and e is 0, 1, 2 or 3; and provided that when EG and EG1 are both $CH_2$=$C(CH_3)C(O)O$—$(CH_2CH_2)OC(O)$— or $CH_2$=$C(CH_3)C(O)NH$—$(CH_2CH_2)OC(O)$—, then the spacer is not

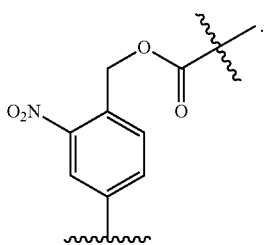 [SMILES: *C(=O)OCc1ccc(*)cc1[N+](=O)[O-]]

As provided herein and used conventionally in the art for the compounds of Formula I or II, the —Ar—BG group may be referred to as the head group, and the —EG group may be referred to as the tail group of the self-assembled layer or self assembled monolayer (SAM). As used herein, the formation of SAMs refers to the spontaneous formation of organic assemblies of the compound of the Formula I or II on a surface by the adsorption of compounds from the solution comprising the compounds by a process of synergistic intermolecular and/or intramolecular interactions. In another variation, the compound comprises of the formulae IIa, IIb, IIc, IId, IIe, IIf, IIg and IIk:

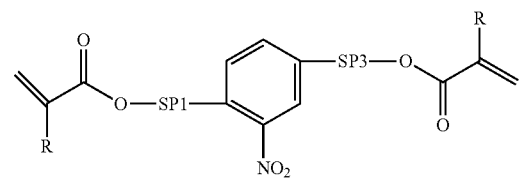

IIa: R = H
IIb: R = Me

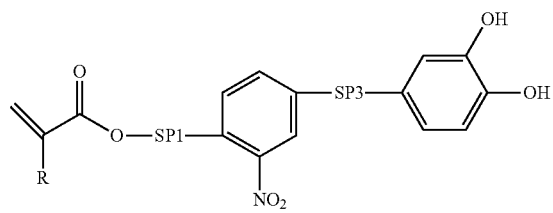

IIc: R = H
IId: R = Me

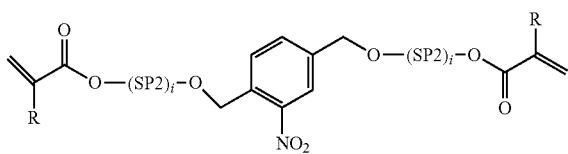

IIe: R = H
IIf: R = Me

IIg

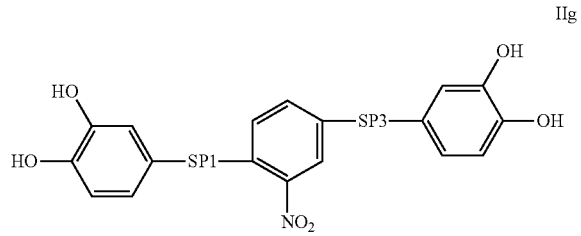

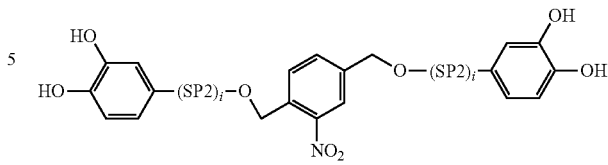

IIh wherein i, R, SP1 and SP3 are as defined in Formula II.

In one variation of the compound of the Formula I, —Ar—BG is not a 3,4-dihydroxyphenyl group. As defined herein, when each of SP1, SP2 and SP3 is independently a —N—, —C—, —C(O)N— or —NC(O)— group, these trivalent and tetravalent groups may be substituted and may form branched structures, leading up to various arrays, as represented by, e.g., dendrimeric species. For example, when SP1 is —N— or —C—, the compound of the Formula I (or Formula II) may form a branched structure at the nitrogen atom or carbon atom, respectively, as shown:

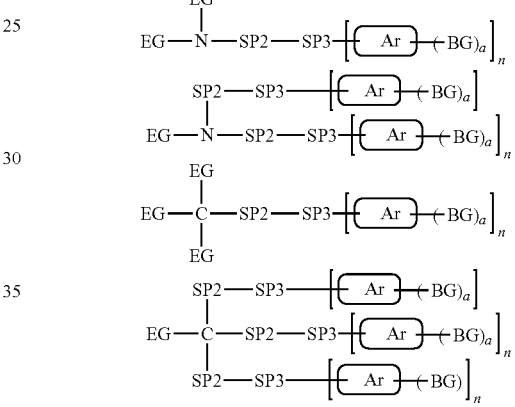

Similarly, branched structures may also be formed with SP1 and SP2, SP2 and SP3, or a combination of SP1, SP2 and SP3.

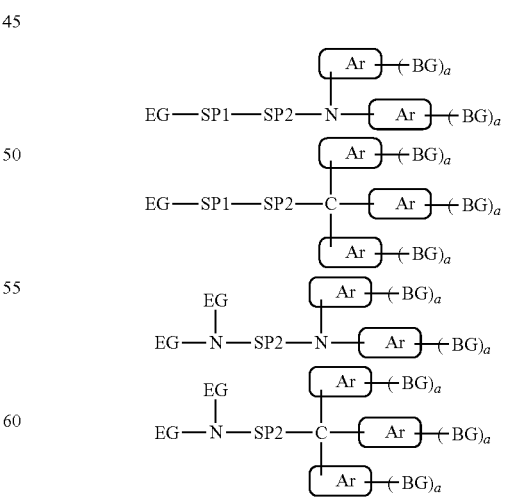

The dendrimer-like or branched structures disclosed above may also be similarly applicable for the compound of the Formula II. As provided herein for example, a spacer designated or bonded as —C(O)NH— also include the reversible (inverted) spacer that is bonded as —NHC(O)—.

In another variation, the SP1, SP2 and SP3 groups may be independently selected from:

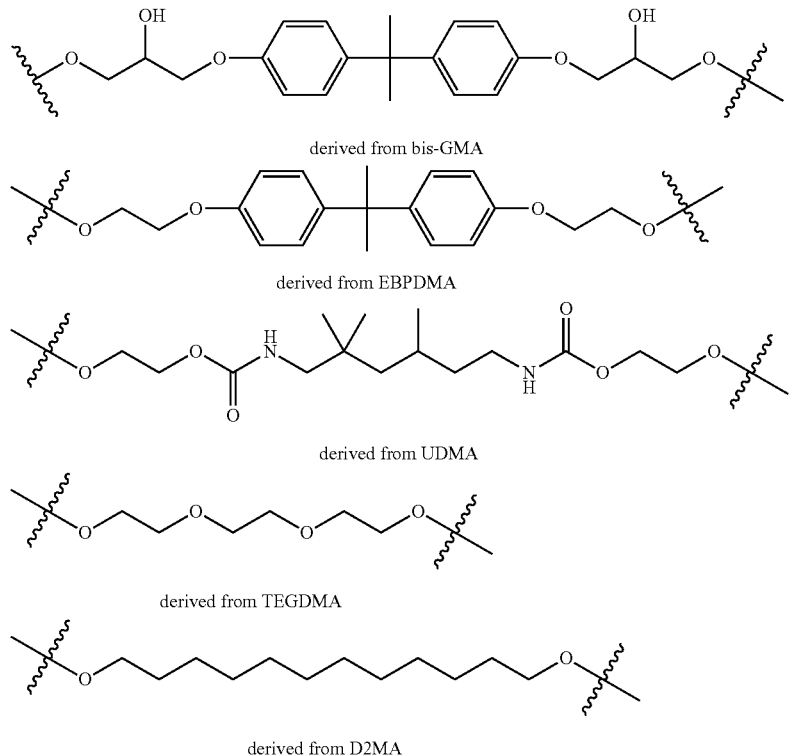

derived from bis-GMA derived from EBPDMA derived from UDMA derived from TEGDMA derived from D2MA In one aspect of the surface binding compound of Formula II, each EG and EG1 is independently selected from the group consisting of a $C_{1-12}$alkyl, $CH_2$=CHC(O)O—, $CH_2$=C($C_{1-3}$alkyl)C(O)O—, $CH_2$=C(phenyl)C(O)O—, isocyanate, epoxy, oxetanyl, styrenyl, vinyl ether, —Ar—(BG)$_a$, phenyl and naphthyl. In one variation, each EG and EG1 is independently selected from the group consisting of a $CH_2$=CHC(O)O— and $CH_2$=C($C_{1-3}$alkyl)C(O)O—. In one variation, each EG and EG1 is independently —N$^+$(CH$_3$)(CH$_2$OH)$_2$, —N$^+$(CH$_3$)$_2$(CH$_2$OH) and —N$^+$(CH$_2$OH)$_3$. In another variation, EG and EG1 are the same.

In one variation, each EG and EG1 is independently selected from the group consisting of $C_1$alkyl, $C_3$alkyl, $C_6$alkyl, $C_{12}$alkyl, $CH_2$=C(CH$_3$)C(O)O—, $CH_2$=C(CH$_2$CH$_3$)C(O)O—, $CH_2$=C($C_{1-3}$alkyl)S(O)$_2$O— and $CH_2$=C(CH$_2$CH$_2$CH$_3$)C(O)O—. In another variation, each EG is independently a $C_6$alkyl, $C_3$alkyl or a $C_1$alkyl or —CH$_3$. In another variation, each EG and EG1 is independently selected from the group consisting of phenyl or naphthyl each optionally substituted by one or two functional groups selected from the group consisting of halo (F, Cl, Br, I), CF$_3$—, CF$_3$O—, CH$_3$O—, —C(O)OH, —C(O)OC$_{1-3}$alkyl, —C(O)CH$_3$, —CN, —NH$_2$, —OH, —NHCH$_3$, —N(CH$_3$)$_2$ and $C_{1-3}$alkyl.

In certain aspects, the EG and EG1, referred to as the head or tail will depend on the nature of the functional group and conditions that allow EG or EG1 to bind first or second, respectively. For example, if EG and EG1 are different, and EG is an acrylate group that bonds to a surface first, the EG may be referred to as the head, and EG1 as the tail. In one aspect, GE and EG1 may independently comprise of a polymerizable group, such as a mono-, di- or poly-acrylates and methacrylates (e.g., methyl acrylate, methyl methacrylate, ethyl(methyl)acrylate, isopropyl(methyl)acrylate, n-hexyl(methyl)acrylate, stearyl(methyl)acrylate, allyl (methyl)acrylate, glycerol di(methyl)acrylate, glycerol tri (methyl)acrylate, ethyleneglycol di(methyl)acrylate, diethyleneglycol di(methyl)acrylate, triethyleneglycol di(methyl) acrylate, 1,3-propanediol diacrylate, 1,3-propanediol dimethacrylate, trimethylolpropane tri(methyl)acrylate, 1,2,4-butanetriol tri(methyl)acrylate and 1,4-cyclohexanediol di(methyl)acrylate.

In another aspect of the surface binding compound, each EG and EG1 is independently selected from the group consisting of imidazolyl, indolyl, —N$^+$R$_1$R$_2$R$_3$, —PO$_4^-$, —N$^+$R$_1$R$_2$R$_3$X$^-$, —PO$_4^-$Y$^+$, -SO$_4^-$Y$^+$, wherein each R$_1$, R$_2$ and R$_3$ is independently H and $C_{1-3}$alkyl, X$^-$ is Cl$^-$, Br$^-$ and I$^-$ and Y$^+$ is H$^+$ or —N$^+$R$_1$R$_2$R$_3$. In one variation, each R, R$_1$, R$_2$ and R$_3$ is independently H and $C_{1-3}$alkyl optionally substituted with —OH, —SH or —NH$_2$.

In another aspect, each of SP1, SP2 and SP3 is a spacer independently selected from the group consisting of —(CH$_2$)$_q$—, —NH(CH$_2$)$_2$NH—, —NHCH$_2$CH$_2$C(O)—, —C(O)NHCH$_2$CH$_2$NH—, —NHCH$_2$C(O)—, —NHC(O)—, —C(O)N—, —NC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$— and —OCH(CH$_2$O—)$_2$—.

In another aspect, each of SP1, SP2 and SP3 is a spacer independently selected from the group consisting of —N$^+$R$_1$R$_2$—, —PO$_4^-$—, —N$^+$R$_1$R$_2$X$^-$—, —PO$_4^-$Y$^+$—, —SO$_4^-$Y$^+$—, —(CH$_2$)$_q$—N$^+$R$_1$R$_2$—, —(CH$_2$)$_q$—PO$_4^-$—, —(CH$_2$)$_q$—N$^+$R$_1$R$_2$—X$^-$—, —(CH$_2$)$_q$—PO$_4^-$Y$^+$— and —O—PO$^-$(O)O—(CH$_2$)$_{2-4}$—N$^+$(R$_1$R$_2$)—.

In yet another aspect of the surface binding compound, each of SP1, SP2 and SP3 is independently selected from —CH$_2$CH$_2$—C(O)NHCH$_2$CH$_2$NH—C(O)NCH$_3$—, —NHC(O)—(CH$_2$CH$_2$O)$_p$—(CH$_2$)$_q$—, —(CH$_2$CH$_2$O)$_p$CH$_2$CH$_2$—C(O)NCH$_3$—(CH$_2$CH$_2$O)$_p$CH$_2$CH$_2$—, —NHCH$_2$CH$_2$C(O)—(CH$_2$)$_q$—PO$_4$$^-$—, —PO$_4$$^-$—(CH$_2$)$_q$—N$^+$R$_1$R$_2$X$^-$—, —(CH$_2$CH$_2$O)$_p$—(CH$_2$)$_q$—PO$_4$$^-$, —N$^+$R$_1$R$_2$X$^-$—(CH$_2$)$_q$—PO$_4$$^-$ and —PO$_4$$^-$—(CH$_2$CH$_2$O)$_p$—N$^+$R$_1$R$_2$X$^-$—.

In another aspect of the surface binding compound, each BG is a bonding group independently selected from the group consisting of —OH, —SiR$_2$OH, —COOH, —SO$_3$H, —P(O)$_3$OH, —CONH$_2$ and —CSNH$_2$. In yet another aspect of the surface binding compound, —SP$_3$— is —CH$_2$— and Ar—(BG)$_a$ is selected from the group consisting of 2,3-dihydroxyphenyl, 3,4-dihydroxyphenyl, 2,3,4-trihydroxyphenyl, 3,4,5-trihydroxyphenyl, 2,3,4,5-tetrahydroxyphenyl, 2,3,4,5,6-pentahydroxyphenyl, 2,3-dicarboxyphenyl, 2,3,4-tricarboxyphenyl, 3,4,5-tricarboxylphenyl, 2,3,4,5-tetracarboxyphenyl, 2,3,4,5,6-pentacarboxyphenyl, 2,3-disiloxyphenyl, 2,3,4-trisiloxyphenyl, 3,4,5-trisiloxyphenyl, 2,3,4,5-tetrasiloxyphenyl and 2,3,4,5,6-pentasiloxyphenyl.

In another aspect of the surface binding compound, each EG and EG1 is independently an aryl group selected from the group consisting of:

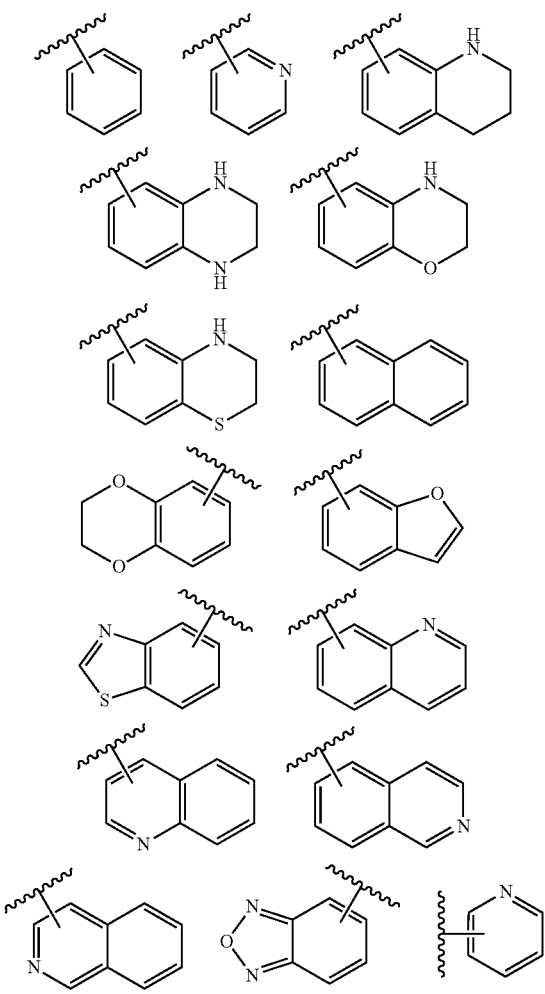

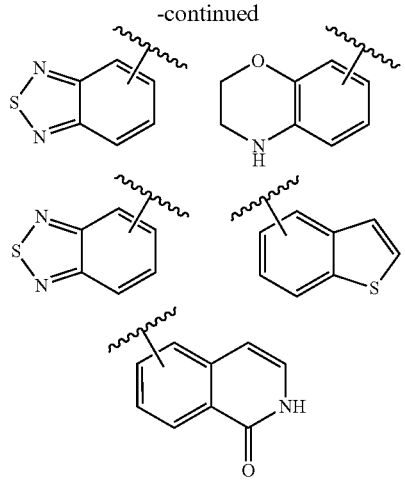

wherein the aryl group is optionally substituted by 1 or 2 substituents selected from halo, CF$_3$—, CF$_3$O—, CH$_3$O—, —C(O)OH, —C(O)OC$_{1-3}$alkyl, —C(O)CH$_3$, —CN, —NH$_2$, —OH, —SiR$_2$OH, —NHCH$_3$—N(CH$_3$)$_2$ and C$_{1-3}$alkyl.

In one variation, each EG and EG1 is independently a cationic, anionic, zwitterionic, polar and non-polar group. In another variation, m is 2 or 3, and the acrylate is a di-acrylate or a tri-acrylate. In one variation, m is 1 and n is 1. In one variation, p is 1, 2, 3, 4, 5 or 6, q is 1, 2, 3, 4, 5 or 6 and r is 1, 2, 3, 4, 5 or 6.

In one particular variation, all of the BG groups on Ar are all adjacent to one another. In one embodiment, each BG is —OH. In one variation, BG is —OH, —COOH and —OH. In another variation, BG is —OH, —SiR$_2$OH or —OH, or a combination thereof. In one variation, R is H. In another variation of the compound of the Formula I and Formula II, the molecular weight is less than 2 kDa, less than 1 kDa or less than 0.5 kDa.

In another embodiment, there is provided a method for forming a coating on a surface of a substrate, the method comprises:
1) washing the surface of the substrate with a first solvent;
2) contacting the surface binding compound of the Formula I, optionally in a second solvent, to the surface:

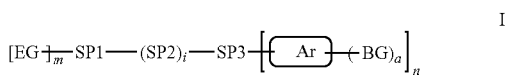

wherein: each a is independently 1, 2, 3, 4 or 5; m is 1, 2 or 3; n is 1, 2 or 3; i is 1, 2 or 3;
each EG is an end group independently selected from the group consisting of a C$_{1-12}$alkyl, CH$_2$=CH—, CH$_2$=C(C$_{1-3}$ alkyl)—, CH$_2$=CHC(O)—, CH$_2$=C(C$_{1-3}$alkyl)C(O)—, CH$_2$=CHC(O)O—, CH$_2$=C(C$_{1-3}$alkyl)C(O)O—, CH$_2$=C(phenyl)C(O)O—, CH$_2$=C(C$_{1-3}$alkyl)S(O)$_n$O—, isocyanate, epoxy, oxetanyl, styrenyl, vinyl ether, (OH)SiR$_2$—, (OH)SiR$_2$(O)—, —Ar—(BG)$_a$, aryl, heteroaryl, —N$^+$R$_1$R$_2$R$_3$, —PO$_4$, —N$^+$R$_1$R$_2$R$_3$X$^-$, —PO$_4$$^-$Y$^+$, —SO$_4$Y$^+$, wherein each R, R$_1$, R$_2$ and R$_3$ is independently H and C$_{1-3}$alkyl, X$^-$ is Cl$^-$, Br$^-$ and I$^-$ and Y$^+$ is H$^+$ or N$^+$R$_1$R$_2$R$_3$;
each of SP1, SP2 and SP3 is a spacer independently selected from the group consisting of —O—, —C(O)—, —S—, —S(O)—, —S(O)$_2$—, —N—, —NH—, —NCH$_3$—, —C—, —CH—, —(CH$_2$)$_q$—, —(CH(OH))$_q$—, —(CH$_2$CH(OH)CH$_2$)$_q$—, —(C(CH$_3$)$_2$)$_q$—, —(CH(CH$_3$))$_q$—, —NH(CH$_2$)$_2$NH—, —OC(O)—, —CO$_2$—, —NHCH$_2$CH$_2$C(O)—, —OCH$_2$CH$_2$C(O)—, —C(O)CH$_2$CH$_2$C(O)—, —C(O)NHCH$_2$CH$_2$NH—, —NHCH$_2$C(O)—, —NHC(O)—, —C(O)N—, —NC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, —OCH(CH$_2$O—)$_2$—, —(CH$_2$)$_q$—N$^+$R$_1$R$_2$—, —(CH$_2$)$_q$—PO$_4^-$—, —N$^+$R$_1$R$_2$—, —PO$_4^-$—, —(CH$_2$)$_q$—N$^+$R$_1$R$_2$—X$^-$—, —(CH$_2$)$_q$—PO$_4^-$Y$^+$—, —N$^+$R$_1$R$_2$—X$^-$—, —PO$_4^-$Y$^+$, —SO$_4^-$Y$^+$—, —O—PO$^-$(O)O—(CH$_2$)$_{2-4}$—N$^+$(R$_1$R$_2$)—, —(AA)$_r$-, aryl, cyclopentanyl, cyclohexanyl, unsubstituted phenylenyl and phenylenyl substituted by 1 or 2 substituents selected from the group consisting of halo, CF$_3$—, CF$_3$O—, CH$_3$O—, —C(O)OH, —C(O)OC$_{1-3}$alkyl, —C(O)CH$_3$, —CN, —NH$_2$, —OH, —NHCH$_3$, —N(CH$_3$)$_2$ and C$_{1-3}$alkyl, wherein each AA is independently an amino acid, p is 1-6, q is 1-6 and r is 1-6;

Ar is an aryl or heteroaryl group;

each BG is a bonding group independently selected from the group consisting of —OH, —SiR$_2$OH, —COOH, —SO$_3$H, —P(O)$_3$OH, —CONH$_2$, —CSNH$_2$, —CF$_3$, —CF$_2$CF$_3$, —OCF$_3$ and —OCF$_2$CF$_3$;

provided that:

a) at least one of SP1, SP2 and SP3 is a spacer selected from the group consisting of A, A1, A2, B, C, D, E, F, G, H, H-1, I, I-1, J, J-1, K, K-1, L, L-1, M, M-1, N, O, P, Q and R:

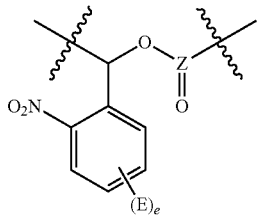

A

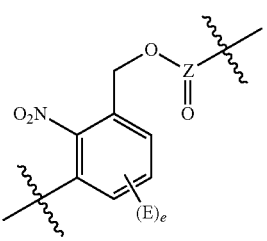

B

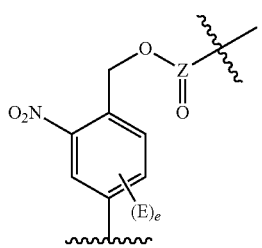

C

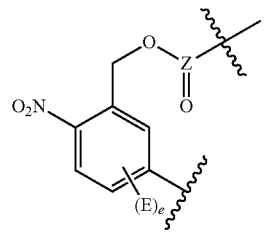

D

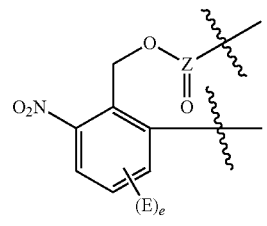

E

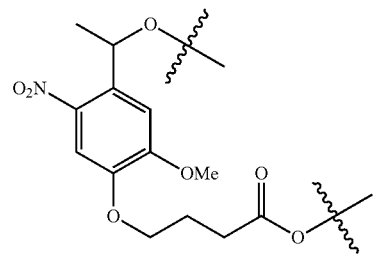

A1

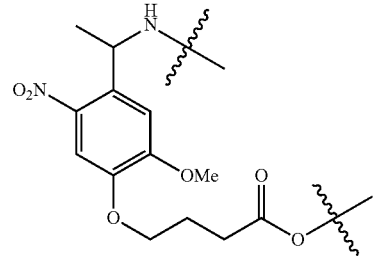

A2

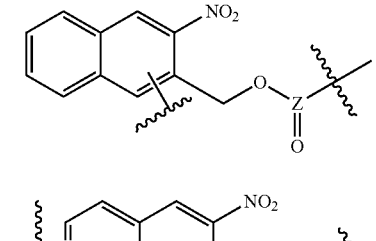

F

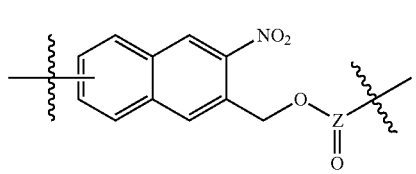

G

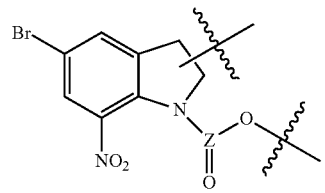

H

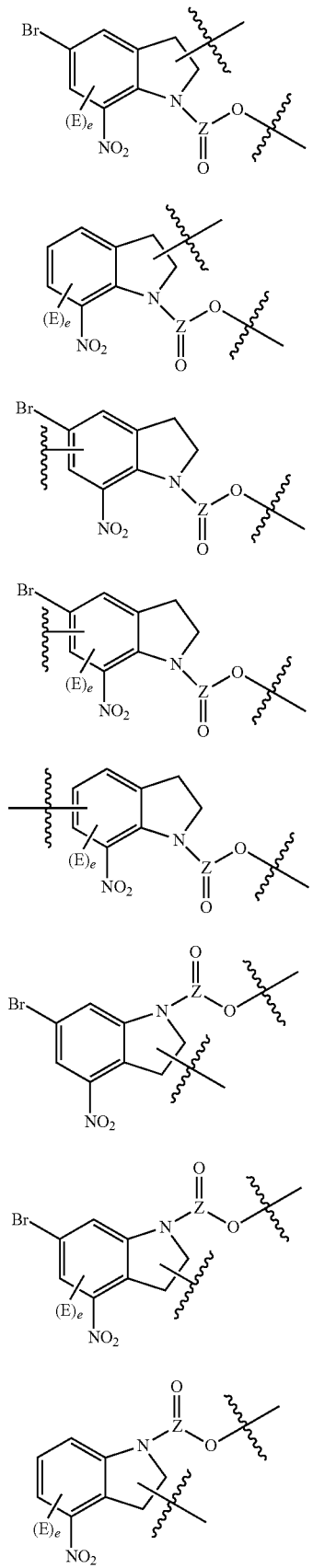
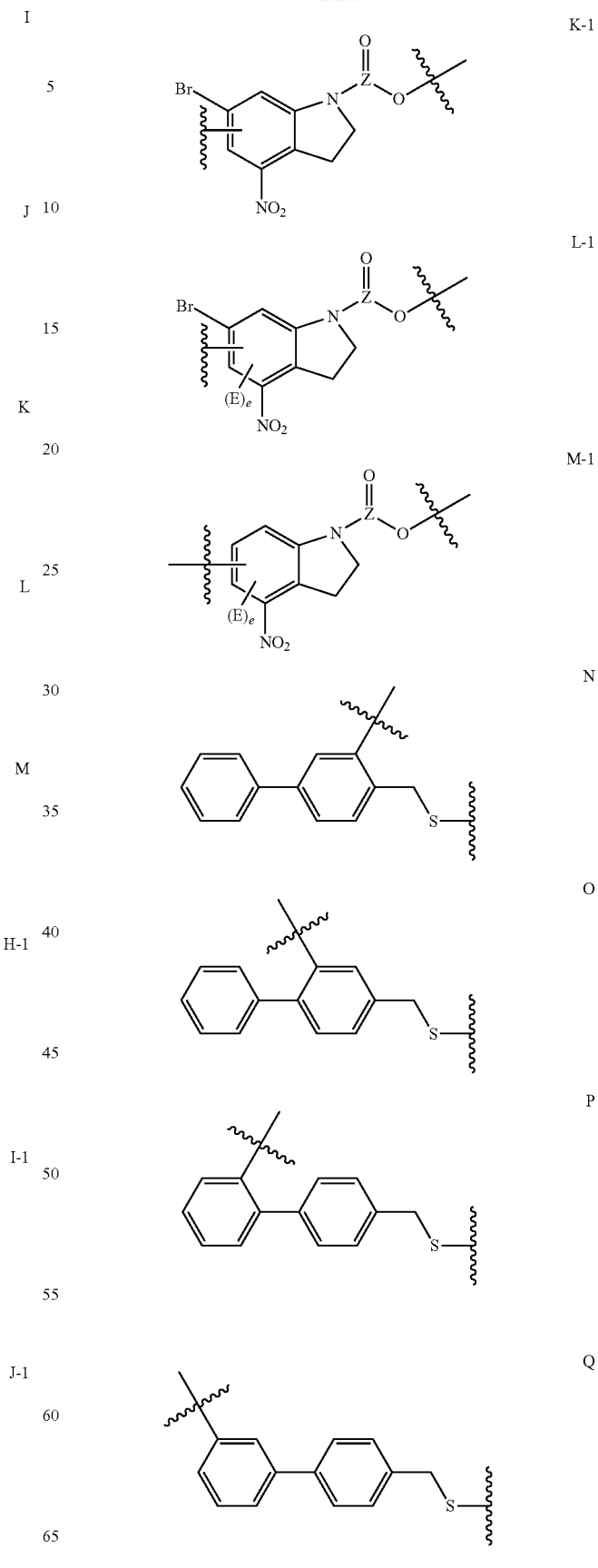

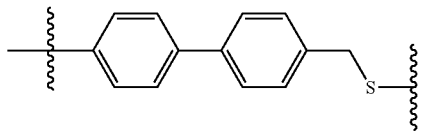
wherein: Z is selected from the group consisting of C, S, S(O), P(OH) and P(OR);
each E is independently selected from the group consisting of halo, CF$_3$—, CF$_3$O—, HO— and CH$_3$O—; and e is 0, 1, 2 or 3; and
b) when one of SP1, SP2 and SP3 is not a spacer selected from the group consisting of A, B, C, D, E, F, G, H, H-1, I, I-1, J, J-1, K, K-1, L, L-1, M, M-1, N, O, P, Q and R, then each of the group
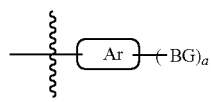
is independently selected from the group consisting of:
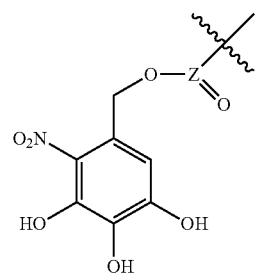
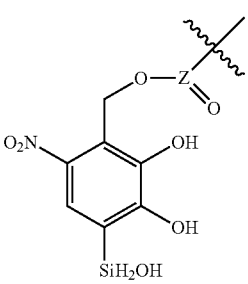
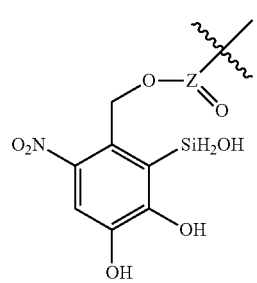
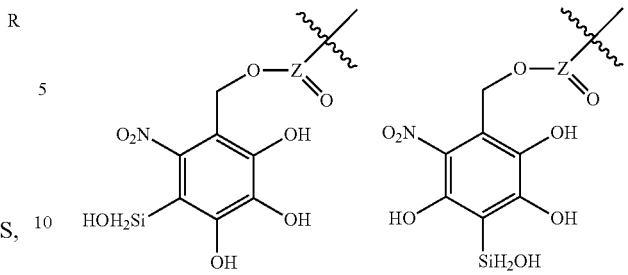
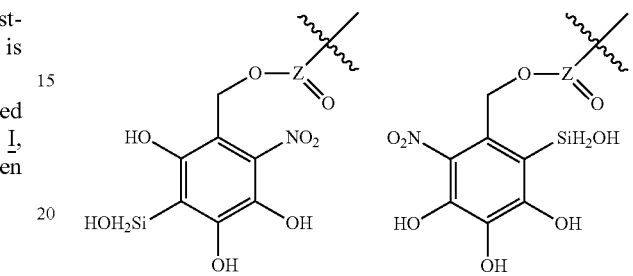
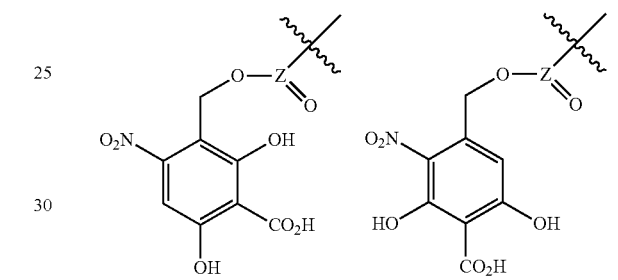
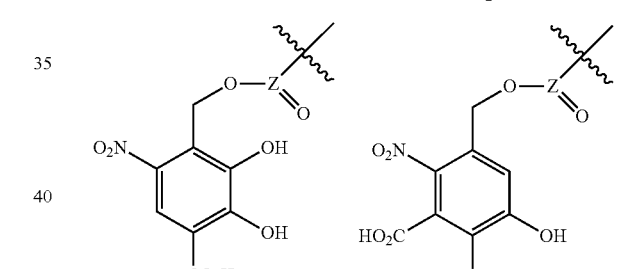
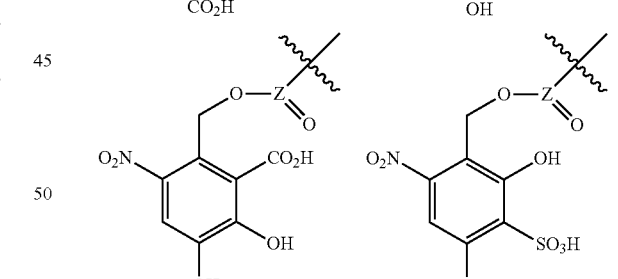
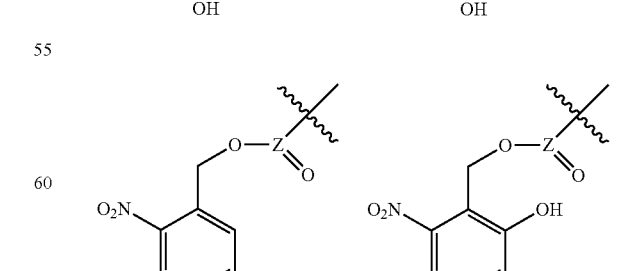

-continued
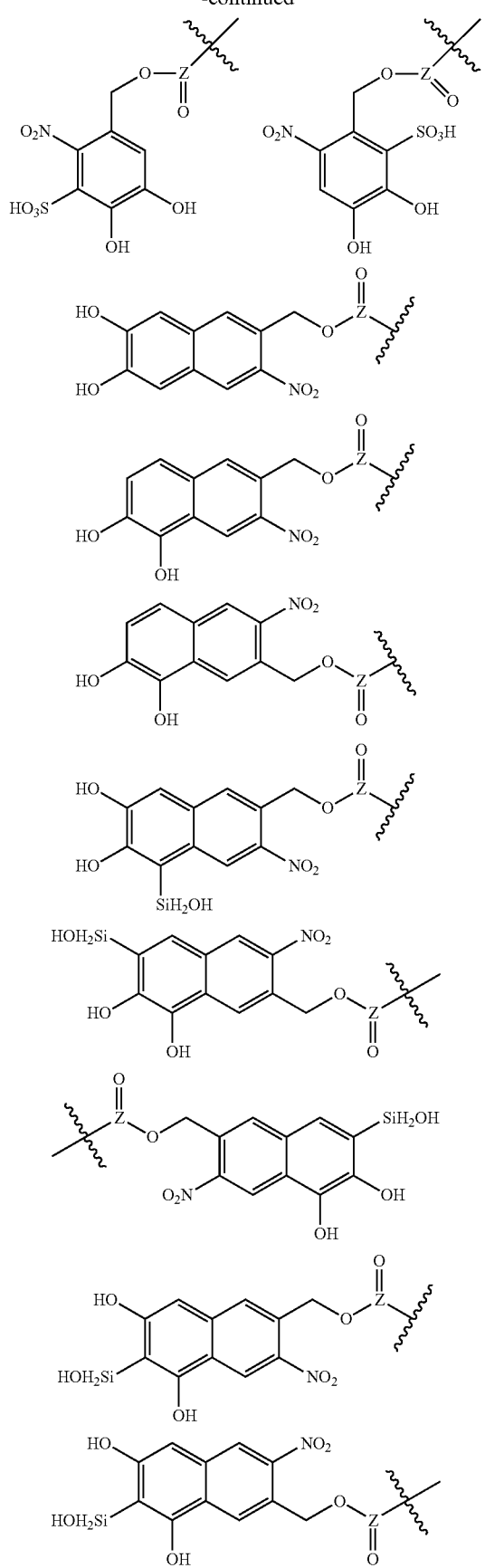
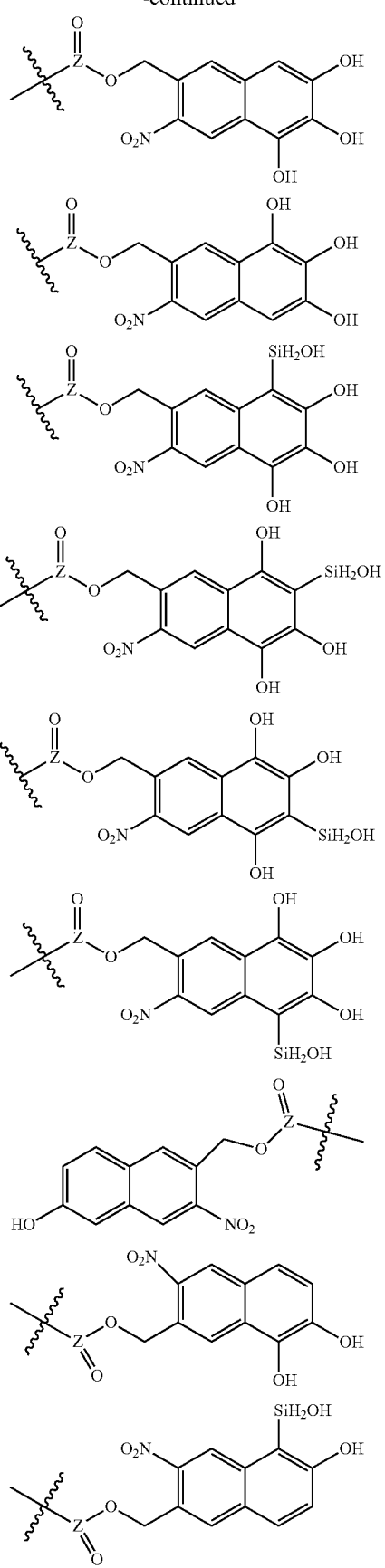

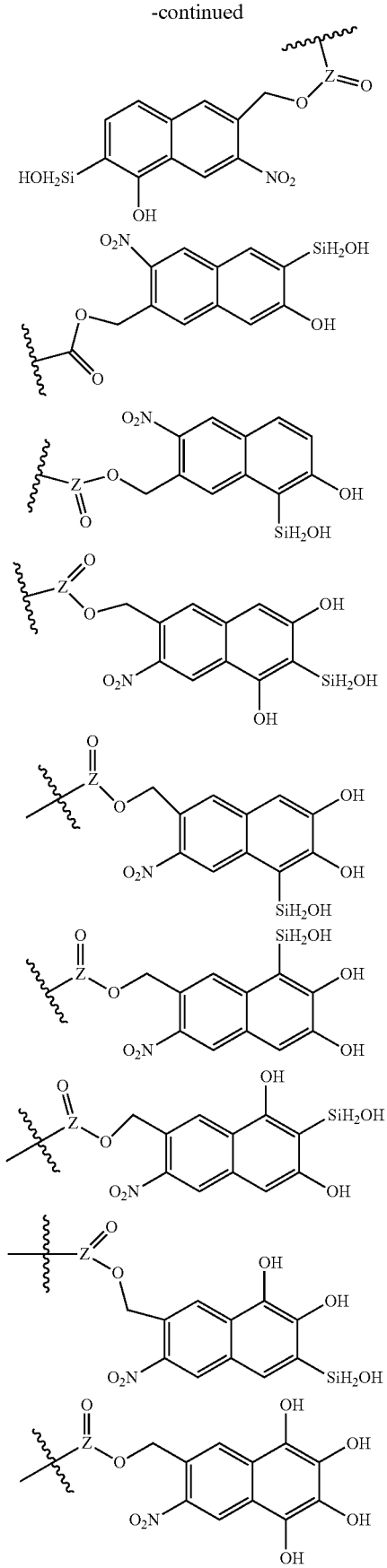
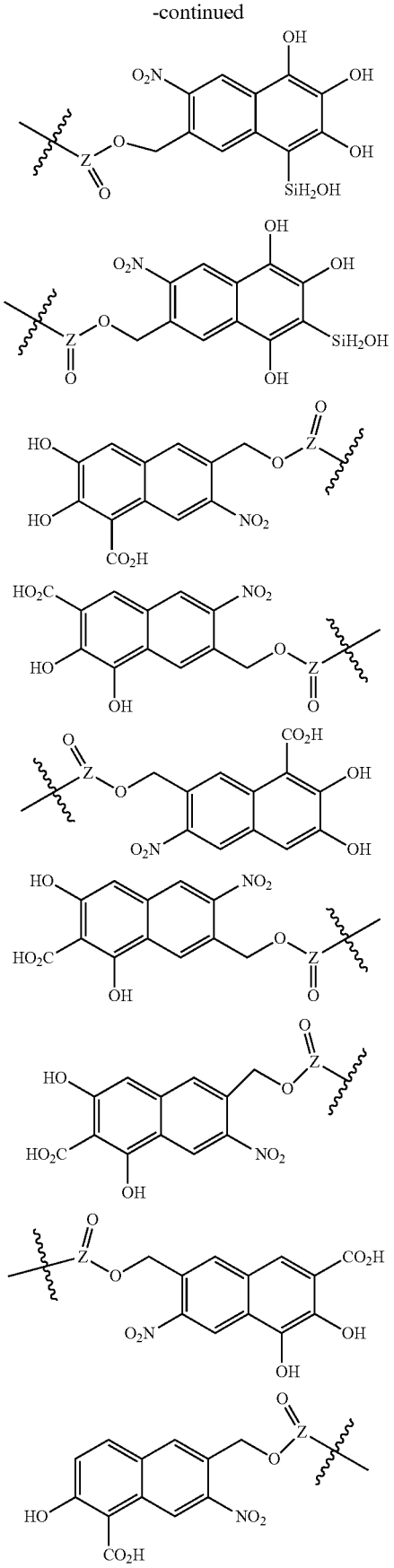

-continued

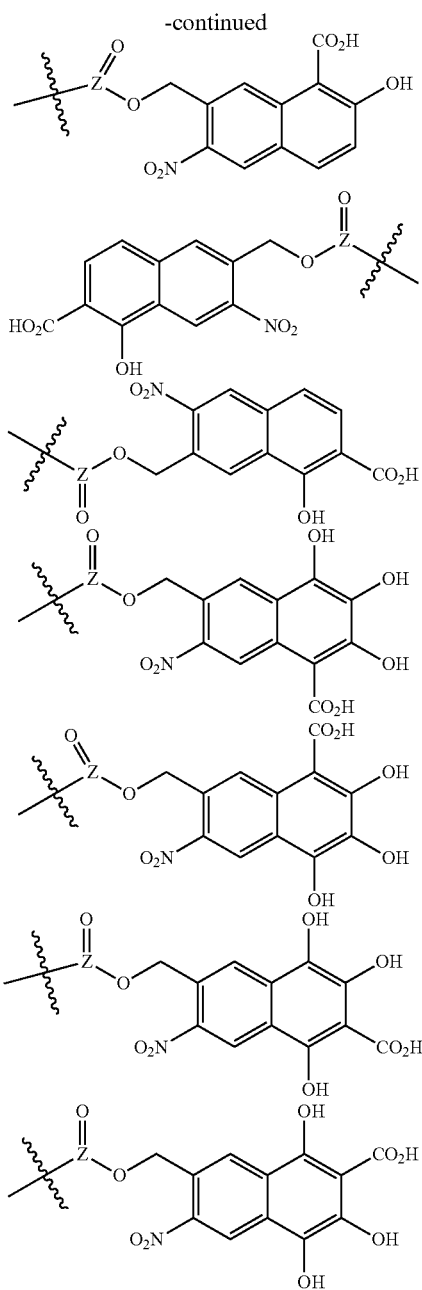

wherein: each Z is selected from the group consisting of C, S, S(O), P(OH) and P(OR);

3) for a period of time for the compound of the Formula I to form a layer on the surface of the substrate; and optionally, 4) washing the excess compound of the Formula I from the surface of the substrate with a sufficient amount of a third solvent to remove excess compound from the surface.

In one variation of the method, the compound of the Formula I or II forms a SAM. In one variation of the method, the compound used is a compound of the Formula I, or a mixture of the compound of the Formula I to provide the desired improved mechanical or electronic properties of the substrate. In another variation, the first solvent is water, an organic solvent or a mixture of water and the organic solvent. In a particular variation, the organic solvent is selected from the group consisting of methanol, ethanol, propanol, isopropanol, acetone, methylethyl ketone (2-butanone), hexanes, cyclohexane, heptane, toluene, xylenes, THF, Me-THF and N-methylpyrrolidone, and mixtures thereof. In another variation, the first, second and third solvents are the same or are different, and are selected from the group consisting of water, methanol, ethanol, a mixture of water and methanol, a mixture of water and ethanol or a combination thereof. In another variation, the first solvent is different than the second and the third solvent.

In another aspect of the method, each EG and EG1 is independently selected from the group consisting of a $C_{1-2}$alkyl, $CH_2$=CHC(O)O—, $CH_2$=C($C_{1-3}$alkyl)C(O)O—, $CH_2$=C(phenyl)C(O)O—, isocyanate, epoxy, oxetanyl, styrenyl, vinyl ether, —Ar—(BG)$_a$, phenyl and naphthyl.

In another aspect of the method, each EG and EG1 is independently selected from the group consisting of imidazolyl, indolyl, —N$^+$R$_1$R$_2$R$_3$, —PO$_4^-$, —N$^+$R$_1$R$_2$R$_3$X$^-$, —PO$_4^-$Y$^+$, —SO$_4^-$Y$^+$, wherein each R$_1$, R$_2$ and R$_3$ is independently H and $C_{1-3}$alkyl, X$^-$ is Cl$^-$, Br$^-$ and I$^-$ and Y$^+$ is H$^+$ or —N$^+$R$_1$R$_2$R$_3$. In one variation, the imidazolyl is an imidazolinium, and the indolyl is an indolinium and the counterion is a halide, sulfonate or phosphate.

In yet another aspect of the method, each of SP1, SP2 and SP3 is a spacer independently selected from the group consisting of —(CH$_2$)$_q$—, —NH(CH$_2$)$_2$NH—, —NHCH$_2$CH$_2$C(O)—, —C(O)NHCH$_2$CH$_2$NH—, —NHCH$_2$C(O)—, —NHC(O)—, —C(O)N—, —NC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$— and —OCH(CH$_2$O)$_2$—. In yet another aspect of the method, each of SP1, SP2 and SP3 is a spacer independently selected from the group consisting of —N$^+$R$_1$R$_2$—, —PO$_4^-$—, —N$^+$R$_1$R$_2$X$^-$—, —PO$_4^-$Y$^+$—, —SO$_4^-$Y$^+$—, —(CH$_2$)$_q$—N$^+$R$_1$R$^2$—, —(CH$_2$)$_q$—PO$_4^-$—, —(CH$_2$)$_q$—N$^+$R$_1$R$_2$—X$^-$—, —(CH$_2$)$_q$—PO$_4^-$Y$^-$— and —O—PO$^-$(O)O—(CH$_2$)$_{2-4}$—N$^+$(R$_1$R$_2$)—.

In another aspect of the method, each SP1, SP2 and SP3 is a spacer independently selected from the group consisting of —CH$_2$CH$_2$—C(O)NHCH$_2$CH$_2$NH—C(O)NCH$_3$—, —NHC(O)—(CH$_2$CH$_2$O)$_p$—(CH$_2$)$_q$—, —(CH$_2$CH$_2$O)$_p$CH$_2$CH$_2$—C(O)NCH$_3$—(CH$_2$CH$_2$O)$_p$CH$_2$CH$_2$—, —NHCH$_2$CH$_2$C(O)—(CH$_2$)$_q$—PO$_4^-$—, —PO$_4^-$—(CH$_2$)$_q$—N$^+$R$_1$R$_2$X$^-$—, —(CH$_2$CH$_2$O)$_p$—(CH$_2$)$_q$—PO$_4^-$—, —N$^+$R$_1$R$_2$X$^-$—(CH$_2$)$_q$—PO$_4^-$ and —PO$_4^-$—(CH$_2$CH$_2$O)$_p$—N$^+$R$_1$R$_2$X$^-$—.

In another aspect of the method, Ar is an aryl group selected from:

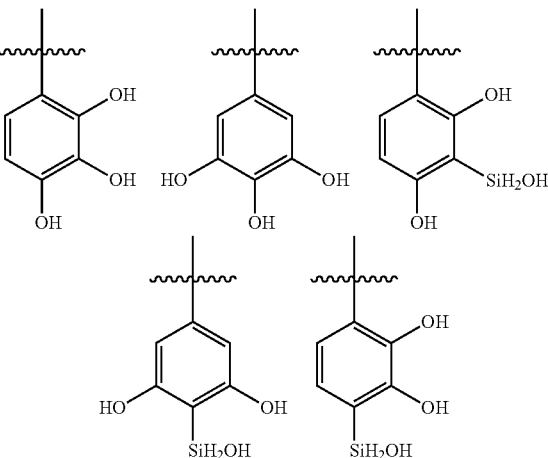

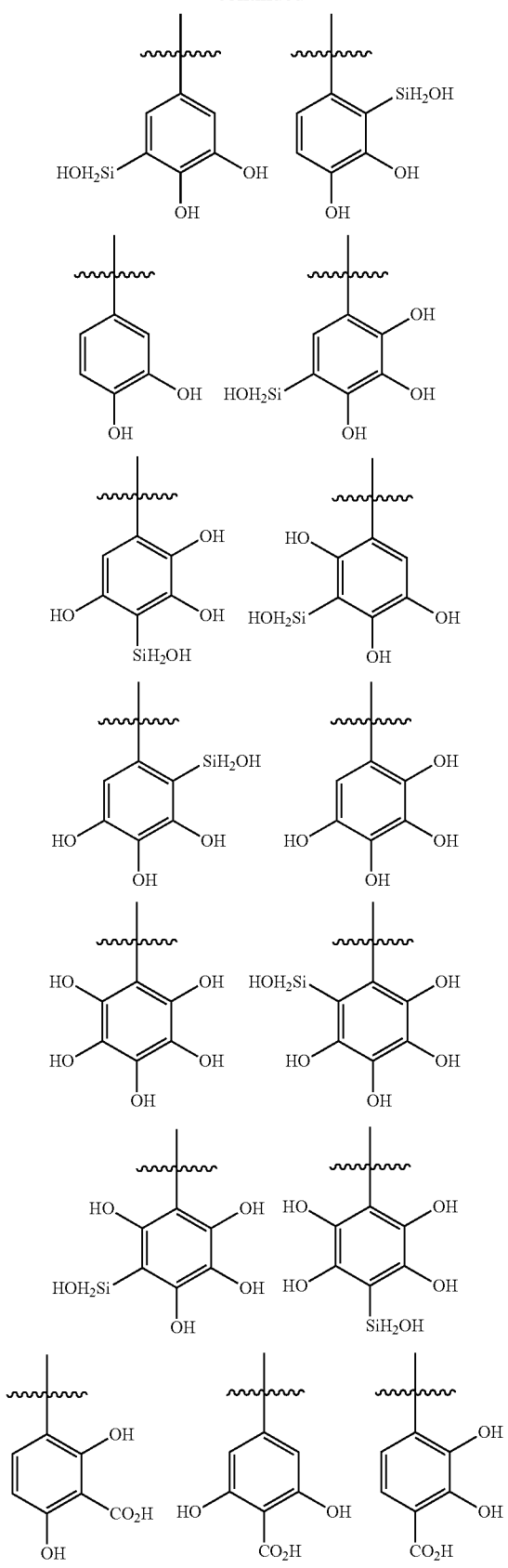
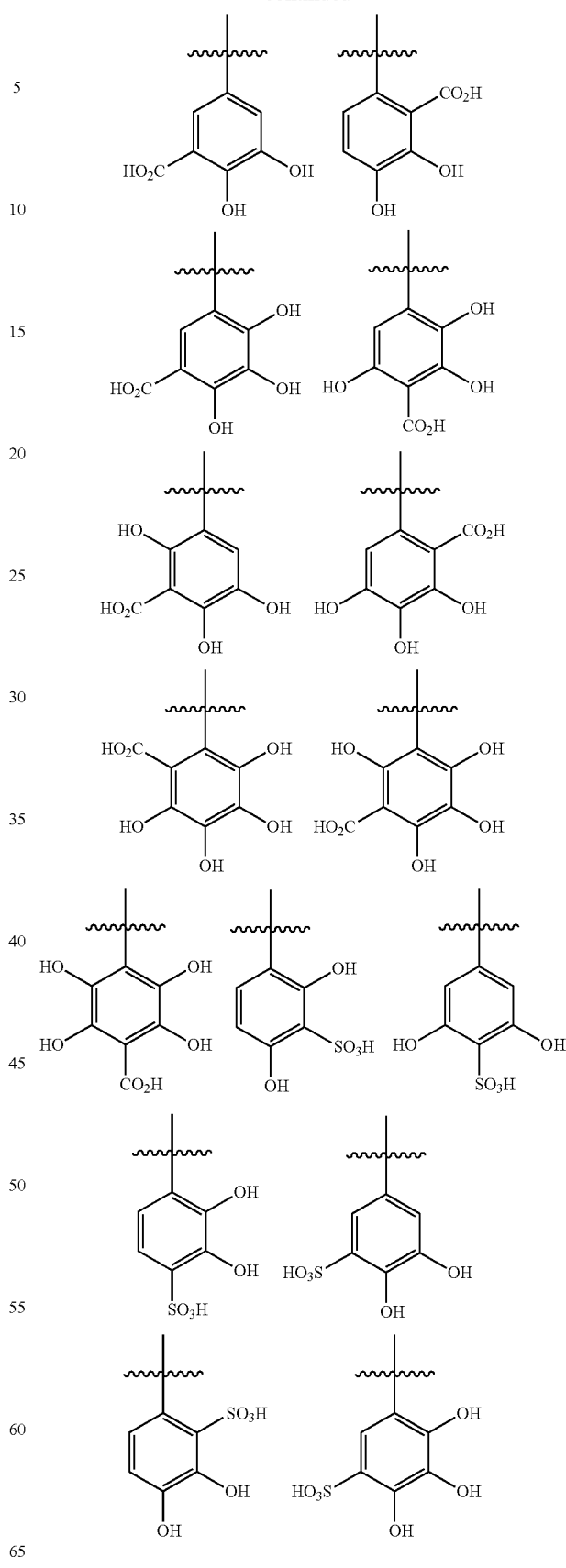

-continued

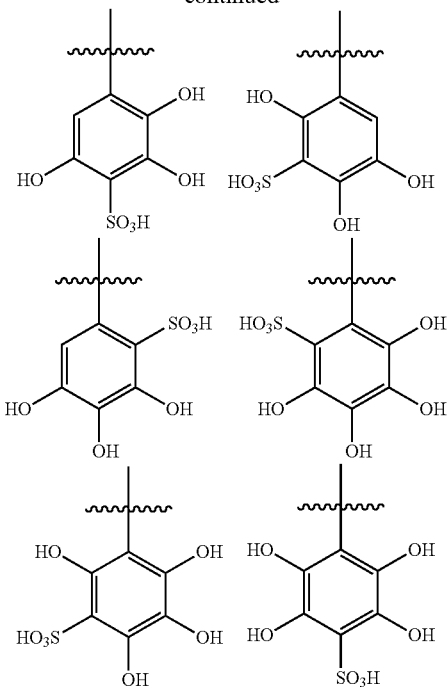

In another aspect of the method, each BG is a bonding group independently selected from the group consisting of —OH, —SiR$_2$OH, —COOH, —SO$_3$H, —P(O)$_3$OH, —CONH$_2$ and —CSNH$_2$.

In another aspect of the method, —SP3— is —CH$_2$— and Ar—(BG)$_a$ is selected from the group consisting of 2,3-dihydroxyphenyl, 3,4-dihydroxyphenyl, 2,3,4-trihydroxyphenyl, 3,4,5-trihydroxyphenyl, 2,3,4,5-tetrahydroxyphenyl, 2,3,4,5,6-pentahydroxyphenyl, 2,3-dicarboxyphenyl, 2,3,4-tricarboxyphenyl, 3,4,5-tricarboxylphenyl, 2,3,4,5-tetracarboxyphenyl, 2,3,4,5,6-pentacarboxyphenyl, 2,3-disiloxyphenyl, 2,3,4-trisiloxyphenyl, 3,4,5-trisiloxyphenyl, 2,3,4,5-tetrasiloxyphenyl and 2,3,4,5,6-pentasiloxyphenyl.

In another aspect of the method, the coating is formed by a self-assembly of the compound of the Formula I or Formula II onto the surface. In yet another aspect of the method, the self-assembled layer is about 0.1 nm to 20 nm, about 0.1 to 15 nm, 0.1 to 10 nm or about 0.1 to 5 nm.

In another aspect of the method, the coating is a material selected from an adhesive or a primer. In another aspect of the method, the substrate is selected from the group consisting of an oxide, a metal, a metal oxide and a mineral. In another aspect of the method, the substrate is selected from the group consisting of mica, silicon, glass, calcium, enamel, bone, steel, tooth enamel, tooth dentin, hydroxylapatite, kaolin and zirconia. In another aspect, the metal, metal oxide or oxide is selected from the group consisting of silicate mineral, silica, kaolin, zirconia, aluminum, copper, chrome, chrome-cobalt, titanium, zinc, tin, indium-tin and calcium oxide.

In yet another aspect of the method, the adhesive is formed by contacting the tail end of the self-assembled layer comprising the -EG groups of the substrate that is the first substrate, with the tail end of a second substrate comprising a surface binding compound of the Formula I, whereby the tail end of the compound of the Formula I of the first substrate binds with the tail end of the compound of the Formula I of the second substrate. For the compound of the Formula II, for example, the adhesive is formed by contacting one end (or the head) of the self-assembled layer comprising the EG or EG1 groups of the substrate that is the first substrate, with the other end (the EG or EG1 groups) of a second substrate comprising a surface binding compound of the Formula II, whereby the EG end of the compound of the Formula II of the first substrate binds with the EG1 end of the compound of the Formula II of the second substrate. In yet another aspect of the method, the adhesive forms an adhesive layer for dental application, medical implants and orthopedic application. In another aspect, the metal oxide is selected from the group consisting of aluminum oxide, copper oxide, chrome, chrome-cobalt, titanium oxide, zinc oxide, tin oxide and indium-tin-oxide (ITO).

In another aspect of the above method, the substrate is selected from the group consisting of polytetrafluoroethylene (PTFE), silicon, silicon wafer, polyvinyl fluoride (PVF), natural rubber (CR), polypropylene (PP), polyethylene (PE), polymethyl methacrylate, acryl (PMMA), epoxy (EP), polyoxymethylene, acetal (POM), polystyrene (PS), polyvinyl chloride (PVC), vinylidene chloride (VC), polyester (PET), polyimide (PI), polyarylsulfone (PAS), phenolic resin, polyurethane (PUR), polyimide 6 (PA 6), polycarbonate (PC), lead (Pb), aluminum (Al), copper (Cu), chromium (Cr), iron (Fe) and stainless steel (SS).

In another aspect, there is provided a method for bonding a dental object on a surface of a tooth comprising: a) preparing the tooth surface for bonding; b) applying a photocleavable adhesive or a mixture of adhesives to the tooth surface; c) contacting the photocleavable adhesive or mixture of adhesives with a dental adhesive to form a bonding mixture; d) contacting the dental object with the combined adhesive mixture to secure the dental object onto the surface of the tooth; and e) applying a source of light to the combined adhesive mixture for a sufficient period of time to cure the combined adhesive mixture and secure the dental object onto the tooth surface; wherein the photocleavable adhesive or mixture of adhesives comprise of the surface binding compound or mixtures thereof, as described herein, or a compound of the formulae 89 to 96, or mixtures thereof. In another aspect, the method further comprises f) allowing the dental object to remain on the tooth surface for a sufficient period of time to bond to the tooth surface and remain for a desired purpose; and g) exposing the combined adhesive mixture with a UV radiation or IR radiation for a sufficient period of time, optionally with physical agitation of the dental object and or the tooth for a sufficient period of time, to debond or remove the dental object from the surface.

In another aspect of the method, the coating is formed by a self-assembly of the compound of the Formula I or Formula II onto the surface. In one variation, the self-assembled layer is a self-assembled monolayer (SAM). In one variation, the self-assembled layer forms at less than 40° C., less than 30° C. or at about RT. In another variation, the self-assembled monolayer forms in less than about 60 min., less than 45 min., less than 30 min. or less than about 15 min.

In another aspect of the method, the coating is a material selected from an adhesive or a primer. In yet another aspect of the above method, the substrate is selected from the group consisting of an oxide, a metal, a metal oxide and a mineral. In another aspect of the method, the substrate is selected from the group consisting of mica, silicon, glass, calcium, enamel, bone, steel, tooth enamel, tooth dentin, hydroxylapatite, kaolin and zirconia. In another aspect of the method, the metal, metal oxide or oxide is selected from the group consisting of silicate mineral, silica, kaolin, zirconia, aluminum, copper, chrome, chrome-cobalt, titanium, zinc, tin, indium-tin and calcium oxide.

In another embodiment, there is provided a method for bonding a dental object on a surface of a tooth comprising: a) preparing the tooth surface for bonding; b) applying a photocleavable adhesive or a mixture of adhesives to the tooth surface; c) contacting the photocleavable adhesive or mixture of adhesives with a dental adhesive to form a bonding mixture; d) contacting the dental object with the combined adhesive mixture to secure the dental object onto the surface of the tooth; and e) applying a source of light to the combined adhesive mixture for a sufficient period of time to cure the combined adhesive mixture and secure the dental object onto the tooth surface; wherein the photocleavable adhesive or mixture of adhesives comprise of the surface binding compound or mixtures thereof, as disclosed herein. In one variation, the mixture of adhesives comprises of photocleavable adhesive, a mixture of photocleavable adhesives, and a mixture of photocleavable and non-photocleavable adhesives. In one variation, the photocleavable adhesive is selected from a compound of the formulae 1 to 45 or a mixture thereof. In one variation, the photocleavable adhesive is selected from the compound of the formulae 89 to 96, or a mixture thereof. In another variation, the non-photocleavable adhesive comprise of the compound of the formulae 63 to 89, or mixtures thereof. In one variation, the source of light for curing the bonding mixture is visible light, such as an LED blue light. In another variation, the dental adhesive is a resin cement or a commercially available dental adhesive or dental cement. In another variation, the dental adhesive is Bis-GMA and TEGDMA, and DMAEMA and an initiator, such as CQ. In another aspect, the method further comprises: f) allowing the dental object to remain on the tooth surface for a sufficient period of time to bond to the tooth surface and remain for a desired purpose; and g) exposing the combined adhesive mixture with a UV radiation or IR radiation for a sufficient period of time, optionally with physical agitation of the dental object and/or the tooth for a sufficient period of time, to debond or remove the dental object from the surface.

In another aspect of the method, the adhesive is formed by contacting the tail end of the self-assembled layer comprising the -EG groups of the substrate that is the first substrate, with the tail end of a second substrate comprising a surface binding compound of the Formula I, whereby the tail end of the compound of the Formula I of the first substrate binds with the tail end of the compound of the Formula I of the second substrate. In one variation, the compound of the Formula I in the first substrate is the same or different than the compound of the Formula I in the second substrate. Similarly, in one variation, the compound of the Formula II in the first substrate is the same or different than the compound of the Formula II in the second substrate. In another variation, the head end of the compound of the Formula I, or the EG or EG1 group of the compound of the Formula II, binds with the surface of the substrate via hydrogen bonds, chelation, metal-oxygen coordination bond or via a covalent bond.

In another aspect of the method, the adhesive forms an adhesive layer for dental application, medical implants and orthopedic application. In one variation, the adhesive layer may be used as an enamel adhesive or cement or a bone adhesive or cement. For dental applications, the adhesive layer may be used as a filling, a general adhesive, a cavity liner, a dental cement, a coating composition with or without filler, a root canal filler or sealant with or without filler or a combination thereof. In one variation the adhesive layer may be a self-adhesive composition or a photo-curable composition. In one variation, the compounds of Formula I and II may be cross-linking agents.

Methods of forming a SAM coating on a surface of a substrate are known in the art. The SAM or SAM coating that forms the EG group or the —Ar—BG group may include organosilanes or other silane molecules. In one variation, the SAM coating is a chlorosilane, such as a trichlorosilane or a methoxysilane. Tricholorosilanes of a SAM as provided herein may be selected from a n-decyl-trichlorosilane (DTS), a n-dodecyl-trichlorosilane, a perfluorodecyl-trichlorosilane (FDTS) or a n-octadecyltrichlorosilane. As provided herein, a SAM may include a dimethylaminosilanes and alklysilanes, and alkyltricholorosilane or alkyltrimethoxysilane. In one variation, the SAM comprises siloxanes such as hexamethyldisilazane (HMDS).

In one variation, the coating is a self-assembled layer of the compound. In another variation, the surface is a gate dielectric surface for electronic devices, such as an organic field-effect transistor. In another variation, the self-assembled monolayer is ordered and defect-free. In one aspect of the SAMs of the present application, at least 30%, 40%, 50%, 60%, 70%, 80%, 90% or more than 95% of the compounds that adsorb to the surface bond to the surface of the substrate. In another variation, the high bonding layer provides well-defined, uniform and reproducible layers, such as monolayers, that are bonded to the surface of the substrate. The substantially ordered and defect-free layers may be characterized and confirmed using Atomic Force Microscope (AFM), X-Ray Scattering or a combination thereof, as known in the art.

In another variation of the method, the self-assembled layer is a surface modifier used for anode binders, electro circuits, field effect transistors (FET; with range value of 20-50 $cm^2V^{-1}s^{-1}$), semiconductors, nanosensing devices, organic solar cells, opto-electronic devices, hetero junctions and electron tunneling junctions. In one variation of the above, the self-assembled layer is a self-assembled monolayer (SAM).

In another variation, the compound forms a SAM in less than about 60 minutes, less than 30 minutes, less than 10 minutes, less than 5 minutes, less than about 2 minutes or less than about 1 minute after contacting with the surface of the substrate. In one variation of the method, the compound forms a substantially smooth, uniform and defect-free SAM.

In one variation of the method, the SAM is a surface modifier that produces low contact angles (θ) of less than 20°, less than 15°, than 13° or less than 11° for a chlorobenzene droplet. In another variation, the SAM surface modifiers are omniphilic with <30° contact angle for water droplets. In one variation, the SAM forms a monolayer of about 0.1 nm to 50 nm, 0.1 nm to 40 nm, 0.1 nm to 30 nm, 0.1 nm to 20 nm or about 0.1 nm to 10 nm. In another variation, the SAM forms a monolayer of less than about 5 nm, less than 4 nm, less than 3 nm or less than 2 nm.

In another variation of the method, the method further comprises: providing a layer of organic semiconducting material over the layer of the self-assembled layer or SAM. In according to one variation of the above described methods, the method provides an improved organic thin-film transistor or other similar electronic devices. In one aspect of the method, the self-assembled layer may comprise a self-assembled monolayer. The self-assembled layer may comprise a polymer layer. In one variation of the method, the self-assembled layer may have a surface region which is hydrophobic and/or oleophillic.

In one variation of the above adhesive, the bonding strength or the shear fracture strength is at least 15 kT, greater than 20 kT, greater than 25 kT, greater than 30 kT, greater than 35 kT, greater than 40 kT, greater than 45 kT or greater than 50 kT. In one variation of the method, the adhesion is at least 30 mJ m$^{-2}$, 35 mJ m$^{-2}$, 40 mJ m$^{-2}$ or at least 45 mJ m$^{-2}$.

In some embodiments, the compound of Formula I or Formula II may be used as a primer or a coating. As disclosed herein, the compound of Formula I or Formula II provides strong adhesion/adsorption and retains the ability to interact or bond with a secondary layer. The compound may adhere to a variety of surfaces and undergo self-assembly to form a thin primer/coating/glue/adhesive layer. In some embodiments, the primer/coating/glue/adhesive layer has a thickness from between 0.5 to 50 nm.

In some embodiments as disclosed herein, the compound of Formula I or Formula II can be applied onto mineral or metal oxide surfaces, such as mica, silicon wafer, glass, bone, tooth enamel, tooth dentin, medical/dental implant, silica, kaolin, zirconia, aluminum, copper, chrome, chrome-cobalt, calcium, aluminum oxide, copper oxide, silica oxide, titanium oxide, zinc oxide, calcium oxide, tin oxide, indium-tin oxide or hydroxylapatite.

In some embodiments, the deposited layer of the compound of Formula I or Formula II may be treated with an oxidizing agent, such as periodate. In other embodiments, the layer may be treated with a base. Based on the hydroxylphenyl or phenolic groups that are similar to the molecule DOPA (3,4-dihydroxyphenylalanine), at low pH, the phenolic groups are structurally favored over the corresponding keto- or quinone-like structures (or tautomers), and accordingly, the phenolic forms provide higher bonding forces with the substrate. Accordingly, the keto- or quinone-like forms of the compound and their associated bonding forces are provided at higher pH. Under substantially neutral pH conditions, a strong adhesive interaction of the compound to the substrate may be associated with the interaction of the surfaces with the unoxidized phenolic groups, and the weaker adhesive interaction of the compounds with the surface may be associated with the corresponding oxidized phenolic groups to the oxo- or quinone-type functionality. Accordingly, the surface bound materials may be treated with an oxidizing agent, or may be treated with a base to adjust or modify the binding strength of the coating to the substrate. In some embodiments, deposition of the compound upon the substrate, may be performed prior to treatment with an oxidizing agent. It is known that compounds possessing phenolic groups may be crosslinked under oxidative conditions to afford mixtures of polymeric phenols. Under conditions of neutral pH, or high pH, an adhesive interaction between the unoxidized phenolic groups of the compound and the substrate results. Accordingly, the strong adhesive interaction between the phenolic compound and the substrate, will organize the compound along the interface of the substrate. Once the substrate is deposited, oxidation may crosslink the phenolic groups of the compound along the interface between compound and substrate. Oxidation of the compound in solution, prior to deposition on substrate, may crosslink the phenolic groups differently, as a consequence of different chemical environments around the phenolic groups. The resulting properties of the adhesive layer may be modified or adjusted by oxidizing the compound before or after depositing upon the substrate.

In some embodiments, the compound of Formula I or Formula II may be used as a dental/bone adhesive, surface primers for dental/medical implants, surface primers for mineral fillers used for polymer composites including dental and bone cements/adhesives/composites, or electronic devices.

In some embodiments, the deposited layers of the present application comprise a mixture of anionic and cationic groups, such as an anionic or cationic terminal group, provide anti-adsorption properties toward certain compositions, such as proteins, and accordingly, provide effective anti-fouling surfaces. As disclosed herein, the compounds comprise, for example, a phosphate group and an ammonium salt, that form zwitterionic groups that are highly effective as anti-fouling compositions and surfaces. In addition, the coating has the ability to resist the adsorption of bacteria, barnacle cypris larvae and algal zoospores, and accordingly prevent marine fouling of the surfaces. In addition, the surface materials are also effective as antibacterial surfaces for different medical applications.

As disclosed herein, the anionic and cationic functional groups may be incorporated at an internal position in the compound of the Formula I or Formula II, incorporated at an internal position and at the terminal position, and various combinations thereof. According to one embodiment, the surface coating provides highly effective anti-fouling surfaces or prevents biofoulants from attaching to the surfaces, and accordingly, provides an effective grafting method that provides substrates with better mechanical and chemical robustness and significantly better long term stability of the substrates.

In addition to the exemplary embodiments, aspects and variations described above, further embodiments, aspects and variations will become apparent by reference to the drawings and figures and by examination of the following descriptions.

DETAILED DESCRIPTION OF THE INVENTION

Definitions:

Unless specifically noted otherwise herein, the definitions of the terms used are standard definitions used in the art of organic synthesis and pharmaceutical sciences. Exemplary embodiments, aspects and variations are illustrated in the figures, and it is intended that the embodiments, aspects and variations, and the figures disclosed herein are to be considered illustrative and not limiting. The entire disclosures of all documents cited throughout this application are incorporated herein by reference.

An "alkyl" group is a straight, branched, saturated or unsaturated, aliphatic group having a chain of carbon atoms, optionally with oxygen, nitrogen or sulfur atoms inserted between the carbon atoms in the chain or as indicated. A $(C_{1-20})$alkyl, for example, includes alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl, and the like. An alkyl group may also be represented, for example, as a —$(CR^1R^2)_m$— group where $R^1$ and $R^2$ are independently hydrogen or are independently absent, and for example, m is 1 to 8, and such representation is also intended to cover both saturated and unsaturated alkyl groups.

An alkyl as noted with another group such as an aryl group, represented as "arylalkyl" for example, is intended to be a straight, branched, saturated or unsaturated aliphatic divalent group with the number of atoms indicated in the alkyl group (as in $(C_{1-20})$alkyl, for example) and/or aryl group (as in $(C_{5-14})$aryl, for example) or when no atoms are indicated means a bond between the aryl and the alkyl group. Nonexclusive examples of such group include benzyl, phenethyl and the like.

An "alkylene" group is a straight, branched, saturated or unsaturated aliphatic divalent group with the number of atoms indicated in the alkyl group; for example, a —$(C_1$-$C_3)$alkylene- or —$(C_1$-$C_3)$alkylenyl-.

"Amino acids" (AA) are well known in the art and are compounds containing an amine group (—$NH_2$) and a carboxylic acid group (—COOH), usually functionalized with a side chain for each amino acid. Amino acids include glycine, alanine, valine, leucine, isoleucine, serine, cysteine, selenocysteine, threonine, methionine, proline, phenylalanine, tyrosine, tryptophan, histidine, lysine, arginine, aspartate, glutamate, asparagine and glutamine. The bonding of two or more amino acids may form a peptide, such as a dipeptide, tripeptide etc . . . .

An "aryl" means a monocyclic or polycyclic ring assembly wherein each ring is aromatic, or when fused with one or more rings, forms an aromatic ring assembly. If one or more ring atoms is not carbon (e.g., N, S), the aryl is a heteroaryl. An aryl group may optionally be substituted as noted herein.

A "cyclyl" such as a monocyclyl or polycyclyl group includes monocyclic, or linearly fused, angularly fused or bridged polycycloalkyl, or combinations thereof. Such cyclyl group is intended to include the heterocyclyl analogs. A cyclyl group may be saturated, partially saturated or aromatic.

As used herein, a "dental adhesive" or "combined adhesive mixture" means a compound or composition disclosed herein that may be used as a treatment or pre-treatment on a dental unit or structure (such as a tooth) to adhere to a dental element or material (such as an orthodontic appliance (e.g. a bracket)) to a dental surface. The dental adhesive may be generally referred to as a composition used to adhere an orthodontic appliance to a dental surface, such as a tooth surface. In certain aspects, the dental surface may be pre-treated by etching or priming or by applying an adhesive to enhance adhesion with the compound and compositions disclosed herein.

A "filler" or "fillers" are particle(s) and/or fibers added to a material (plastics, adhesives, composite materials, concrete, cement) to lower the consumption of a more expensive material, such as a binder, or to improve the mechanical properties of the mixed materials. The filler may be made of various different materials known in the art, including minerals, e.g., silicate minerals (including mica, silica, glass, kaoline, zirconia etc . . . ) and biominerals (including calcium carbonate, silica, hydroxyapatite in tooth and bone), and metal/metal oxides, such as aluminum/alumina, titanium/titania etc . . . . For dental applications, a filler or a filler matrix may comprise one filler or a mixture of different fillers. The filler should generally be non-reactive. Representative fillers may include fumed silica, non-acid reactive fluoroaluminosilicate glasses fillers, quartz, ground glasses, non-water-soluble fluorides, silica gels, calcium silicate, zirconium silicate, zeolites and molecular sieves.

"Halogen" or "halo" means fluorine, chlorine, bromine or iodine.

A "heterocyclyl" or "heterocycle" is a cycloalkyl wherein one or more of the atoms forming the ring is a heteroatom that is a N, O, or S. Non-exclusive examples of heterocyclyl include piperidyl, 4-morpholyl, 4-piperazinyl, pyrrolidinyl, 1,4-diazaperhydroepinyl, 1,3-dioxanyl, and the like.

A "heteroaryl" means a cyclic aromatic group having five or six ring atoms, wherein at least one ring atom is a heteroatom e.g., N, S, O) and the remaining ring atoms are carbon. Where present, a nitrogen atom can be optionally quaternerized, and a sulfur atoms can be optionally oxidized. Heteroaryl groups include, but are not limited to, those derived from pyridazine, pyridine and pyrimidine. A heteroaryl also include, but is not limited to, bicyclic or tricyclic rings, where the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, indolizine, imidazo[1,2a]pyridine, quinoline, isoquinoline, phthalazine, quinoxaline, naphthyridine, quinolizine, indole, benzoxazole, benzopyrazole and benzothiazole. The bicyclic or tricyclic heteroaryl rings can be attached through either the heteroaryl group itself or the aryl, cycloalkyl, cycloalkenyl or heterocycloalkyl group to which it is fused. The heteroaryl groups of this invention can be substituted or unsubstituted as noted.

As used herein, a "mechanical property" or "mechanical properties" of a material includes the stiffness, hardness, Young's modulus (elastic modulus), toughness, strain at fracture (extensibility or flexibility), yield strength, ultimate strength, etc . . . of a material as disclosed in the application.

"Self assembled" or "self assembly" as used in "self-assembled monolayer" or SAMs are organic assembly structures that are formed by the adsorption of molecular compounds from a solution (or a gas phase) onto the surface of substrates or solids. Typically, the adsorbates organize spontaneously (sometimes epitaxially) into crystalline or semi-crystalline-like structures. The molecule (or ligand) such as the compound of the Formula I, that form SAMs has a chemical functionality that may be referred to as a "head group", with a specific affinity for the surface of a substrate. Once the head group of the compound binds to the surface of a substrate, the end group (EG) or tail group forms the surface of the SAM that may further bind with one or more layers, such as a second or subsequent self-assembled layer or SAM.

"Substituted or unsubstituted" or "optionally substituted" means that a group such as, for example, alkyl, aryl, heterocyclyl, $(C_{1-8})$cycloalkyl, hetrocyclyl($C_{1-8}$)alkyl, aryl $(C_{1-8})$alkyl, heteroaryl, heteroaryl($C_{1-8}$)alkyl etc . . . , unless specifically noted otherwise, may be unsubstituted or may substituted by 1, 2 or 3 substituents selected from the group such as halo, nitro, $F_3C$—, $F_3CO$—, $CH_3O$—, —C(O)OH, —$NH_2$, —OH, —SH, —$NHCH_3$, —$N(CH_3)_2$, —SMe, cyano and the like.

A "substrate" means a material, a base material or composition with a surface for printing and electronics fabrication and devices. Substrates are well known in the art, and may be used interchangeably with "material."

"Surface primer" or "primer" means a thin layer of material, such as the compound of the Formula I or Formula II, that may form a self-assembled layer, such as a SAM, that may be used to improve the adhesion of surfaces, such as metals, metal oxides, oxides and other materials, with a second layer of material, such as a second self-assembled layer or another SAM.

Experimental:

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

Preparation of Primers/Compounds:

The compounds may be prepared using conventional organic synthetic methods known in the art.

Scheme 1 Preparation of a representative primer

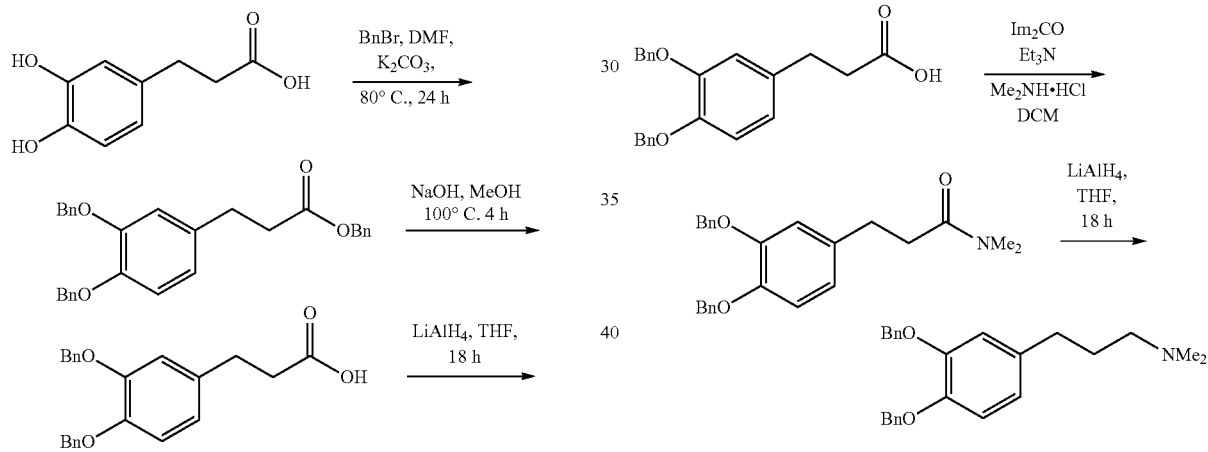

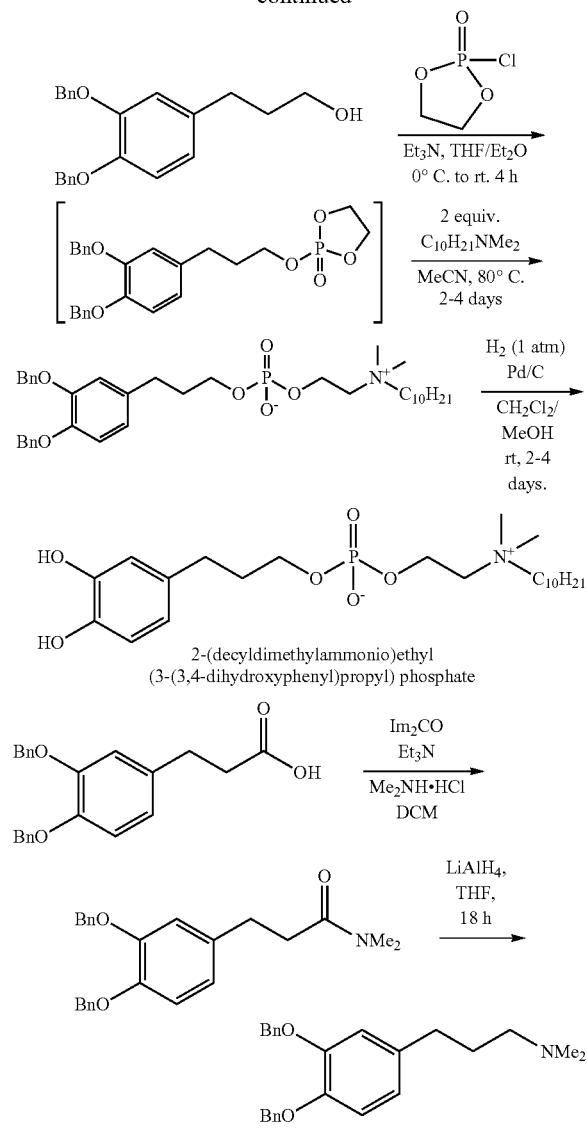

Scheme 2 Preparation of a represenative primer

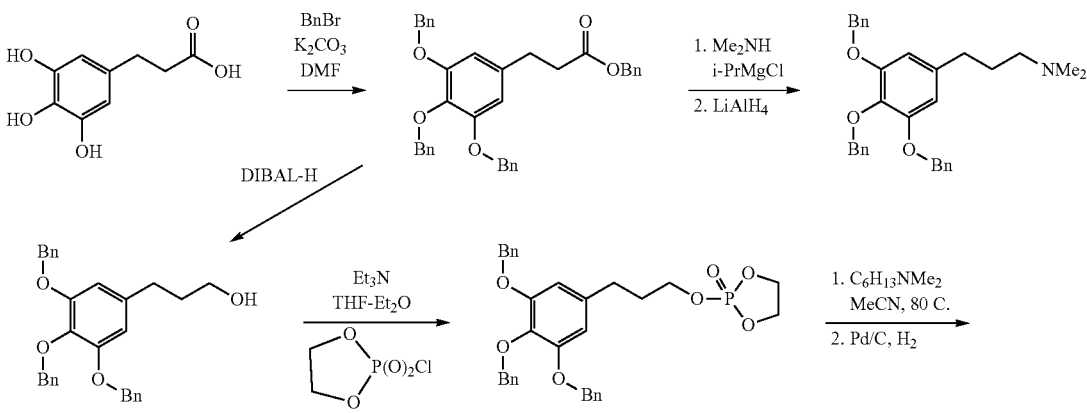

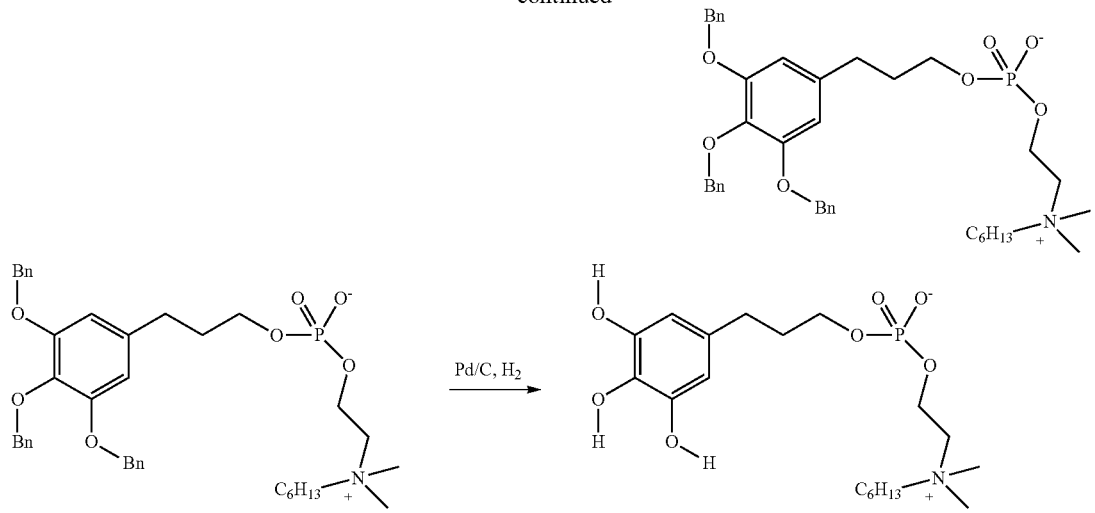

The compounds of Scheme 1 and Scheme 2 are prepared under similar reaction conditions, using the starting materials as shown. As shown in Scheme 2, the 3,4,5-trihydroxyphenyl propionic acid may be protected by benzylation using benzyl bromide and a base such as $K_2CO_3$. Amidation of the ester using an amine, such as dimethyl amine and a Grignard, such as isopropyl magnesium chloride, provides the amide. Reduction of the amide using lithium aluminum hydride provides the amine.

Alternatively, the tetrabenzyl-protected ester may be reduced to the corresponding alcohol using a hydride, such as diisobutylaluminum hydride. The alcohol may be converted to the corresponding phosphonate. The cyclic phosphate may be treated with an amine at elevated temperatures to provide the zwitterionic compound. The tribenzylated ether may be deprotected by hydrogenation with palladium on carbon.

Benzyl 3-(3,4,5-tris(benzyloxy)phenyl)propanoate:

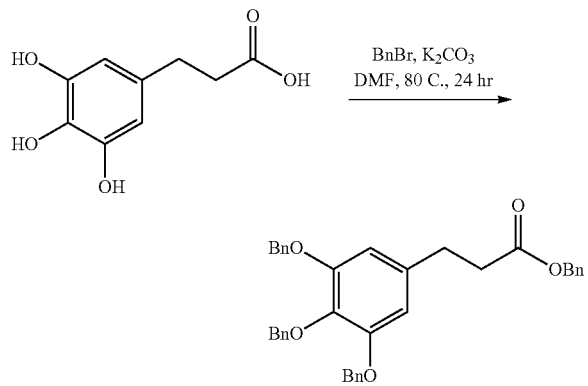

Benzyl 3-(3,4,5-tris(benzyloxy)phenyl)propanoate is prepared from the corresponding acid. A dried 500 ml 3-necked round bottom flask is fitted with rubber septa and a stir-bar and allowed to cool to room temperature (RT) under an argon flow. One equivalent of the acid is added, followed by 200 ml of anhydrous DMF with stirring. Once dissolved, anhydrous $K_2CO_3$ (6 equiv) is added with stirring. Fresh benzyl bromide (4.5 equiv) is added via syringe. The solution is placed in an oil bath at 80° C. and stirred for 1 day. The reaction is allowed to cool to RT, and then poured through a large fritted glass funnel into a 2 L round bottom flask to remove solids, and the reaction vessel is rinsed 3×300 ml EtOAc through the frit. The solvent is then removed with a rotary evaporator. Residual DMF is removed by 4 cycles of evaporation with toluene (500 ml). The crude residue is then re-dissolved in 1.5 L of $Et_2O$ and washed 5×100 ml cold water, 1×500 ml brine, dried over anhydrous $Na_2SO_4$, and concentrated under reduced pressure. The crude residue is then dry-loaded onto silica gel and purified by flash chromatography gradient elution 10-40% $Et_2O$/hexanes. The material is checked for purity by $^1$H-NMR and then carried on immediately to the next step.

3-(3,4,5-Tris(benzyloxy)phenyl)propanoic acid:

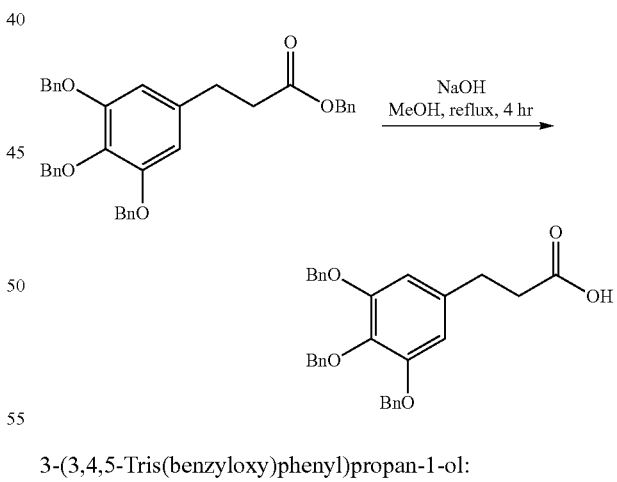

3-(3,4,5-Tris(benzyloxy)phenyl)propan-1-ol:

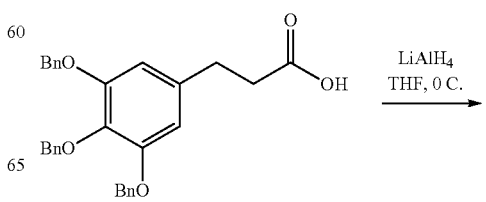

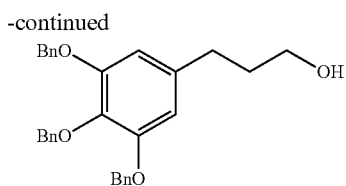

The alcohol is prepared from the acid by reduction with LiAlH$_4$. 7.24 grams of acid is dissolved in 100 ml of anhydrous THF and cooled to 0° C. Four equivalent of LiAlH$_4$ are then added in 4 portions. The reaction is left to stir overnight under argon while warming to RT. The reaction is quenched according to the Fieser workup, diluted with 100 ml of Et$_2$O and the aluminum solids filtered off. The solution is transferred to a separatory funnel, washed once with saturated NaHCO$_3$, dried over anhydrous Na$_2$SO$_4$, filtered, and evaporated under reduced pressure to afford crude material. The crude material is purified on a pad of silica eluting with Et$_2$O. The compound is isolated as a clear viscous oil.

Procedure for Preparation of Dimethylamide:

The dimethylamide is conveniently prepared using 1-1' carbonyldiimidazole as peptide coupling reagent. A dried flask is fitted with a stir bar and rubber septa under argon. One equiv of the corresponding carboxylic acid, four equiv of anhydrous Et$_3$N and anhydrous CH$_2$Cl$_2$ [0.5M] are added to the flask. The flask is cooled to 0° C. in an ice bath and stirred, and 1-1' carbonyldiimidazole (1.1 equiv) is added portion wise. The cooling bath is removed, and the solution is stirred for 30 minutes while warming to RT. Dimethylamine as the hydrochloride salt, (2 equiv), is added in one portion and the solution stirred until TLC indicated completion. The contents are transferred to a separatory funnel, diluted with CH$_2$Cl$_2$, and the organic layer is washed 2×1N HCl, 2×sat. NaHCO$_3$ and dried over anhydrous Na$_2$SO$_4$. The organic layer is filtered, evaporated under reduced pressure, and the crude residue is filtered over a pad of basic Al$_2$O$_3$ eluting with EtOAc, evaporated again, and purified by flash chromatography gradient elution with 50-100% EtOAc/hexanes. The dimethylamide is obtained in high purity (by TLC).

3-(3,4,5-Tris(benzyloxy)phenyl)-N,N-dimethylpropanamide:

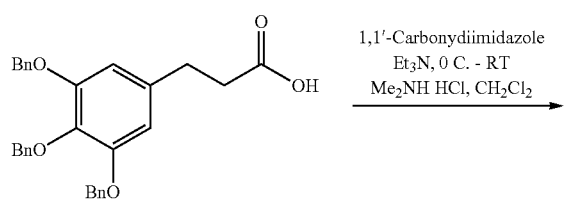

3-(3,4,5-Tris(benzyloxy)phenyl)-N,N-dimethylpropan-1-amine:

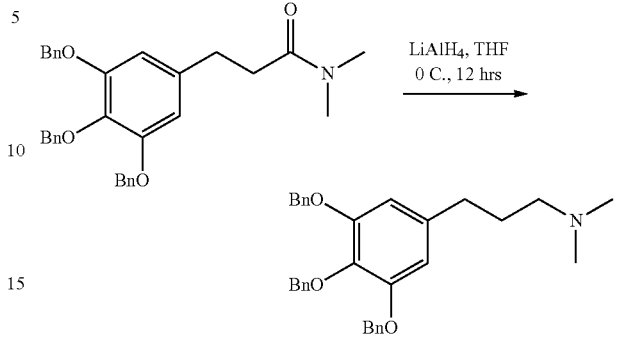

Preparation of Benzyl-protected Compounds by the Chabrier Reaction:

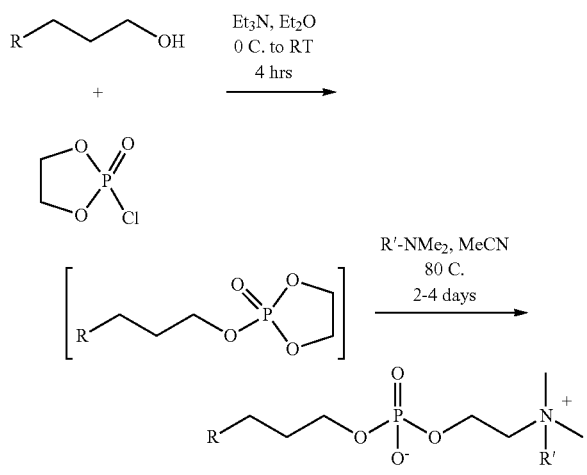

In one method, the benzyl-protected zwitterionic compounds are prepared via the Chabrier reaction, with certain modifications. Ethylene chlorophosphate (Aesar), stored in a freezer, is used as received. In a typical procedure, a flame-dried flask is fitted with a stir bar, rubber septa and cooled under positive argon flow. The alcohol is added to the flask followed by anhydrous Et$_2$O [0.4 M], 1.15 equiv Et$_3$N and stirred in an ice bath. 1.15 Equiv ethylene chlorophosphate is then added dropwise via syringe where the amine hydrochloride salt precipitates, and the reaction is stirred for 10 minutes. The flask is allowed to warm to RT with stirring for 4 hours. Hexanes equal to the volume of Et$_2$O in the flask, is added to precipitate of the amine hydrochloride salt. The contents of the flask are filtered over a pad of basic Celite into a RBF. The contents of the vessel are rinsed with hexanes, and then with Et$_2$O through the pad of basic Celite, and the solvents are removed under reduced pressure. The content is stored in the RBF under vacuum while a second reaction vessel is prepared.

A Schlenk-bomb type flask is fitted with a stir bar, flame dried, fitted with two rubber septa, under argon. The flask containing the phosphate ester is back-filled with argon, removed from the vacuum manifold, fitted with a rubber septum, and an argon needle is inserted into the septum. Anhydrous MeCN (2-4 ml per mmol alcohol) is added to this flask via syringe, and swirled until completely dissolved.

The MeCN solution containing the phosphate ester is transferred via syringe into the Schlenk flask, and the RBF is rinsed once with MeCN into the Schlenk flask. 2-4 Equiv of the amine are then added to the Schlenk flask, and the rubber septum is replaced with a Schlenk valve. The Schlenk valve is closed and the second rubber septum containing an argon needle is replaced with a glass adaptor and placed under high vacuum. The Schlenk valve is then opened and atmosphere is removed from the flask for 10 seconds to remove atmosphere from the flask, the Schlenk valve is then closed, and the flask is refluxed under vacuum with stirring for 2-4 days at 80° C. in an oil bath.

The flask is removed from the oil bath and allowed to cool to RT. The flask is then backfilled with argon, removed from the vacuum manifold and the Schlenk valve is removed. The reaction mixture is transferred via syringe into a RBF and the reaction vessel is washed 2× with $CH_2Cl_2$ added into the RBF. Volatiles are removed under reduced pressure and residual solvents are removed by evaporation with pentanes to give the crude compound. The residue is dissolved in a minimum amount of $CH_2Cl_2$ and purified on C2 bonded reverse phase silica.

Phosphate Intermediate:

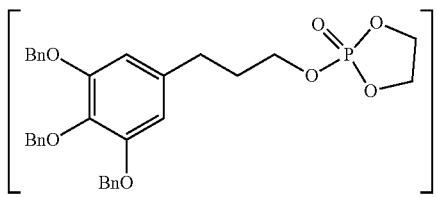

The cyclic phosphate intermediate is used immediately after preparation without further purification.

The preparation of the corresponding photo-cleavable o-nitrobenzyl derivatives may be performed by the similar Chabrier reaction of the cyclic phosphate with a selected functional derivative of the o-nitrobenzyl compound. See, for example, M. S. Kim et al., *Bioorganic & Medicinal Chemistry Letters*, 16 (2006) 4007-4010.

General Procedure for The De-Protection of Protected Alcohols by Hydrogenolysis:

The oxidative stability of each of the zwitterionic compounds containing unprotected alcohols (di-ols, tri-ols, tetra-ols and penta-ols), may be either in the solid state, a solution in $D_6$-DMSO, or as a colloidal dispersion in water. Effort is made to exclude atmospheric oxygen during all manipulations after the protected alcohols had been deprotected. As purification of unprotected alcohols may be difficult and require application of purification techniques under inert atmosphere, effort is made to increase the purity of the intermediates immediately preceding the de-protection step and the final products are all obtained in satisfactory purity as determined by FTIR, $^1$H— and $^{13}$C-NMR Spectroscopy.

A Schlenk-type flask is fitted with stir bar, fitted with two rubber septa. 10-20 wt % of Pd/C (5% Pd, Aesar) relative to mass of substrate is added to the flask. A small quantity of $CH_2Cl_2$ (4-8 ml) is added via syringe. A separate RBF containing the desired amount of substrate is fitted with a rubber septum and argon needle to purge air out. The appropriate volume of a 1:1 v/v mixture of $CH_2Cl_2$/MeOH is added via syringe. The flask is then swirled until the benzyl-protected compound is dissolved, and the solution containing the substrate is transferred via syringe to the Schlenk flask. The RBF is rinsed with MeOH (4-8 ml), and transferred via syringe to the Schlenk flask. The Schlenk valve is then opened placing the contents of the flask under vacuum and the atmosphere is removed under vacuum. The Schlenk valve is closed, the antechamber before the valve is backfilled with argon and the glass adaptor is replaced with a rubber septum. A hydrogen balloon (double ballooned) connected to a needle is placed through the septum and then a vent needle is placed though the septum to purge argon from the antechamber for 30 seconds then it is removed. The Schlenk valve is opened slowly to allow hydrogen into the reaction vessel and stirring is continued for 2-4 days, with periodic replacement of the hydrogen balloon with fresh balloons are used with every replacement.

Once the reaction is completed, the Schlenk valve is closed, and the remaining septum is replaced with a vacuum adaptor connected to a vacuum manifold and the antechamber before the Schlenk valve is placed under vacuum. The Schlenk valve is then opened placing the contents of the flask under vacuum and hydrogen gas is removed from the system in this manner for 5-10 minutes. A separate round bottom flask, fitted with a rubber septum, tared and placed under positive argon flow. The Schlenk flask is then backfilled with argon, and while under positive argon flow the Schlenk valve is removed and replaced with a rubber septum. A 30 ml, luer lock, PTFE coated syringe is fitted with a long metal needle, and the syringe is filled and purged with argon 3×, then it is inserted through the septum of the reaction vessel. The solution is then drawn into the syringe, along with a blanket of Argon and the metal needle is replaced with a 0.45 um PTFE syringe filter and disposable needle. The solution is then forced through the filter into a RBF to remove Pd/C, and the filtered solution is concentrated under reduced pressure, to afford pure deprotected coacervates, which were stored in a glove box protected from oxygen.

Compounds are all characterized by FTIR ($cm^{-1}$), $^{13}$C NMR (125 MHz, $d_6$-DMSO) δ (ppm), $^1$H NMR (600 MHz, $d_6$-DMSO) δ and HRMS, which confirms that the anticipated products are produced in satisfactory purity. The benzyl-protected coacervates are sufficiently stable for ESI-HRMS (QTOF2 Tandem Mass Spectrometer) and are fully characterized prior to hydrogenolysis.

Hydrogenolysis or debenzylation of some of the protected hydroxy compounds is accomplished with a slightly higher catalyst loading (20 wt % of Pd/C relative to mass of starting material) and extended reaction time (more than 2 days) for complete deprotection, affording the compounds in greater than 50% yield.

(2-Nitro-1,4-phenylene)bis(methylene) bis(2-methylacrylate):

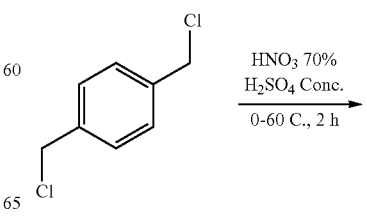

-continued

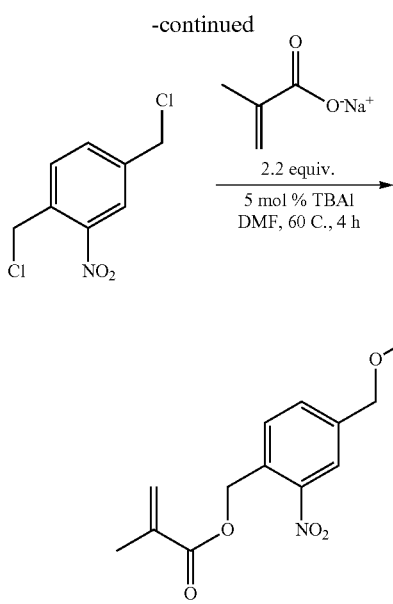

15 g of finely powdered 1,4-bis(chloromethyl)benzene was added to a 100 ml RBF with a large stir bar, and placed in an ice bath. 10 ml of 70% $HNO_3$ was added slowly and the resulting slurry was allowed to equilibrate to ice bath for 10 minutes. 15 ml of conc. sulfuric acid was added dropwise to the slurry over 15 minutes, where the compound dissolved. The mixture was removed from the cooling bath and allowed to come to RT with efficient stirring for 15 minutes. The flask was placed into an oil bath preheated to 60° C., and stirred at 60° C. for 2 hours. The flask was removed from the heating bath and cooled to RT, and the contents were poured onto 450 g of crushed ice/water 1:1. The remaining contents of the flask were rinsed into the ice water with 50 ml of water. The mixture was swirled gently and after all the ice melted, the yellow precipitate was collected by filtration, rinsed with additional water, and vacuum dried for several hours by breaking the cake up gently with a spatula. The crude material was dried overnight under high vacuum, and then crystallized from EtOH/water, filtered and dried to yield 16.8 g of 1,4-bis(chloromethyl)-2-nitrobenzene as a pale yellow powder.

4.4 g of 1,4-bis(chloromethyl)-2-nitrobenzene, 4.76 g of sodium methacrylate and 300 mg of tetra-n-butyl ammonium iodide, and a 2-3 mg of hydroquinone monomethyl ether as radical inhibitor are added to a dry 250 ml RBF fitted with a large stir bar under an argon atmosphere. 60 ml of anhydrous DMF were added via syringe with stirring resulting in the formation of a bright red slurry. The flask was placed in an oil bath preheated to 60° C., and the red slurry stirred under argon at 60° C. for 4 hours. The flask was cooled to RT and the contents poured onto 350 ml of crushed ice: water resulting in the formation of a fine pink precipitate. The resulting slurry was gently agitated and let stand at 0° C. in an ice bath for 15 minutes, and it was rapidly filtered on a glass frit with vacuum, washed with water, and vacuum dried for 3 hours. The resulting pink powder was placed onto a short column packed with 2.5 inches of silica on top of 0.5 inches of basic alumina and 300 ml of 25% EtOAc/hexanes was passed through the column into a 500 ml RBF where the organic solvents were removed in vacuo, and the white residue was evaporated twice with 100 ml of pentanes to afford 4.8 g (75%) of (2-nitro-1,4-phenylene)bis(methylene) bis(2-methylacrylate) as a white powder which was stored under argon and protected from light.

Bis(2-(methacryloyloxy)ethyl) O,O'-((2-nitro-1,4-phenylene)bis(methylene))disuccinate:

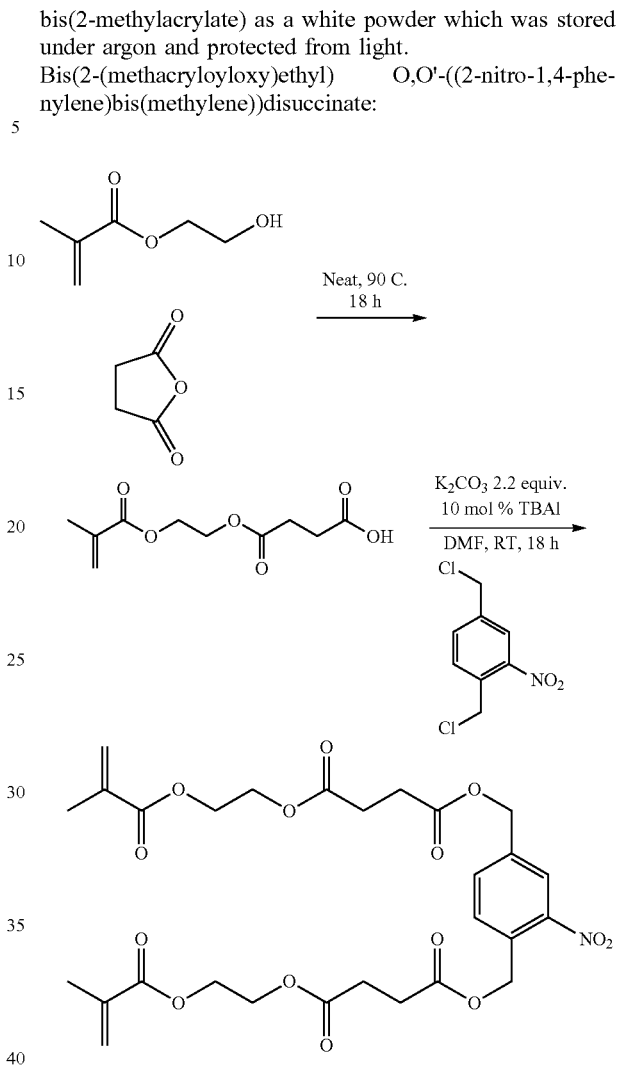

10 gm of 2-hydroxyethylmethacrylate, 7.7 gm of succinic anhydride and 50 mg of hydroquinone monomethyl ether were added into a 50 ml flask with a stir bar. The flask was purged with argon, sealed and heated to 90° C. with stirring for 18 hours. The flask was cooled to RT to afford 4-(2-(methacryloyloxy)ethoxy)-4-oxobutanoic acid in quantitative yield.

2.5 gm of 4-(2-(methacryloyloxy)ethoxy)-4-oxobutanoic acid was slowly added via syringe to a flask containing 25 ml of anhydrous DMF containing 1.5 gm of $K_2CO_3$ and 160 mg of tetra-n-butyl ammonium iodide. The solution was stirred at RT for 15 minutes. 1.1 gm of 1,4-bis(chloromethyl)-2-nitrobenzene was added in one portion, and the flask was resealed and stirred under argon at RT for 18 hours. The crude mixture was poured into a separatory funnel containing 250 ml of EtOAc, and the organic layer was washed 5× with water, 10× with sat. $NaHCO_3$ 1×, brine, dried over anhydrous magnesium sulfate, and concentrated in vacuo to afford crude material. Flash chromatography eluting with 0-50% EtOAc/hexanes afforded 1.2 gm of pure bis(2-(methacryloyloxy)ethyl) 0,0'-((2-nitro-1,4-phenylene) bis(methylene)) disuccinate, as a pale yellow liquid.

The following preparations are as described in *Soft Matter*, 2011, 7, 1426-1440.

2,2'-(2-Nitro-1,4-phenylene)bis(methylene)bis(oxy)bis (oxomethylene)-bis(oxy)bis-(ethane-2,1-diyl)bis(2-methylacrylate): A solution of hydroxyethylmethacrylate (HEMA) (1.9 g, 14 mmol) in anhydrous THF (5 mL) was added dropwise to a solution of carbonyldiimidazole (CDI) (2.4 g, 14 mmol) in anhydrous THF (20 mL). After stirring the reaction mixture overnight at RT, a solution of 2NPDM (1.3 g, 7.2 mmol) in anhydrous THF (20 mL) together with a 1.8 mol/L sodium ethanolate suspension (0.2 mL, 0.35 mmol) was added. Additional stirring for 5 d at room temperature was followed by filtration and reduction of the filtrate to dryness under reduced pressure. The residue was purified by column chromatography over silica using $CHCl_3$/MeOH (20:1) as eluent.

2,2'-(2-Nitro-1,4-phenylene)bis(methylene)bis(oxy)bis(oxomethylene)bis(azane-diyl)bis(ethane-2,1-diyl)bis(2-methylacrylate): 2NPDM (1.0 g, 5.5 mmol) was dissolved in anhydrous THF (10 mL) and added dropwise to a solution of 2-isocyanatoethyl methacrylate (1.7 g, 11 mmol) in anhydrous THF (15 mL) under nitrogen. The reaction mixture was heated to 65° C. and stirred for 24 h at this temperature. When the reaction was completed, solvent was evaporated and the residue was purified by column chromatography over silica using $CHCl_3$/MeOH (10:1).

Bis(2-(methacryloyloxy)ethyl)'-(2-nitro-1,4-phenylene) bis-(methylene) disuccinate: Mono-2-(methacryloyloxy) ethyl succinate (2.5 g, 11 mmol) was dissolved in anhydrous benzene and oxalyl chloride (2.8 g, 2 mmol) was added under nitrogen at room temperature. The reaction mixture was heated to 85° C. and refluxed for 3 h. After cooling to RT, benzene and excess oxalyl chloride were removed under reduced pressure. The acyl chloride obtained was dissolved in anhydrous THF (35 mL) and a solution of 2NPDM (1.0 g, 5.5 mmol) and triethylamine (1.2 g, 12 mmol) in THF (15 mL) was added dropwise. After stirring the mixture overnight at RT, precipitated solids were removed by filtration and the solution was reduced to dryness. The residue was dissolved in dichloromethane (100 mL), washed with water, dried with $MgSO_4$ and evaporated. The resulting oil was purified by column chromatography over silica using $CHCl_3$/MeOH (40:1) as eluent.

2-((1-(4-(4-(2-(Methacryloyloxy)ethylcarbamoyloxy)butoxy)-5-methoxy-2-nitro-phenyl)ethoxy)carbonylamino) ethyl methacrylate: 2-Isocyanatoethyl methacrylate (1.1 g, 7.4 mmol) was dissolved in anhydrous THF (5 mL) and added to a solution of HEMNPBA (1.0 g, 3.5 mmol) and dibutyltin dilaurate (0.11 g, 0.18 mmol) in anhydrous THF (25 mL) under nitrogen. After the mixture was heated to 65° C. and stirred for 48 h at this temperature, the reaction was complete. Solvent was removed under reduced pressure and the residue was purified by column chromatography over silica using $CHCl_3$/MeOH (10:1) as eluent.

AFM images of the primer are obtained at different concentrations: 0.001 mM (below its CAC), 0.05 mM (above CAC) and 5 mM. In one example of the primer, the 5 mM concentration shows a molecularly smooth surface suggesting consistent chemical configuration.

Atomic Force Microscopy (AFM) scans of a mica surface adsorbed with a compound of the present application from a solution in DI water of varying concentrations (5 mM). The compound forms a defect free atomically smooth bilayer on mica. No formation of small aggregates on the surface or thick multilayer is observed.

Surface Coating with Primer Compositions:
Deposition on Substrates for Medical Applications:

The surface coating, priming or deposition of the compound of the present application may be performed using standard methods known in the art, with the exception of the particular improved procedures and formulations developed and disclosed herein. For dental and medical applications, the primer may be provided in a solvent, such as water, ethanol or a mixture of a solution of water and ethanol. For dental applications, the same solvent or different solvent may be used to wash the surface of the tooth or enamel. In certain applications, the solvent is water and the process provides an environmentally friendly and effective process. In some methods using certain monomers, such as dimethacrylates, the solvent may not be needed. In one representative method using the compound of the Formula II, such as for compound 94, the use of a solvent in the process is not required. The resulting adhesive bonded or crosslinked under visible light, and then debonded (or cleaved) under UV light with physical stimulus or agitation.

In one application, the solution employed may be used at a neutral pH, or may be maintained in acidic conditions, at a pH<7, pH<6 or pH<5, such as where phenolic groups, hydroxyphenyl or polyhydroxyphenyl groups are present in the monomer to avoid oxidation of the phenols to the corresponding keto- compounds or quinones. The pH may be adjusted using an acid, such as phosphoric acid, hydrochloric acid, acetic acid or sulfonic acid. Depending on the type of application or the type of compound/primer employed, the pH of the solution may be >pH 5, >pH 6, >pH 6.5 or >pH 7. The solution may be degassed using an inert gas or using vacuum or a combination thereof, and the solution and container with the solution may be flushed with an inert gas, such as nitrogen or argon as desired.

Depending on the particular application, the concentration of the primer in the solution may be prepared at different concentrations and concentration ranges, such as a 0.0001 wt. % to 20 wt. %, 0.0001 wt. % to 15 wt. %, 0.0001 wt. % to 10 wt. %, about 0.001 wt. % to 10 wt. %, about 0.01 wt. % to 10 wt. %, about 0.1 wt. % to 10 wt. % or at about 0.1 wt. % to 5 wt. %; at 0.0001 wt %, 0.001 wt. %, 0.01 wt %, 0.1 wt %, 1.0 wt %, 5 wt %, 10 wt %, 15 wt %, 20 wt %, 25 wt % or more, in a solvent or solvent mixture. Ethanol, water, ethanol/water or other FDA approved solvents or solvent mixtures may be used for dental and medical applications. However, certain monomers or primers employed do not require the use of a solvent.

The bonding or binding of the adhesives of the compound of the Formula I or Formula II comprising acrylates or methacrylates and related groups on a substrate may be performed using standard methods known in the art. For example, binding may be initiated by photochemical, such as visible-light-initiated free radical polymerization, and may comprise a visible light photoinitiator, such as camphorquinone (CQ), at for example, about 0.25 wt %, and another initiator or co-initiator, such as 2-dimethylaminoethyl methacrylate (DMAEMA) at, for example, about 1 wt %.

Deposition on Substrates for Materials and Electronics Applications:

In one embodiment, the composition or the solution comprising the composition may be applied onto a surface, such as a mineral and/or metal oxide surface for a period of time to allow the compound/primer to set up or otherwise adsorbed or adhere to the surface. Depending on the nature of the surface and the structure of the compound, adhesion of the compound to the surface may take less than about 10 minutes, less than 5 minutes, less than 3 minutes, less than 2 minutes or less than about 1 minute. Once the primer is adsorbed to the surface, any excess primer may be removed from the surface by washing or rising with a solvent or solvent mixture. For certain applications, the solvent or solvent mixture may be water, ethanol, or a mixture of water and ethanol solution. Depending on the desired application, the surface with the adsorbed primer may be dried using air, heat or a combination thereof until the desired dryness is achieved. Depending on the particular application, no further processing is required after applying the composition to the surfaces.

In some embodiments, the solvent or solvent mixture employed in the primer solution and/or as a washing solvent may include water, methanol, ethanol, propanol, isopropanol, acetone, methylethyl ketone, dichloromethane, hexanes, cyclohexane, heptane, toluene, xylenes, THF, Me-THF and N-methylpyrrolidone; and various mixtures thereof. In certain applications, the solvent is water, or a mixture of the solvent(s) with water, and the process provides an environmentally friendly and effective process. For certain applications, no solvent is used.

The thickness of the adhered/adsorbed layer may be about 0.5-50 nm, 0.1-40 nm, 0.1-30 nm, 0.1-20 nm, 0.1-10 nm, 0.1-5 nm, 0.1-3 nm, 5-10 nm, greater than 20 nm, 100 nm or about 1-10 μm. For deposition of the solution comprising the compound/primer of the present application, the thickness will depend on the nature of the compound and the desired thickness of the layer and the nature of the application. For the preparation of SAMs, the thickness of the adhered/adsorbed layer may be less than for other self-assembled layers with the desired thickness. Optionally, the surface comprising a first layer may be completely dried before applying second layer or subsequent layers.

For other materials or electronic applications, the primer may be provided in a solvent, such as water, ethanol or a mixture of a solution of water and ethanol; or the solvent or solvent mixture employed in the primer solution and/or as a washing solvent may include methanol, ethanol, propanol, isopropanol, acetone, methylethyl ketone, dichloromethane, hexane, cyclohexane, heptane, toluene, xylenes, THF, Me-THF and N-methylpyrrolidone; and various mixtures thereof. In one variation, the same solvent or different solvent may be used to wash the surface of the substrate. In certain applications, no solvent is used with the primer.

In one application, the primer solution employed may be used at a neutral pH, or may be maintained in acidic conditions, at a pH<7, pH<6 or pH<5. The pH may be adjusted using an acid, such as phosphoric acid, hydrochloric acid, acetic acid, sulfonic acid, or acidic monomers such as 10-methacryloyl-decyl-dihydrogen-phosphate (MDP). Depending on the type of application or the type of compound/primer employed, the pH of the solution may be pH>5, pH>6, pH>6.5 or pH>7. The solution may be de-watered using a drying agent or degassed using an inert gas or using vacuum or a combination thereof, and the solution and container with the solution may be flushed with an inert gas, such as nitrogen or argon as desired.

Applications for Adhesive, Composites and Cement:

The treatment of adhesives, coating compositions, composites, paint and sealants with the primer or compounds of the present application is substantially similar to the methods described above, with standard procedural modifications known in the art for the treatment of such materials, and applying the advantages of the methods and compositions disclosed herein. For applying the method to fillers, for example, the mineral and/or metal oxide fillers (powders, fibers etc . . . ) are treated with the primer solution.

Fillers, such as pure fillers required as different compositions for different applications, are added to a primer solution. The solution is vigorously stirred and or sonicated for several minutes at about RT. The fillers are removed or isolated from the solvent, and are rinsed with a solvent or solvent mixture, and then filtered or isolated by centrifugation. Depending on the nature of the composition and the desired application, the fillers may be washed and rinsed more than once as needed. The fillers are then dried, such as by air blowing (for dental applications, for example), or may be dried by a freeze dried procedure, or dried by hot air, RT air or gas, or dried by vacuum, as known in the art to the desired level of dryness.

In one particular embodiment, the dried fillers may be added to various different materials, such as a monomer, a co-monomer mixture, pre-polymer and polymer for performing a polymerizing process with the fillers. In another embodiment as is known in the art, the fillers may be added to a pre-cement matrix or and adhesive for preparing an adhesive. In another embodiment, the fillers may be combined with a coating, a paint composition, a rubber or plastic, an ink and/or sealant before the composition is cured and/or dried. Employing the processes described herein, the mechanical properties (including the hardness, thickness etc . . . ) of the composite material (with the fillers) may be significantly increased or improved.

Photo-Cleavage or Debonding of Adhesive or Coating:

The photo-cleavage, photo-decomposition or debonding of the primer, coating or combined adhesive mixture using various irradiation protocols and methods as known in the art. Irradiation may be performed by specifically cleaving the primer using infrared (IR), ultraviolet (UV) and/or a combination of IR and UV irradiation for a sufficient period of time to cleave the primer, coating or adhesive. Depending on the nature of the composition, photo-irradiation may be performed with 265 nm, 300 nm, 340 nm, 365 nm, 380 nm or 400 nm, at about RT, for a sufficient period of time to debond the primer.

For example, a primer or combined adhesive mixture may be photolyzed by photo-irradiation, such as with a 10 W UV LED light, a 20 W UV LED light, a 130 W UV LED lamp (NobleCure-Altair 75), a 400 W medium pressure mercury lamp or a portable LX300UV xenon lamp or for example, with a UV lamp at 340 nm (light intensity=20 mW/cm$^2$), optionally in conjunction with a monochromator at a desired wavelength, such as at 260 nm, 340 nm, 365 nm, 380 nm or 400 nm, or as determined based on the nature of the primer or adhesive, for a sufficient period of time, with the debonding of the material (primer or coating) being monitored until the debonding is complete.

Depending on the nature of the primer, composition or combined adhesive mixture, the irradiation may be performed by IR, UV or a combination thereof. The irradiation may be performed at about RT or above RT, such as about 27° C., 30° C. or about 35° C. or higher, for a sufficient amount of time to debond the material. In certain embodiments, the debonding may be performed in conjunction with physical force, such as twisting or moving the substrates to debond, by sonication, or combinations thereof.

Use of Adhesives and Combined Adhesive Mixtures in Dental Applications:

The following are representative description to demonstrate a procedure for the use of a dental adhesive of the present application.

Generally, the photocleavable acrylates, such as the photocleavable dimethacrylates of the present application were mixed with a visible light photoinitiator such as camphorquinone (CQ, at about 0.25 wt %) and an acrylate such as 2-dimethylaminoethyl methacrylate (DMAEMA, at about 1 wt %), and applied on a surface (e.g., a surface of a tooth) as a primer before applying an adhesive, such as a dental adhesive (also referred to in the art as an adhesive, a resin cement, a sealant or a primer [or second primer]). In some compositions, the photocleavable acrylates, such as the dimethacrylates (99-50 wt %) were mixed with a dental resin mixture (1-50 wt %) of Bis-GMA, TEGMA, DMAEMA, CQ, to enhance its mechanical strength of the visible light cured and UV light-cleavable primed layer.

When the composition are used as a mixture of the photocleavable primer or adhesive, such as a photocleavable acrylate such as a dimethacrylate, for example, the photocleavable acrylates may comprise of about 10-99 wt % when mixed with a dental adhesive, that may be present in about 90-1 wt %. In some mixtures, the photocleavable acrylates comprise of about 50 wt %, 60 wt %, 70 wt %, 80 wt %, 90 wt %, 95 wt % or more. In certain mixtures, the adhesive may be present in about 40 wt %, 30 wt %, 20 wt %, 10 wt %, 5 wt %, 3 wt % or about 1 wt %.

For clarity of the compositions referred to herein, in general, a first composition that is applied to a surface is referred to as a photocleavable monomer composition that may be a single photocleavable monomer, a mixture of photocleavable monomers or a mixture of photocleavable monomer(s) and non-photocleavable monomers (or monomer blends). A second composition that is applied may be referred to as a dental adhesive, which may be adhesives or mixtures of adhesives known in the art. And the combination of the first composition and the dental adhesive may be referred to as a combined adhesive mixture.

As a representative example of a dental adhesive, Bis-GMA (20 g) and TEGMA (20 g, 18.2 mL) were added to a 100 mL flask. Because Bis-GMA is very viscous, a heat gun was used to heat the mixture and a homogeneous mixture of Bis-GMA and TEGDMA was obtained. An aliquot (8.8 mL) of the mixture was taken to a 20 mL vial. DMAEMA (71 µL) and CQ (33 mg) were added to the vial and blended with aid of sonication. The photocleavable monomer blends (including the photocleavable monomer and the dental monomer adhesive mixture) were spread thinly on a surface, such as a tooth, metal or mineral surfaces, as a primery adhesive layer.

The dental adhesive was then applied over the primed surface, that is, the surface covered with the photocleavable monomer or monomer blend or mixture, to form the secondary adhesive layer. An object, such as a bracket or a dental appliance, is then fitted or mounted on the combination of two or more adhesive layers. A source of visible light is applied to the combined adhesive mixture comprising the dental adhesive layers that consist of a photocleavable adhesive (or primer), dental adhesive (or dental primer) and dental resin composite (or adhesive) and the mounted object, for a sufficient period of time to allow the adhesive layer to cure and the object secured to the dental surface.

Depending on the purpose for using the photocleavable adhesive layer, the removal or debonding of the combined adhesive mixture (along with the coating, cement or sealant) and the object (such as a bracket) may be performed after a desired period of time. Depending on the application, the period of time may be several minutes, several days, several weeks, several months or several years until the purpose and time for using such combined adhesive mixture is complete.

The debonding or removal of the combined adhesive mixture (coating, cement or sealant) from the surface, such as a tooth surface, may be performed by exposing the combined adhesive mixture (or photocleavable adhesive or mixtures of adhesives) or area with UV radiation, UV light or IR light. Optionally, the exposure to UV light may be performed along with physical agitation, such as by jiggling, moving, rocking, pulling or prying, vibrating or sonicating for a sufficient period of time to debond or remove the object from the surface. Depending on the nature of the combined adhesive mixture, the exposure and optionally, the physical agitation, may be performed over a period of about 30 seconds, about 1 minute, 2 minutes, 3 minutes, 5 minutes or about 10 minutes or less.

Depending on the nature of the combined adhesive mixture, the strength of the UV light and the nature of the object mounted on the surface, the physical agitation (such as sonication), the bonding strength of the combined adhesive mixture (or the relative amount of effort to remove an object from the surface) is reduced by up to about 90%, 95% or about 99% (when compared to a process where there is no UV light exposure to debond), allowing for a significantly reduced force (such as jiggling or sonication, for example) to remove the object from the surface.

Representative compounds of the Formula I that may be prepared according to the present disclosure is provided in the Table:

TABLE
| Compound No | EG— | —SP1—SP2—SP3— | —Ar—(BG)$_a$ |
|---|---|---|---|
| 1 | —OH | —(CH$_2$)$_6$—NHC(O)—(CH$_2$CH$_2$O)$_2$—(CH$_2$)$_6$— |  |
| 2 | —OH | —(CH$_2$)$_6$—NHC(O)—(CH$_2$CH$_2$O)$_2$—(CH$_2$)$_6$— | 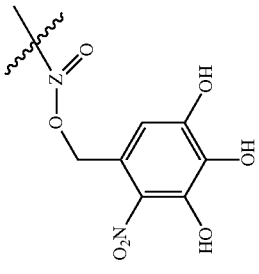 |
| 3 | —OH | —(CH$_2$)$_6$—NHC(O)—(CH$_2$CH$_2$O)$_2$—(CH$_2$)$_6$— | 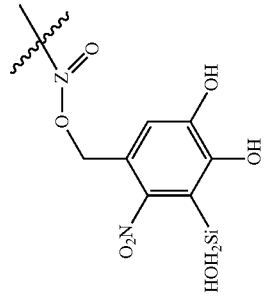 |

TABLE-continued
| Compound No | EG— | —SP1—SP2—SP3— | —Ar—(BG)$_a$ |
|---|---|---|---|
| 4 | —OH | —(CH$_2$CH$_2$O)$_3$CH$_2$CH$_2$—CONCH$_3$—(CH$_2$CH$_2$O)$_3$CH$_2$CH$_2$— |  |
| 5 | —OH | —(CH$_2$CH$_2$O)$_3$CH$_2$CH$_2$—CONCH$_3$—(CH$_2$CH$_2$O)$_3$CH$_2$CH$_2$— | 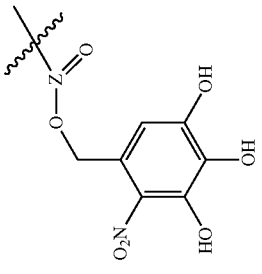 |
| 6 | —OH | —(CH$_2$)$_6$—OPO$_3^-$—(CH$_2$)$_2$—N$^+$(CH$_3$)$_2$—(CH$_2$)$_6$— | 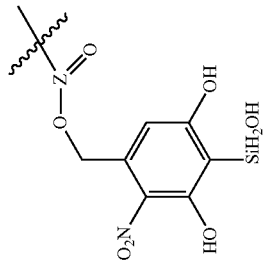 |

TABLE-continued
EG—SP1—SP2—SP3—[Ar]—(BG)$_a$
| Compound No | EG— | —SP1—SP2—SP3— | —Ar—(BG)$_a$ |
|---|---|---|---|
| 7 | —OH | —(CH$_2$)$_6$—OPO$_3^-$(CH$_2$)$_2$—N$^+$(CH$_3$)$_2$—(CH$_2$)$_6$— |  |
| 8 | —OH | —(CH$_2$)$_6$—OPO$_3^-$(CH$_2$)$_2$—N$^+$(CH$_3$)$_2$—(CH$_2$)$_6$— | 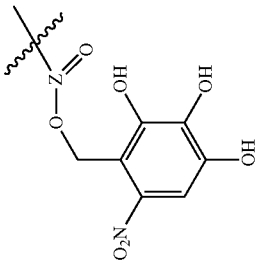 |
| 9 | —OH | —(CH$_2$)$_6$—OPO$_3^-$(CH$_2$)$_2$—N$^+$(CH$_3$)$_2$—(CH$_2$)$_6$— | 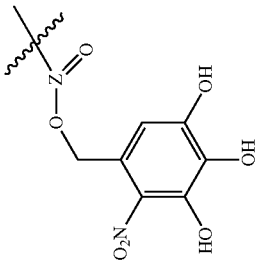 |

TABLE-continued
EG—SP1—SP2—SP3—[Ar]—(BG)$_a$
| Compound No | EG— | —SP1—SP2—SP3— | —Ar—(BG)$_a$ |
|---|---|---|---|
| 10 | —SiH$_2$OH | —(CH$_2$)$_6$—NHC(O)—(CH$_2$CH$_2$O)$_2$—(CH$_2$)$_6$— |  |
| 11 | —SiH$_2$OH | —(CH$_2$)$_6$—NHC(O)—(CH$_2$CH$_2$O)$_2$—(CH$_2$)$_6$— | 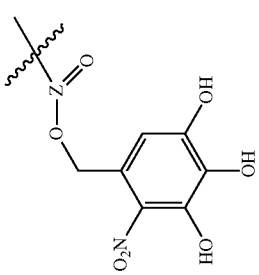 |
| 12 | —SiH$_2$OH | —(CH$_2$)$_6$—NHC(O)—(CH$_2$CH$_2$O)$_2$—(CH$_2$)$_6$— | 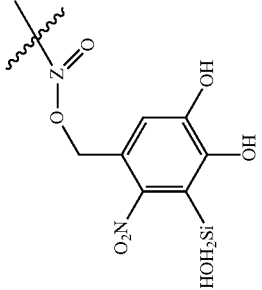 |

TABLE-continued
| Compound No | EG— | —SP1—SP2—SP3— | —Ar—(BG)$_a$ |
|---|---|---|---|
| 13 | —SiH$_2$OH | —(CH$_2$)$_6$—OPO$_3^-$—(CH$_2$)$_2$—N$^+$(CH$_3$)$_2$—(CH$_2$)$_6$— |  |
| 14 | —SiH$_2$OH | —(CH$_2$)$_6$—OPO$_3^-$—(CH$_2$)$_2$—N$^+$(CH$_3$)$_2$—(CH$_2$)$_6$— | 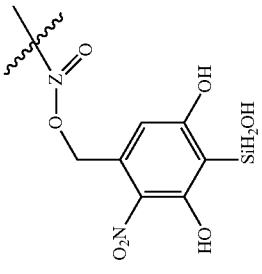 |
| 15 | —SiH$_2$OH | —(CH$_2$)$_6$—OPO$_3^-$—(CH$_2$)$_2$—N$^+$(CH$_3$)$_2$—(CH$_2$)$_6$— | 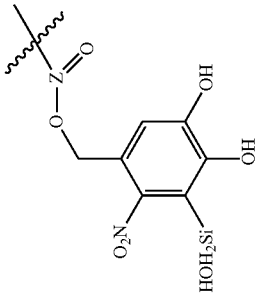 |

TABLE-continued
| Compound No | EG— | —SP1—SP2—SP3— | —Ar—(BG)$_a$ |
|---|---|---|---|
| 16 | C$_6$alkyl | —(CH$_2$)$_6$—NHC(O)—(CH$_2$CH$_2$O)$_2$—(CH$_2$)$_6$— |  |
| 17 | C$_6$alkyl | —(CH$_2$)$_6$—NHC(O)—(CH$_2$CH$_2$O)$_2$—(CH$_2$)$_6$— | 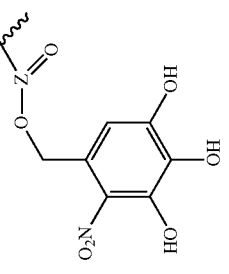 |
| 18 | C$_6$alkyl | —(CH$_2$)$_6$—NHC(O)—(CH$_2$CH$_2$O)$_2$—(CH$_2$)$_6$— | 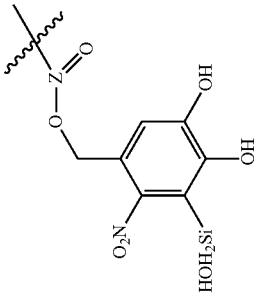 |

TABLE-continued
EG—SP1—SP2—SP3—[Ar]—(BG)$_a$
| Compound No | EG— | —SP1—SP2—SP3— | —Ar—(BG)$_a$ |
|---|---|---|---|
| 19 | C$_6$alkyl | —(CH$_2$)$_6$—OPO$_3$—(CH$_2$)$_2$—N$^+$(CH$_3$)$_2$—(CH$_2$)$_6$— |  |
| 20 | C$_6$alkyl | —(CH$_2$)$_6$—OPO$_3$—(CH$_2$)$_2$—N$^+$(CH$_3$)$_2$—(CH$_2$)$_6$— | 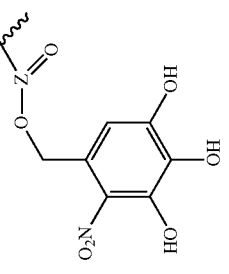 |
| 21 | —CF$_3$ | —(CH$_2$)$_6$—NHC(O)—(CH$_2$CH$_2$O)$_2$—(CH$_2$)$_6$— | 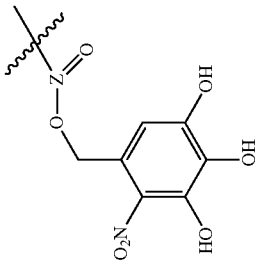 |

TABLE-continued
EG—SP1—SP2—SP3—[Ar]—(BG)$_a$
| Compound No | EG— | —SP1—SP2—SP3— | —Ar—(BG)$_a$ |
|---|---|---|---|
| 22 | —CF$_3$ | —(CH$_2$)$_6$—NHC(O)—(CH$_2$CH$_2$O)$_2$—(CH$_2$)$_6$— | 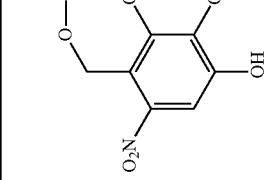 |
| 23 | —CF$_3$ | —(CH$_2$)$_6$—NHC(O)—(CH$_2$CH$_2$O)$_2$—(CH$_2$)$_6$— | 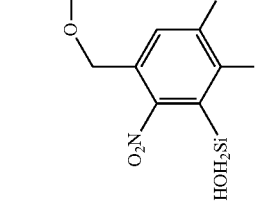 |
| 24 | —CF$_3$ | —(CH$_2$CH$_2$O)$_3$CH$_2$CH$_2$—CONCH$_3$—(CH$_2$CH$_2$O)$_3$CH$_2$CH$_2$— | 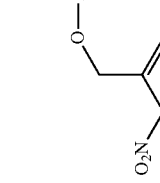 |

TABLE-continued
| Compound No | EG— | —SP1—SP2—SP3— | —Ar—(BG)$_a$ |
|---|---|---|---|
| 25 | —CF$_3$ | —(CH$_2$)$_6$—OPO$_3$—(CH$_2$)$_2$—N$^+$(CH$_3$)$_2$—(CH$_2$)$_6$— |  |
| 26 | —CF$_3$ | —(CH$_2$)$_6$—OPO$_3$—(CH$_2$)$_2$—N$^+$(CH$_3$)$_2$—(CH$_2$)$_6$— | 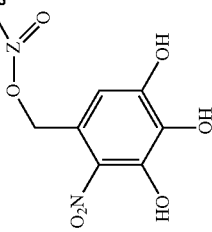 |
| 27 | —CF$_3$ | —(CH$_2$)$_6$—OPO$_3$—(CH$_2$)$_2$—N$^+$(CH$_3$)$_2$—(CH$_2$)$_6$— | 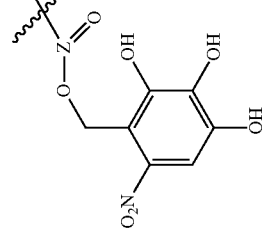 |

TABLE-continued
| Compound No | EG— | —SP1—SP2—SP3— | —Ar—(BG)$_a$ |
|---|---|---|---|
| 28 | Phenyl- | —(CH$_2$)$_6$—NHC(O)—(CH$_2$CH$_2$O)$_2$—(CH$_2$)$_6$— |  |
| 29 | Phenyl- | —(CH$_2$)$_6$—NHC(O)—(CH$_2$CH$_2$O)$_2$—(CH$_2$)$_6$— | 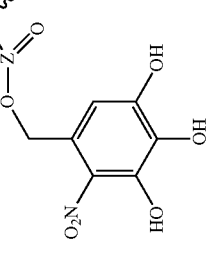 |
| 30 | Phenyl- | —(CH$_2$)$_6$—NHC(O)—(CH$_2$CH$_2$O)$_2$—(CH$_2$)$_6$— | 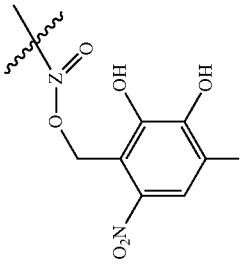 |

TABLE-continued
| Compound No | EG— | —SP1—SP2—SP3— | —Ar—(BG)$_a$ |
|---|---|---|---|
| 31 | Phenyl- | —(CH$_2$CH$_2$O)$_3$CH$_2$CH$_2$—CONCH$_3$—(CH$_2$CH$_2$O)$_3$CH$_2$CH$_2$— |  |
| 32 | Phenyl- | —(CH$_2$CH$_2$O)$_3$CH$_2$CH$_2$—CONCH$_3$—(CH$_2$CH$_2$O)$_3$CH$_2$CH$_2$— | 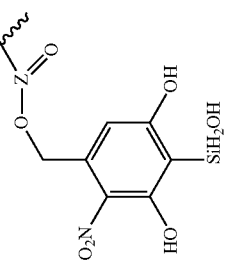 |
| 33 | Phenyl- | —(CH$_2$)$_6$—OPO$_3^-$—(CH$_2$)$_2$—N$^+$(CH$_3$)$_2$—(CH$_2$)$_6$— | 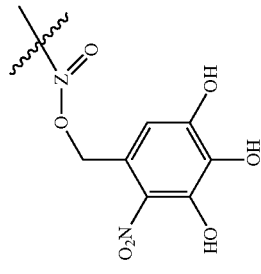 |

TABLE-continued
| Compound No | EG— | —SP1—SP2—SP3— | —Ar—(BG)$_a$ |
|---|---|---|---|
| 34 | Phenyl- | —(CH$_2$)$_6$—OPO$_3$—(CH$_2$)$_2$—N$^+$(CH$_3$)$_2$—(CH$_2$)$_6$— |  |
| 35 | Phenyl- | —(CH$_2$)$_6$—OPO$_3$—(CH$_2$)$_2$—N$^+$(CH$_3$)$_2$—(CH$_2$)$_6$— | 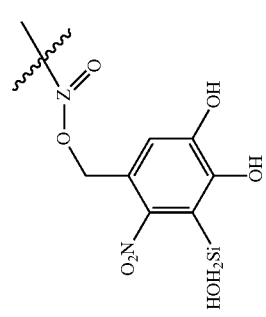 |
| 36 | C$_6$alkyl | —(CH$_2$CH$_2$O)$_3$CH$_2$CH$_2$O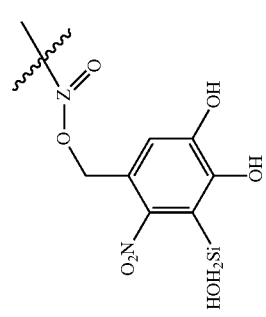(CH$_2$CH$_2$O)$_3$CH$_2$CH$_2$— | 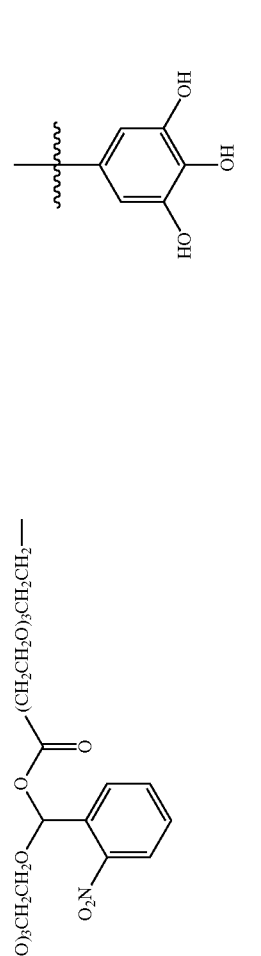 |
| 37 | C$_6$alkyl | —(CH$_2$CH$_2$O)$_3$CH$_2$CH$_2$O(CH$_2$CH$_2$O)$_3$CH$_2$CH$_2$— |  |

TABLE-continued
| Compound No | EG— | —SP1—SP2—SP3— | —Ar—(BG)$_a$ |
|---|---|---|---|
| 38 | HO— | —(CH$_2$CH$_2$O)$_3$CH$_2$CH$_2$O(CH$_2$CH$_2$O)$_3$CH$_2$CH$_2$— | 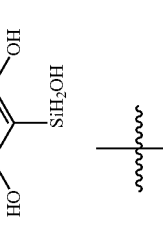 |
| 39 | Phenyl- | —(CH$_2$CH$_2$)$_6$NHC(O)O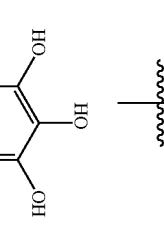(CH$_2$CH$_2$O)$_3$CH$_2$CH$_2$— | 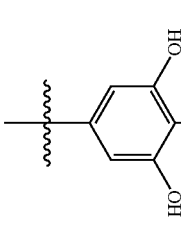 |
| 40 | Phenyl- | —(CH$_2$CH$_2$)$_6$NHC(O)O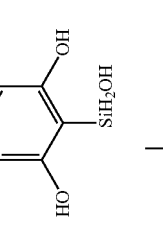(CH$_2$CH$_2$O)$_3$CH$_2$CH$_2$— | 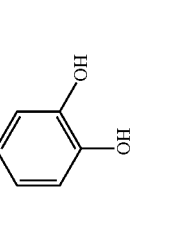 |
| 41 | CH$_2$CHCOO— | —(CH$_2$CH$_2$O)$_3$CH$_2$CH$_2$O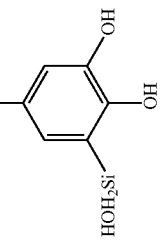(CH$_2$CH$_2$O)$_3$CH$_2$CH$_2$— |  |

TABLE-continued

| Compound No | EG— | —SP1—SP2—SP3— | —Ar—(BG)$_a$ |
|---|---|---|---|
| 42 | CH$_2$CHCOO— | —(CH$_2$CH$_2$O)$_3$CH$_2$CH$_2$—O—CO—CH(C$_6$H$_4$-o-NO$_2$)—O—(CH$_2$CH$_2$O)$_3$CH$_2$CH$_2$— | 3,4-dihydroxyphenyl |
| 43 | CH$_2$CHCOO— | —(CH$_2$CH$_2$O)$_3$CH$_2$CH$_2$—O—CO—CH(C$_6$H$_4$-o-NO$_2$)—OCOCH$_2$CH$_2$O— | 3,4-dihydroxyphenyl |
| 44 | CH$_2$CHCOO— | —(CH$_2$CH$_2$O)$_3$CH$_2$CH$_2$—O—CO—CH(C$_6$H$_4$-o-NO$_2$)—O—CH$_2$CH$_2$O—(CH$_2$CH$_2$O)$_3$CO— | 3,4-dihydroxyphenyl |
| 45 | CH$_2$CHCOO— | —(CH$_2$CH$_2$O)$_2$CO(CH$_2$CH$_2$O)$_3$CH$_2$CH$_2$O—CO—CH(C$_6$H$_4$-o-NO$_2$)—O—CH$_2$CH$_2$O—(CH$_2$CH$_2$O)$_3$CO— | 3,4-dihydroxyphenyl |

Compounds that may be used as co-polymers may also include:
Fragments for Preparing Monomers
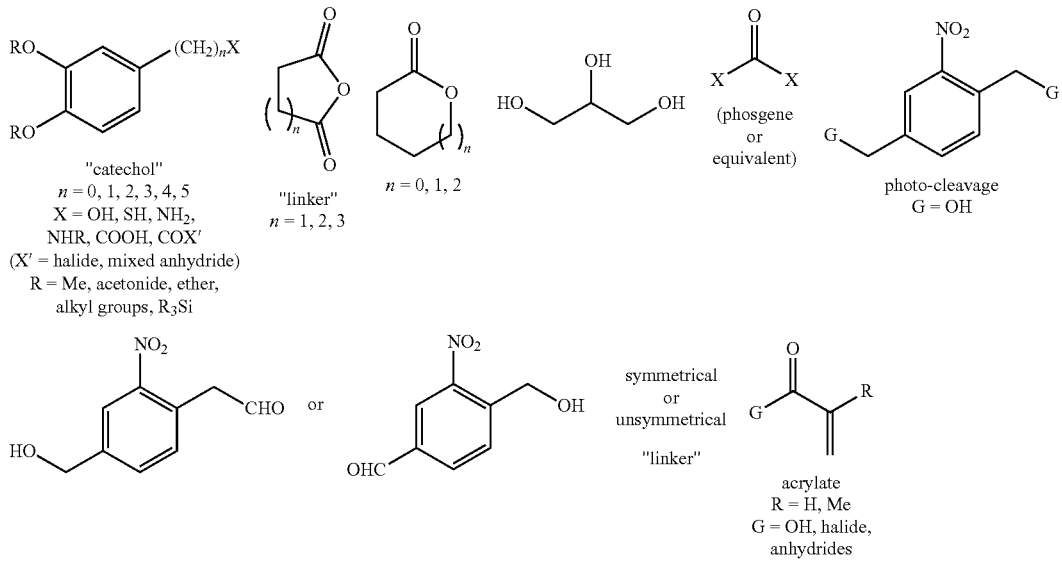
Monomers:
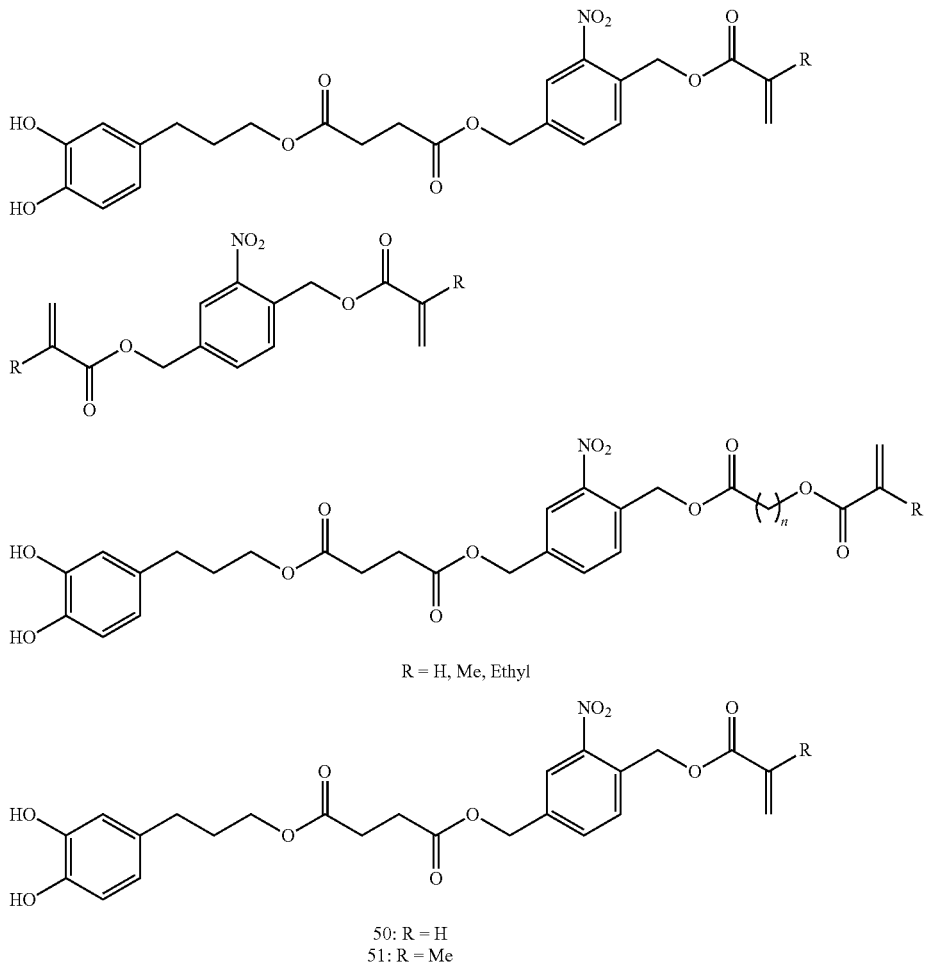
50: R = H
51: R = Me

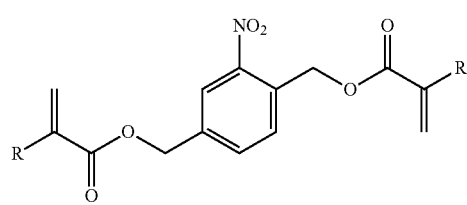
52: R = H
53: R = Me
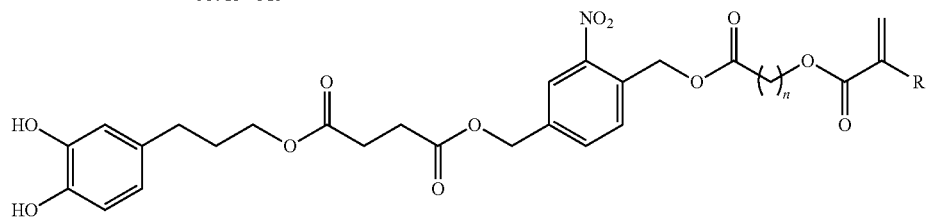
55: R = H, $n$ = 1; 56: R = Me, $n$ = 1
57: R = H, $n$ = 2; 58: R = Me, $n$ = 2
59: R = H, $n$ = 3; 60: R = Me, $n$ = 3
61: R = H, $n$ = 4; 62: R = Me, $n$ = 4
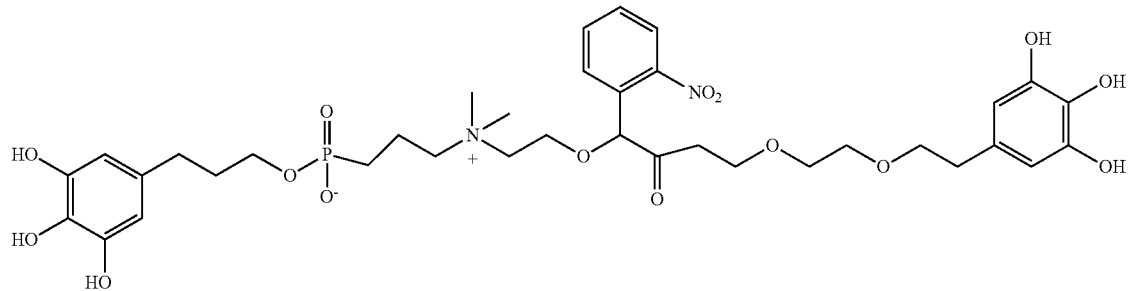
46
Additional monomers that may be used as co-polymers include:
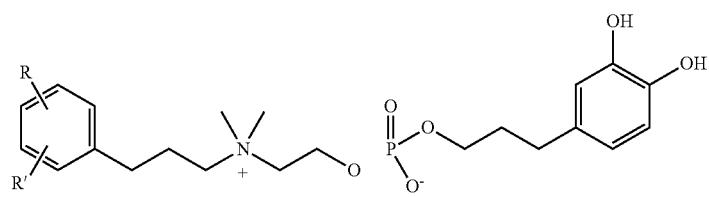
63 R and R' = H
64 R and R' = 3,4-dihydroxy
65 R and R' = 3,5-ditrifluoromethyl
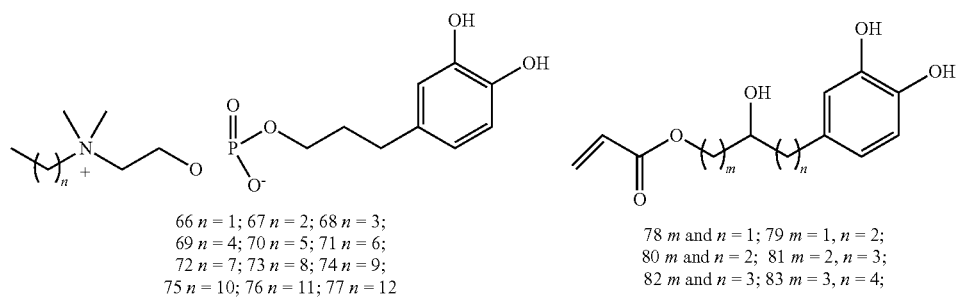
66 $n$ = 1; 67 $n$ = 2; 68 $n$ = 3;
69 $n$ = 4; 70 $n$ = 5; 71 $n$ = 6;
72 $n$ = 7; 73 $n$ = 8; 74 $n$ = 9;
75 $n$ = 10; 76 $n$ = 11; 77 $n$ = 12
78 $m$ and $n$ = 1; 79 $m$ = 1, $n$ = 2;
80 $m$ and $n$ = 2; 81 $m$ = 2, $n$ = 3;
82 $m$ and $n$ = 3; 83 $m$ = 3, $n$ = 4;

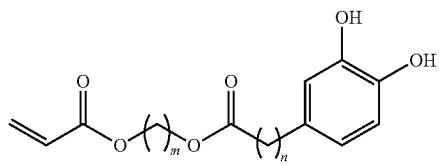

84 m and n = 1; 85 m = 1, n = 2;
86 m and n = 2; 87 m = 2, n = 3;
88 m and n = 3; 89 m = 3, n = 4;

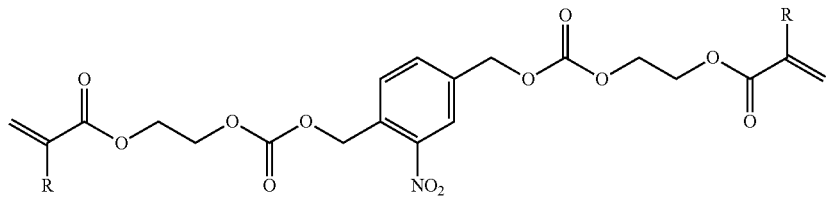

89: R = H
90: R = Me

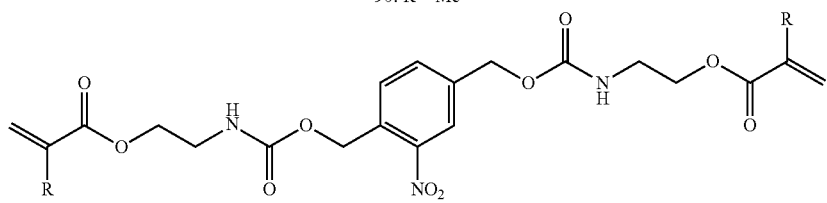

91: R = H
92: R = Me

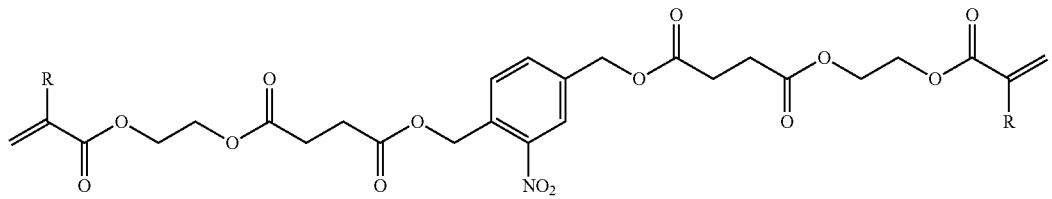

93: R = H
94: R = Me

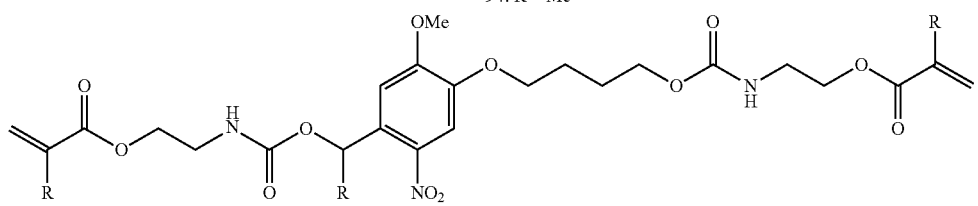

95: R = H
96: R = Me

REFERENCES

1. B. K. Ahn, D. W. Lee, J. N. Israelachvili, J. H. Waite, Surface-initiated self-healing of polymers in aqueous media. *Nat Mater* 13, 867-872 (2014); 2. B. K. Ahn, S. Das, R. Linstadt, Y. Kaufman, N. R. Martinez-Rodriguez, R. Mirshafian, E. Kesselman, Y. Talmon, B. H. Lipshutz, J. N. Israelachvili, J. H. Waite, High-performance mussel-inspired adhesives of reduced complexity. *Nat Commun* 6, (2015); 3. H. Zeng, D. S. Hwang, J. N. Israelachvili, J. H. Waite, Strong reversible $Fe^{3+}$-mediated bridging between dopa-containing protein films in water. *Proceedings of the National Academy of Sciences* 107, 12850-12853 (2010). 4. H. Lee, N. Scherer, P. Messersmith, Single-molecule mechanics of mussel adhesion. *Proc Natl Acad Sci USA*, 103, 12999-13003 (2006). 5. M. Krogsgaard, A. Andersen, H. Birkedal, Gels and threads: Mussel-inspired one-pot route to advanced responsive materials. *Chemical Communications* 50, 13278-13281 (2014). 6. C. N. Z. Schmitt, Y. Politi, A. Reinecke, M. J. Harrington, Role of Sacrificial Protein—Metal Bond Exchange in Mussel Byssal Thread Self-Healing. *Biomacromolecules* 16, 2852-2861 (2015). 7. F. Zhou et al., Grafting zwitterionic polymer brushes via electrochemical surface-initiated atomic-transfer radical polymerization for anti-fouling applications, *J. Mater. Chem. B*, 2014, 2, 5352. 8. P. B. Messersmith et al., Universal Surface-Initiated Polymerization of Antifouling Zwitterionic Brushes Using a Mussel-Mimetic Peptide Initiator, *Langmuir,* 2012, 28, 7258-7266. 9. P. B. Messersmith et al., Single-molecule mechanics of mussel adhesion, *PNAS,* 103, No. 35, 12999-13003 (2006).

We claim:

1. A dental adhesive or primer comprising a formulation or a mixture of:

a) a compound of the Formula II:

wherein:

m is 1, 2 or 3; n is 1, 2 or 3; i is 1, 2 or 3;

each EG and EG1 is an end group independently selected from the group consisting of a $C_{1-12}$ alkyl, $CH_2=CH-$, $CH_2=C(C_{1-3}$ alkyl)—, $CH_2=CHC(O)-$, $CH_2=C(C_{1-3}$ alkyl)$C(O)-$, $CH_2=CHC(O)O-$, $CH_2=C(C_{1-3}$ alkyl)$C(O)O-$, $CH_2=C(phenyl)C(O)O-$, and $CH_2=C(C_{1-3}alkyl)S(O)_nO-$;

each of SP1, SP2 and SP3 is a spacer independently selected from the group consisting of —O—, —C(O)—, —S—, —S(O)—, —S(O)$_2$—, —N—, —NH—, —NCH$_3$—, —C—, —CH—, —(CH$_2$)$_q$—, —(CH(OH))$_q$—, —(CH$_2$CH(OH)CH$_2$)$_q$—, —(C(CH$_3$)$_2$)$_q$—, —(CH(CH$_3$))$_q$—, —NH(CH$_2$)$_2$NH—, —OC(O)—, —CO$_2$—, —NHCH$_2$CH$_2$C(O)—, —OCH$_2$CH$_2$C(O)—, —C(O)CH$_2$CH$_2$C(O)—, —C(O)NHCH$_2$CH$_2$NH—, —NHCH$_2$C(O)—, —NHC(O)—, —C(O)N—, —NC(O)—, —C(O)NH—, —NCH$_3$C(O)—, —C(O)NCH$_3$—, —(CH$_2$CH$_2$O)$_p$—, —(CH$_2$CH$_2$O)pCH$_2$CH$_2$—, —CH$_2$CH$_2$—(CH$_2$CH$_2$O)$_p$—, —OCH(CH$_2$O—)$_2$—, aryl, cyclopentanyl, cyclohexanyl, unsubstituted phenylenyl and phenylenyl substituted by 1 or 2 substituents selected from the group consisting of halo, $CF_3-$, $CF_3O-$, $CH_3O-$, —C(O)OH, —C(O)OC$_{1-3}$ alkyl, —C(O)CH$_3$, —CN, —NH$_2$, —OH, —NHCH$_3$, —N(CH$_3$)$_2$ and $C_{1-3}$ alkyl, p is 1-6, and q is 1-6;

provided that:

at least one of SP1, SP2 and SP3 is a spacer selected from the group consisting of A, B, C, D, and E:

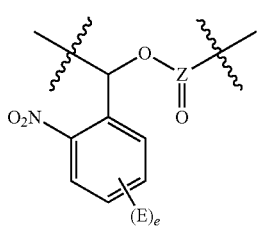

A

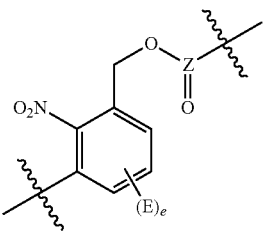

B

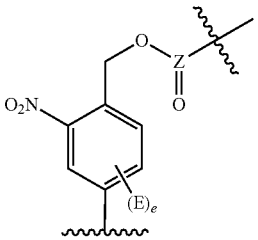

C

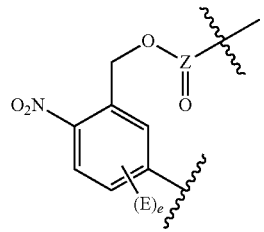

D

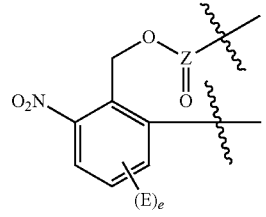

E wherein:

Z is C;

each E is halo; and e is 0, 1, 2 or 3; and provided that when EG and EG1 are both $CH_2=C(CH_3)C(O)O-(CH_2CH_2)OC(O)-$ or $CH_2=C(CH_3)C(O)NH-(CH_2CH_2)OC(O)-$, then the spacer is not

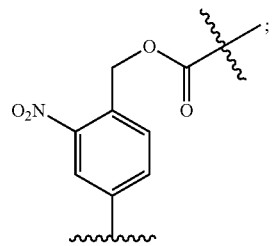 [SMILES: *C(=O)OCc1ccc(*)cc1[N+](=O)[O-]]

a compound of the formulae 89 to 96, or mixtures thereof

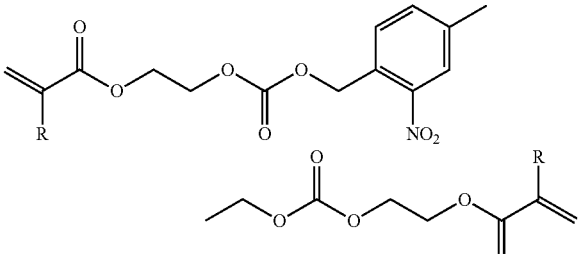

89: R = H
90: R = Me

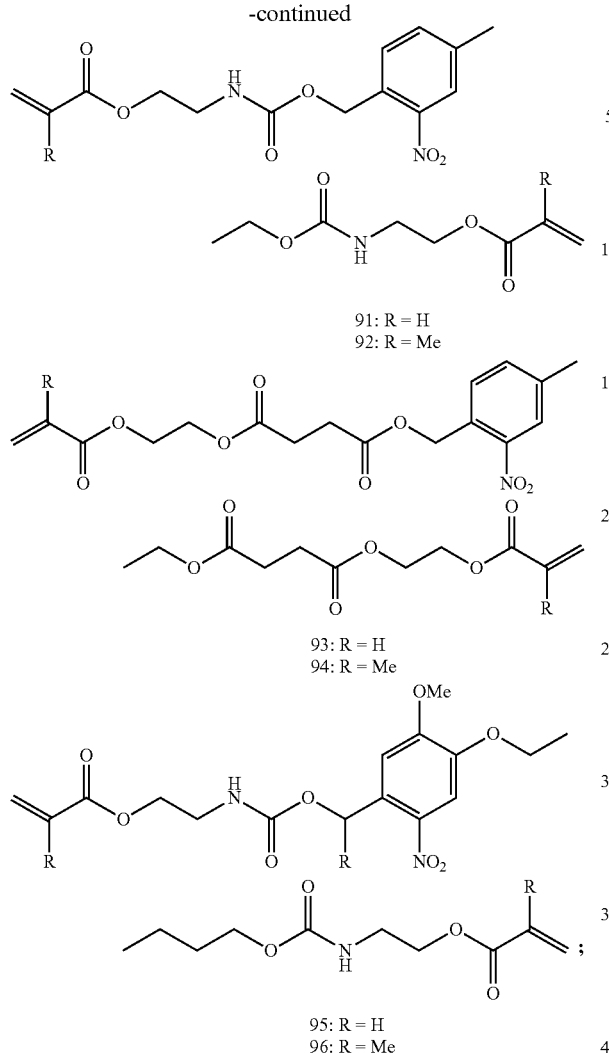

or
Bis-GMA, TEGDMA and DMAEMA; and
b) a primer.

2. The dental adhesive or primer of claim 1, wherein the formulation is selected from the group consisting of photocleavable primer or resin.

3. The dental adhesive or primer of claim 2, wherein the photocleavable primer or resin may comprise of about 10-99 wt % when mixed with a dental adhesive, and the acrylate or methacrylate may comprise of about 10-99 wt % when mixed with a dental adhesive.

4. The dental adhesive or primer of claim 1, wherein the primer is selected from the group consisting of photocleavable dimethacrylates or acrylates.

5. The dental adhesive or primer of claim 4, wherein the photocleavable dimethacrylates or acrylates comprise of a single photocleavable monomer, a mixture of photocleavable monomers or a mixture of photocleavable monomer(s) and non-photocleavable monomers or monomer blends.

6. The dental adhesive or primer of claim 4, wherein the camphorquinone is present in the solution at 0.25 wt %, and the 2-dimethylaminoethyl methacrylate is present at about 1 wt %.

7. The dental adhesive or primer of claim 4, wherein the acrylate or dimethacrylate in the mixture is present in about 50 wt %, 60 wt %, 70 wt %, 80 wt %, 90 wt %, 95 wt %.

8. The dental adhesive or primer of claim 4, wherein the acrylate or dimethacrylate in the mixture is present in about 40 wt %, 30 wt %, 20 wt %, 10 wt %, 5 wt %, 3 wt % or about 1 wt %.

9. The dental adhesive or primer of claim 1, wherein the primer is selected from the group consisting of a compound of the formulae 89 to 96, or mixtures thereof

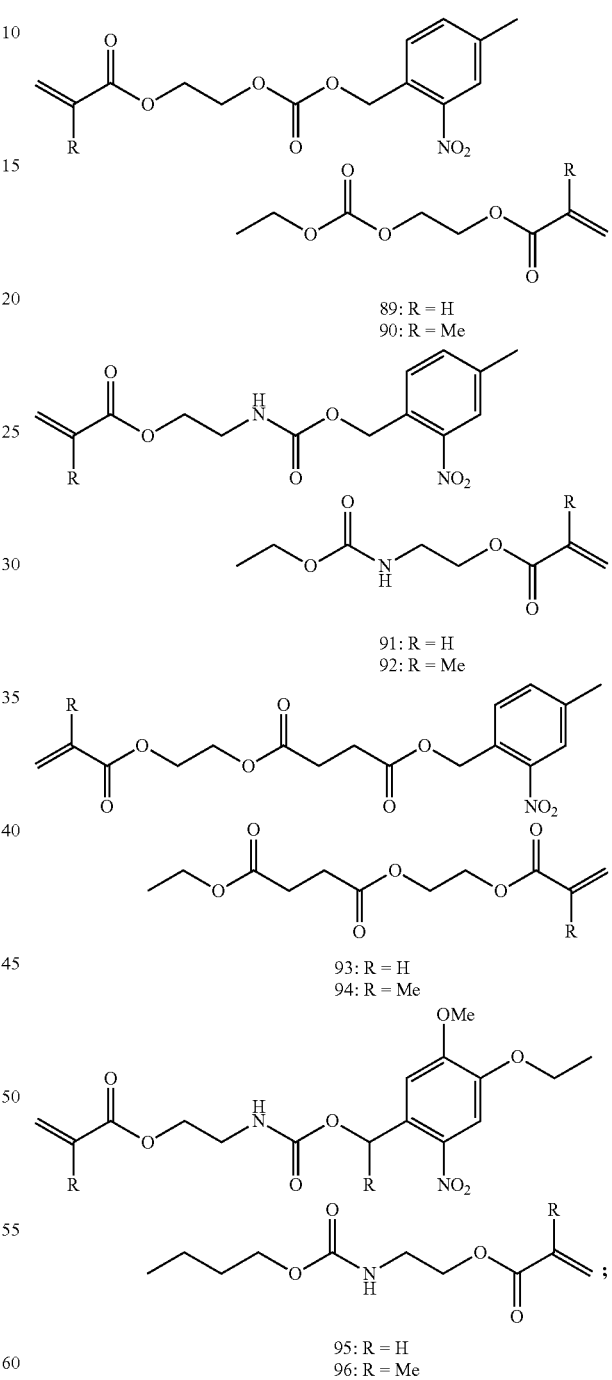

and Bis-GMA, TEGDMA and DMAEMA.

10. The dental adhesive or primer of claim 1, wherein the primer is selected from the group consisting of camphorquinone (CQ) and 2-dimethylaminoethyl methacrylate (DMAEMA), and a mixture thereof.

11. The dental adhesive or primer of claim 1, wherein the primer is in a solution.

12. The dental adhesive or primer of claim 11, wherein the solution is selected from water, organic solvents, or a mixture thereof.

13. The dental adhesive or primer of claim 1, wherein the primer or resin that is Bis-GMA, TEGDMA and DMAEMA is 1-50 wt % in the composition.

14. The dental adhesive or primer of claim 1, wherein the range of the concentration of the primer in the solution is selected from 0.0001 wt. % to 20 wt. %, 0.0001 wt. % to 15 wt. %, 0.0001 wt. % to 10 wt. %, about 0.001 wt. % to 10 wt. %, about 0.01 wt. % to 10 wt. %, about 0.1 wt. % to 10 wt. % or at about 0.1 wt. % to 5 wt. %.

15. The dental adhesive or primer of claim 1, wherein the concentration of the primer in the solution is 0.0001 wt %, 0.001 wt. %, 0.01 wt %, 0.1 wt %, 1.0 wt %, 5 wt %, 10 wt %, 15 wt %, 20 wt %, 25 wt % or more.

* * * * *